(12) United States Patent
Slatkine

(10) Patent No.: US 7,762,964 B2
(45) Date of Patent: Jul. 27, 2010

(54) METHOD AND APPARATUS FOR IMPROVING SAFETY DURING EXPOSURE TO A MONOCHROMATIC LIGHT SOURCE

(75) Inventor: Michael Slatkine, Herzlia (IL)

(73) Assignee: Candela Corporation, Wayland, MA (US)

(*) Notice: Subject to any disclaimer, the term of this patent is extended or adjusted under 35 U.S.C. 154(b) by 1305 days.

(21) Appl. No.: 10/498,382

(22) PCT Filed: Aug. 2, 2002

(86) PCT No.: PCT/IL02/00635

§ 371 (c)(1),
(2), (4) Date: Oct. 18, 2004

(87) PCT Pub. No.: WO03/049633

PCT Pub. Date: Jun. 19, 2003

(65) Prior Publication Data

US 2005/0234527 A1 Oct. 20, 2005
US 2009/0299440 A9 Dec. 3, 2009

Related U.S. Application Data

(63) Continuation-in-part of application No. PCT/IL02/00635, filed on Aug. 2, 2002, and a continuation-in-part of application No. 10/614,672, filed on Jul. 7, 2003, now Pat. No. 7,184,614.

(30) Foreign Application Priority Data

| Dec. 10, 2001 | (IL) | ................................. 147009 |
| Jun. 6, 2002 | (IL) | ................................. 150094 |
| Feb. 22, 2004 | (IL) | ................................. 160510 |

(51) Int. Cl.
A61H 7/00 (2006.01)

(52) U.S. Cl. ............................................. 601/7; 601/15
(58) Field of Classification Search ................... 601/7, 601/10, 15, DIG. 1, DIG. 4, DIG. 5
See application file for complete search history.

(56) References Cited

U.S. PATENT DOCUMENTS 3,982,541 A 9/1976 L'Esperance, Jr.

(Continued)

FOREIGN PATENT DOCUMENTS

DE 37 30 469 A1 6/1988

(Continued)

OTHER PUBLICATIONS

"The Physiology Coloring Book", W. Kapit et al., Harper Collins Publishers, 1987, pp. 88-89.

(Continued)

Primary Examiner—Michael A. Brown
(74) Attorney, Agent, or Firm—Proskauer Rose LLP

(57) ABSTRACT

A method and apparatus are disclosed for enhancing the absorption of light in targeted skin structures. A vacuum chamber having a clear transmitting element transparent to intense pulsed light on its proximate end and an aperture on its distal end is placed on a skin target. After applying a vacuum to the vacuum chamber and modulating the applied vacuum, the concentration of blood and/or blood vessels is increased within a predetermined depth below the skin surface of the skin target. Optical energy associated with intense pulsed light directed in a direction substantially normal to a skin surface adjoining the skin target is absorbed within the predetermined depth. The apparatus is suitable for treating vascular lesions with a reduced treatment energy density level than that of the prior art and for evacuating condensed vapors produced during the cooling of skin prior to firing an intense pulsed light with a controlled delay.

27 Claims, 36 Drawing Sheets

U.S. PATENT DOCUMENTS

| | | | |
|---|---|---|---|
| 4,592,353 A | 6/1986 | Daikuzono | |
| 4,736,743 A | 4/1988 | Daikuzono | |
| 4,838,281 A | 6/1989 | Rogers et al. | |
| 4,976,709 A | 12/1990 | Sand | |
| 5,057,104 A | 10/1991 | Chess | |
| 5,059,192 A | 10/1991 | Zaias | |
| 5,066,293 A | 11/1991 | Furumoto | |
| 5,217,455 A | 6/1993 | Tan | |
| 5,226,907 A | 7/1993 | Tankovich | |
| 5,282,797 A | 2/1994 | Chess | |
| 5,312,395 A | 5/1994 | Tan et al. | |
| 5,344,418 A | 9/1994 | Ghaffari | |
| 5,401,270 A | 3/1995 | Schoenborn et al. | |
| 5,411,502 A | 5/1995 | Zair | |
| 5,429,601 A | 7/1995 | Conley et al. | |
| 5,431,647 A | 7/1995 | Purcell, Jr. et al. | |
| 5,449,354 A | 9/1995 | Konwitz et al. | |
| 5,527,308 A | 6/1996 | Anderson et al. | |
| 5,530,780 A | 6/1996 | Ohsawa | |
| 5,558,660 A | 9/1996 | Dreier | |
| 5,595,568 A | 1/1997 | Anderson et al. | |
| 5,626,631 A | 5/1997 | Eckhouse | |
| 5,630,811 A | 5/1997 | Miller | |
| 5,655,547 A | 8/1997 | Karni | |
| 5,735,844 A | 4/1998 | Anderson et al. | |
| 5,745,519 A | 4/1998 | Ruda et al. | |
| 5,814,041 A | 9/1998 | Anderson et al. | |
| 5,853,407 A | 12/1998 | Miller | |
| 5,871,521 A | 2/1999 | Kaneda et al. | |
| 5,879,346 A | 3/1999 | Waldman et al. | |
| 5,885,273 A | 3/1999 | Eckhouse et al. | |
| 5,947,957 A | 9/1999 | Morris et al. | |
| 5,961,475 A | 10/1999 | Guitay | |
| 5,964,749 A | 10/1999 | Eckhouse et al. | |
| 6,011,890 A | 1/2000 | Neuberger | |
| 6,096,029 A | 8/2000 | O'Donnell, Jr. | |
| 6,120,497 A | 9/2000 | Anderson et al. | |
| 6,132,392 A | 10/2000 | Stone | |
| 6,142,650 A | 11/2000 | Brown et al. | |
| 6,149,645 A | 11/2000 | Tobinick | |
| 6,165,170 A | 12/2000 | Wynne et al. | |
| 6,185,356 B1 | 2/2001 | Parker et al. | |
| 6,197,020 B1 | 3/2001 | O'Donnell, Jr. | |
| 6,214,034 B1 | 4/2001 | Azar | |
| 6,261,310 B1 | 7/2001 | Neuberger et al. | |
| 6,264,649 B1 | 7/2001 | Whitcroft et al. | |
| 6,273,884 B1 | 8/2001 | Altshuler et al. | |
| 6,280,438 B1 | 8/2001 | Eckhouse et al. | |
| 6,508,813 B1 * | 1/2003 | Altshuler | 606/9 |
| 6,530,920 B1 | 3/2003 | Whitcroft et al. | |
| 6,544,259 B1 | 4/2003 | Tsaliovich | |
| 6,662,054 B2 | 12/2003 | Kreindel et al. | |
| 7,108,689 B2 | 9/2006 | Eckhouse et al. | |
| 7,184,614 B2 | 2/2007 | Slatkine | |
| 2002/0012860 A1 | 1/2002 | Yoo | |
| 2002/0013602 A1 | 1/2002 | Huttner | |
| 2002/0034012 A1 | 3/2002 | Santoro et al. | |
| 2002/0128600 A1 | 9/2002 | Nissels | |
| 2002/0128635 A1 | 9/2002 | Altshuler et al. | |
| 2002/0169442 A1 | 11/2002 | Neev | |
| 2003/0083536 A1 | 5/2003 | Eshel et al. | |
| 2004/0077977 A1 | 4/2004 | Ella et al. | |
| 2004/0082940 A1 | 4/2004 | Black et al. | |
| 2004/0254599 A1 | 12/2004 | Lipoma et al. | |
| 2005/0251117 A1 | 11/2005 | Anderson et al. | |
| 2005/0261584 A1 | 11/2005 | Eshel et al. | |
| 2006/0189964 A1 | 8/2006 | Anderson et al. | |
| 2006/0241573 A1 | 10/2006 | Roersma et al. | |
| 2007/0027411 A1 * | 2/2007 | Ella et al. | 601/7 |
| 2007/0179482 A1 | 8/2007 | Anderson | |

FOREIGN PATENT DOCUMENTS

| | | |
|---|---|---|
| DE | 198 49 301 | 4/2000 |
| EP | 0 103 664 | 3/1984 |
| EP | 0 761 257 A2 | 3/1997 |
| EP | 0 880 940 A2 | 12/1998 |
| EP | 933096 | 8/1999 |
| EP | 1 031 324 | 8/2000 |
| EP | 1116476 | 7/2001 |
| EP | 1 168 535 | 1/2002 |
| GB | 1 494 324 | 12/1977 |
| JP | 2001-212231 | 8/2001 |
| JP | 2005-087520 | 4/2005 |
| WO | WO 99/27863 | 12/1998 |
| WO | WO 99/27863 | 6/1999 |
| WO | WO 99/46005 A | 9/1999 |
| WO | WO00/60711 | 10/2000 |
| WO | WO 00/72771 | 12/2000 |
| WO | WO 00/72771 A1 | 12/2000 |
| WO | 2003/103523 | 12/2003 |
| WO | WO 2004/004803 | 1/2004 |

OTHER PUBLICATIONS

International Search Report for PCT/IL02/00635 (5 pages).
International Preliminary Examination Report for PCT/IL02/00635 (7 pages).
"Effects of Tissue Optical Clearing, . . . ,Lasers Light within Tissue (G. Vergas & A.J. Welch, Laser in Surgery and Medicine", Supp. 13, 2001, p. 26).
PCT International Search Report for corresponding PCT application (PCT/IL02/00635) (6 pages).
PCT International Search Report for PCT application (PCT/IL03/00277) (3 pages).

* cited by examiner

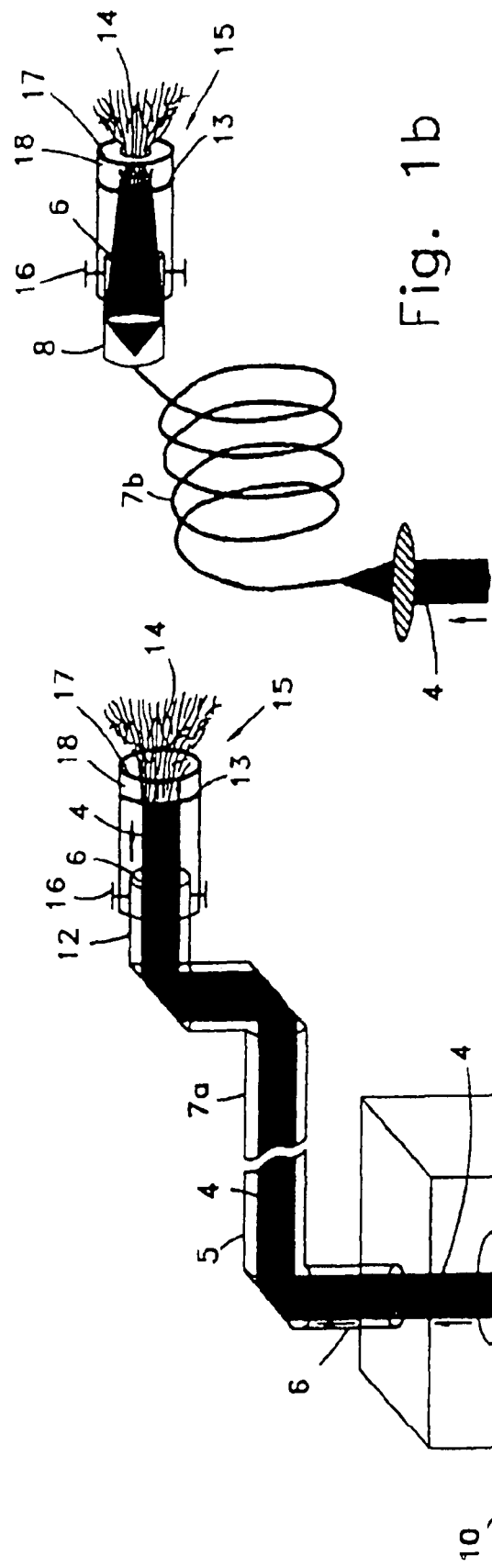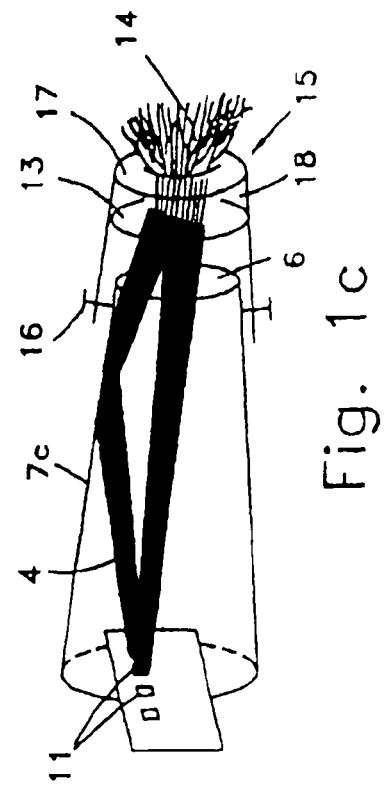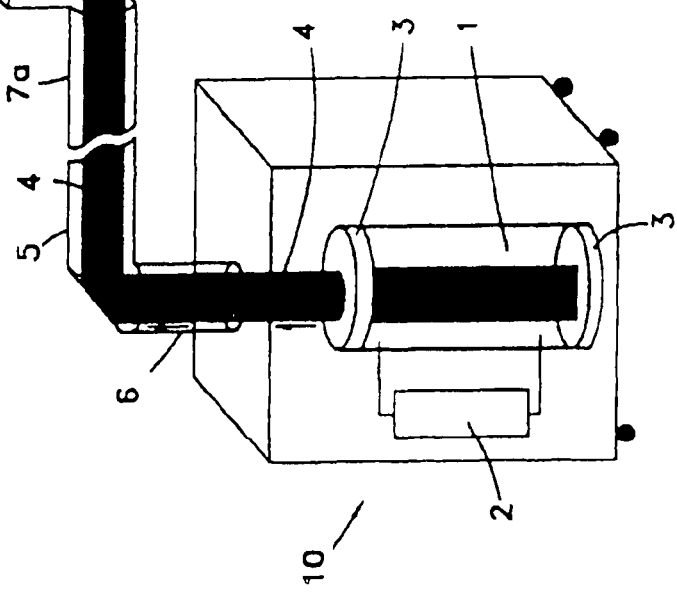

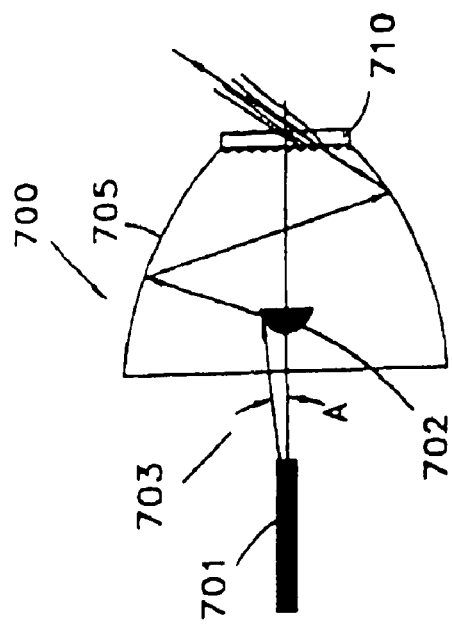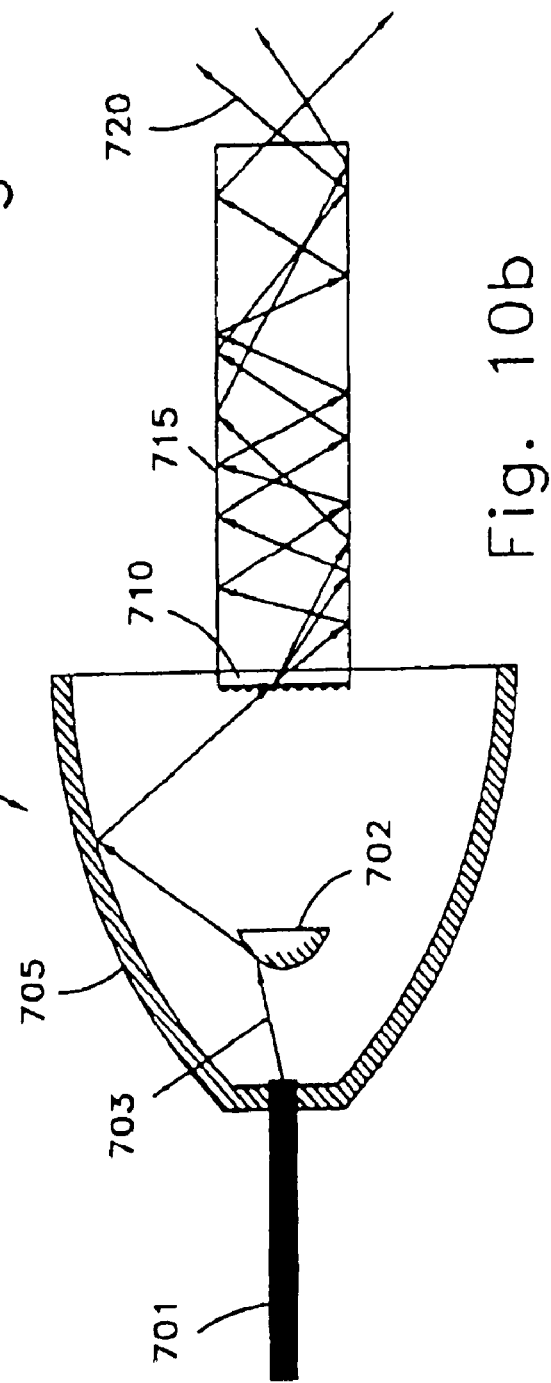

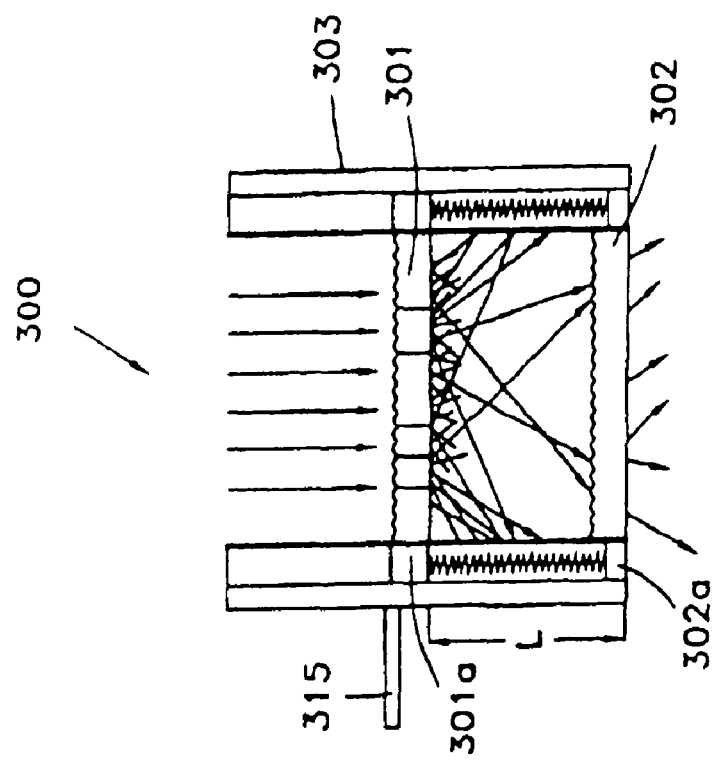
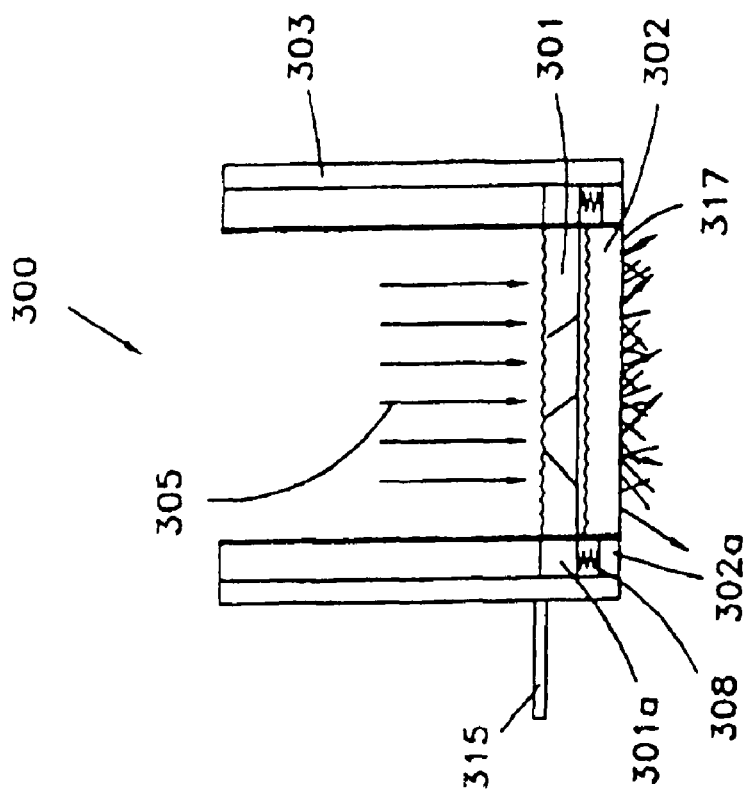
Fig. 12a
Fig. 12b

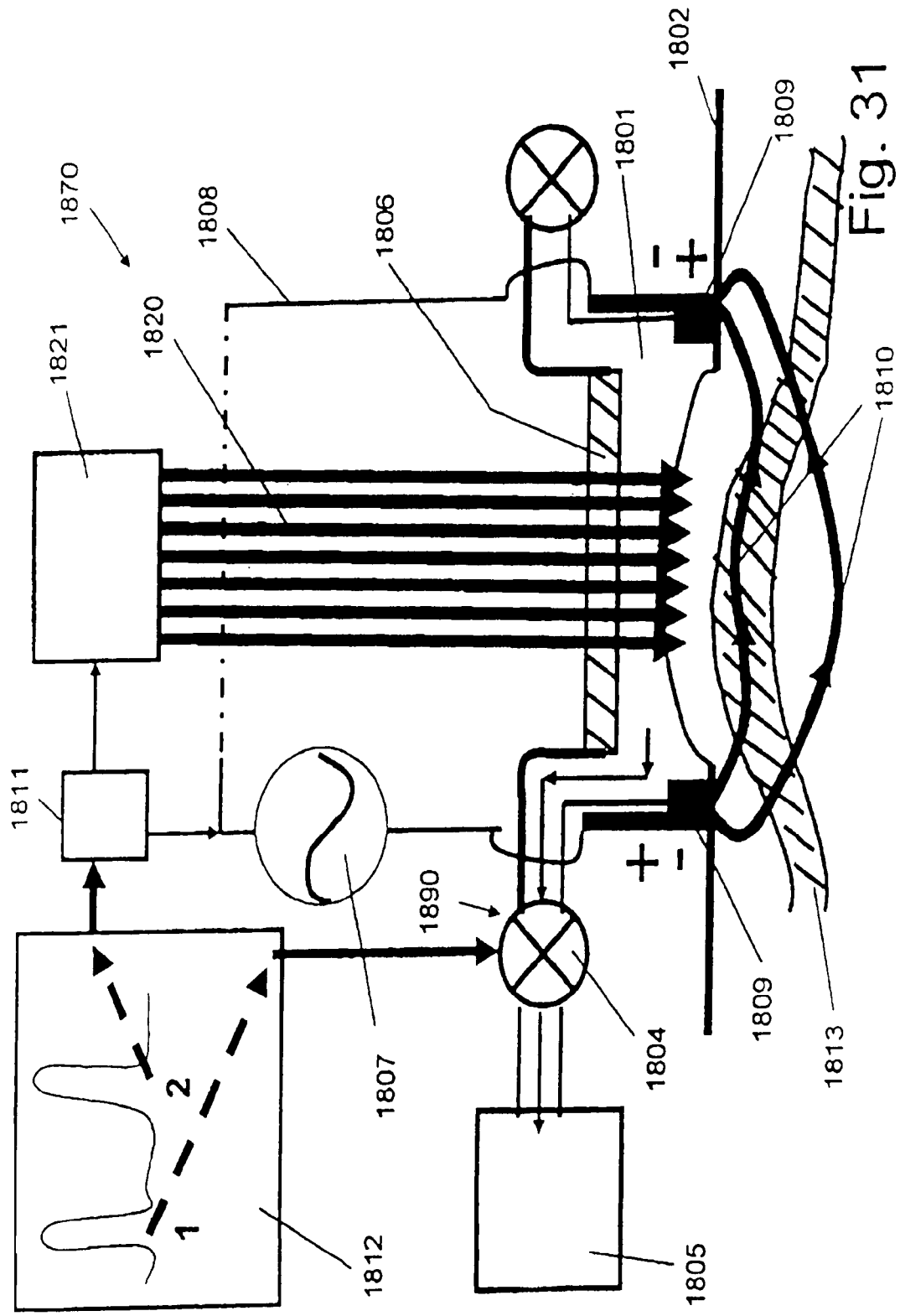

METHOD AND APPARATUS FOR IMPROVING SAFETY DURING EXPOSURE TO A MONOCHROMATIC LIGHT SOURCE

CROSS REFERENCE TO RELATED APPLICATIONS

This application is a continuation-in-part of international application no. PCT/IL02/00635, filed on Aug. 2, 2002, which claims the benefit of and priority to Israeli patent application no. 147009, filed on Dec. 10, 2001, and Israeli patent application no. 150094, filed on Jun. 6, 2002. This application also claims the benefit of and priority to Israeli patent application no. 160510, filed on Feb. 22, 2004. This application is also a continuation-in-part of U.S. application Ser. No. 10/614,672, filed Jul. 7, 2003, now U.S. Pat. No. 7,184,614.

FIELD OF THE INVENTION

The present invention is related to the field of laser-based light sources. More specifically, the invention is related to the utilization of light sources for the non-invasive treatment of skin disorders, whereby light is selectively absorbed by blood vessels, for the treatment or destruction of blood vessels.

BACKGROUND OF THE INVENTION

Prior art very high intensity, short duration pulsed light systems which operate in the visible part of the spectrum, such as flashlamps or intense pulsed lasers are currently used in aesthetic treatments by one of two known ways: a) Applying the light to the skin without applying any pressure on the treatment zone, so as not to interfere with the natural absorption properties of skin; and b) Applying pressure onto the skin by means of the exit window of the treatment device in contact with the skin, thereby expelling blood from the light path within the skin and enabling better transmission of the light to a skin target.

The major applications of intense pulsed light or intense pulsed laser systems are hair removal, coagulation of blood vessels for e.g. port wine stains, telangectasia, spider veins and leg veins, multiple heating of blood vessels for e.g. rosacea, treatment of pigmented skin such as erasure of black stains and sun stains or tattoo removal; and removal of fine wrinkles by heating the tissue around the wrinkles, normally referred to as photorejuvenation.

U.S. Pat. Nos. 5,226,907, 5,059,192, 5,879,346, 5,066,293, 4,976,709, 6,120,497, 6,120,497, 5,626,631, 5,344,418, 5,885,773, 5,964,749, 6,214,034 and 6,273,884 describe various laser and non-coherent intense pulsed light systems. These prior art light systems are not intended to increase the natural absorption of the skin.

U.S. Pat. Nos. 5,595,568 and 5,735,844 describe a system for hair removal whereby pressure is applied to the skin by a transparent contact device in contact therewith, in order to expel blood present in blood vessels from a treatment zone. In this approach blood absorption decreases in order to increase subcutaneous light penetration.

Applying a vacuum to the skin is a known prior art procedure, e.g. for the treatment of cellulites, which complements massaging the skin. Such a procedure produces a flow of lymphatic fluids so that toxic substances may be released from the tissue. As the vacuum is applied, a skin fold is formed. The skin fold is raised above the surrounding skin surface, and the movement of a handheld suction device across the raised skin performs the massage. The suction device is moved in a specific direction relative to the lymphatic vessels, to allow lymphatic fluids to flow in their natural flow direction. The lymphatic valve in each lymphatic vessel prevents the flow of lymphatic fluid in the opposite direction, if the suction device were moved incorrectly. Liquids generally accumulate if movement is not imparted to the raised skin. The massage, which is generally carried out by means of motorized or hand driven wheels or balls, draws lymphatic fluids from cellulite in the adipose subcutaneous region and other deep skin areas, the depth being approximately 5-10 mm below the dermis.

U.S. Pat. No. 5,961,475 discloses a massaging device with which negative pressure is applied to the skin together during massaging. A similar massaging device which incorporates a radio frequency (RF) source for the improvement of lymphatic flow by slightly heating the adipose tissue is described in U.S. Pat. No. 6,662,054. Some massaging systems, such as those produced by Deka and Cynosure, add a low power, continuous working (CW) light source of approximately 0.1-2 W/cm$^2$, in order to provide deep heating of the adipose tissue by approximately 1.3° C. degrees and to enhance lymphatic circulation. The light sources associated with vacuum lymphatic massage devices are incapable of inducing blood vessel coagulation due to their low power. Also, prior art vacuum lymphatic massage devices are adapted to induce skin protrusion or to produce a skin fold by applying a vacuum.

Selective treatment of blood vessels by absorption of intense pulsed laser radiation is possible with Dye lasers operating at 585 nm, as well as with other types of lasers. Photorejuvenation has also been performed with Diode lasers in the near infrared spectral band of 800-980 nm and with Nd:YAG lasers having a frequency of approximately 1064 nm with limited success. The light emitted by such lasers is not well absorbed by tiny blood vessels or by the adjoining liquid. Broad band non-coherent intense pulsed light systems are also utilized for photorejuvenation with some success, although requiring more than 10 repeated treatments. The heat which is absorbed by the blood vessels, as a result of the light emitted by the intense short pulse devices, is transferred to adjacent collagen bundles.

The absorption of pulsed Diode and Nd:YAG laser beams by blood vessels is lower than the absorption of pulsed Dye laser beam. In order to compensate for limited photorejuvenation with red and infrared intense pulsed light and laser systems, a very high energy density as high as 30-60 J/cm$^2$ needs to be generated. At such an energy density, the melanin-rich epidermis, particularly in dark skin, is damaged if not chilled. A method to reduce the energy density of intense pulsed lasers or non-coherent intense pulsed light sources which operate in the visible or the near infrared regions of the spectrum will therefore beneficial.

Pulsed dye lasers operating in the yellow spectral band of approximately 585-600 nm, which is much better absorbed by blood vessels, are also utilized for the smoothing of fine wrinkles. The energy density of light emitted by Dye lasers, which is approximately 3-5 J/cm$^2$, is much lower than that of light emitted by other lasers. However, the pulse durations of light emitted by Dye lasers are very short, close to 1 microsecond, and therefore risk the epidermis in darker skin. Treatments of wrinkles with Dye lasers are slow, due to the low concentration of absorbing blood vessels, as manifested by the yellow or white color of treated skin, rather than red or pink characteristic of skin having a high concentration of blood vessels. Due to the low energy density of light emitted by Dye lasers, as many as 10 treatments may be necessary. A method to reduce the energy density of light generated by Dye lasers, or to reduce the number of required treatments at currently used energy density levels, for the treatment of fine wrinkles, would be beneficial.

Pulsed Dye lasers operating at 585 nm are also utilized for the treatment of vascular lesions such as port wine stains or telangectasia or for the treatment of spider veins. The energy density of the emitted light is approximately 10-15 J/cm$^2$, and is liable to cause a burn while creating the necessary purpura. A method to reduce the energy density of light emitted by Dye lasers for the treatment of vascular lesions would be highly beneficial.

Hair removal has been achieved by inducing the absorption of infrared light, which is not well absorbed by melanin present in hair strands, impinging on blood vessels. More specifically, absorption of infrared light by blood vessels at the distal end of hair follicles contributes to the process of hair removal. High intensity pulsed Nd:YAG lasers, such as those produced by Altus, Deka, and Iridex, which emit light having an energy density of more than 50 J/cm$^2$, are used for hair removal. The light penetration is deep, and is often greater than 6 millimeters. Some intense pulsed light or pulsed laser systems, such as that produced by Syneron, used for hair removal or photorejuvenation also employ an RF source for further absorption of energy within the skin.

The evacuation of smoke or vapor, which is produced following the impingement of monochromatic light on a skin target, from the gap between the distal end window of a laser system and the skin target, is carried out in conjunction with prior art ablative laser systems such as $CO_2$, Erbium or Excimer laser systems. The produced smoke or vapor is purged by the introduction of air at greater than atmospheric pressure. Coagulative lasers such as pulsed dye lasers or pulsed Nd:YAG lasers, which treat lesions under the skin surface, are not provided with an evacuation chamber.

Some prior art intense pulsed laser systems, which operate in the visible and near infrared region of the spectrum and treat lesions under the skin surface, e.g. vascular lesions, with pulsed dye laser systems or pulsed Nd:YAG lasers, employ a skin chilling system. Humidity generally condenses on the distal window, due to the use of a skin chilling system. It would be advantageous to evacuate the condensed vapors from the distal window of the laser system prior to the next firing of the laser.

It is an object of the present invention to provide a method and apparatus for the treatment of subcutaneous lesions, such as vascular lesions, by a high intensity pulsed laser system operating at wavelengths shorter than 1800 nm without causing a burn to the epidermis.

It is an object of the present invention to provide a method and apparatus for controlling the depth of subcutaneous light absorption.

It is an object of the present invention to provide a method and apparatus for increasing the absorption of light which impinges a skin target by increasing the concentration of blood vessels thereat.

It is an additional object of the present invention to provide a method and apparatus by which the energy density level of intense pulsed light that is suitable for hair removal, fine wrinkle removal, including removal of wrinkles around the eyes and in the vicinity of the hands or the neck, and the treatment of port wine stain or rosacea may be reduced relative to that of the prior art.

It is an additional object of the present invention to provide a method and apparatus by which the number of required treatments for hair removal, fine wrinkle removal, including removal of wrinkles around the eyes and in the vicinity of the hands or the neck, and the treatment of port wine stain or rosacea at currently used energy density levels may be reduced relative to that of the prior art.

It is yet an additional object of the present invention to provide a method and apparatus for repeated evacuation, prior to the firing of a subsequent laser pulse, of vapors which condensed on the distal window due to the chilling of laser treated skin.

Other objects and advantages of the invention will become apparent as the description proceeds.

SUMMARY OF THE INVENTION

The present invention comprises a method for controlling the depth of light absorption by blood vessels under a skin surface comprising placing a vacuum chamber which is transparent to intense pulsed light on a skin target; applying a vacuum to said vacuum chamber, whereby said skin target is drawn to said vacuum chamber and the concentration of blood and/or blood vessels within said skin target is increased; modulating the applied vacuum so that the concentration of blood and/or blood vessels is increased within a predetermined depth below the skin surface; and directing intense pulsed light to said skin target, optical energy associated with the directed intense pulsed light being absorbed within said predetermined depth.

The depth under the skin surface at which optical energy is absorbed may be selected in order to thermally injure or treat predetermined skin structures located at said depth. As referred to herein, a "skin structure" is defined as any damaged or healthy functional volume of material located under the epidermis, such as blood vessels, collagen bundles, hair shafts, hair follicles, sebaceous glands, sweat glands, adipose tissue. Depending on the blood concentration within the skin target, the intense pulsed light may propagate through the skin surface and upper skin layers without being absorbed thereat and then being absorbed at a skin layer corresponding to that of a predetermined skin structure. As referred to herein, the term "light" means both monochromatic and non-coherent light. The terms "light absorption" and "optical energy absorption" refer to the same physical process and are therefore interchangeable.

In contrast with a prior art vacuum-assisted method of laser or intense pulsed light treatment wherein a skin fold is produced following application of the vacuum, vacuum-assisted drawn skin in accordance with the method of the present invention is not distorted, but rather is slightly and substantially uniformly drawn to the vacuum chamber, protruding approximately 1 mm from the adjoining skin surface. The maximum protrusion of the drawn skin from the adjoining skin surface is limited by a clear transmitting element defining the proximate end of the vacuum chamber. The clear transmitting element is separated from the adjoining skin surface by a gap of preferably 2 mm, and ranging from 0.5-40 mm.

As referred to herein, "vacuum modulation" means adjustment of the vacuum level within, or of the frequency by which vacuum is applied to, the vacuum chamber. By properly modulating the vacuum, the blood flow rate, in a direction towards the vacuum chamber, within blood vessels at a predetermined depth below the skin surface can be controlled. As the concentration of blood and/or blood vessels is increased within the skin target, the number of light absorbing chromophores is correspondingly increased at the predetermined depth. The value of optical energy absorbence at the predetermined depth, which directly influences the efficacy of the treatment for skin disorders, is therefore increased.

Preferably
a) The wavelength of the intense pulsed light ranges from 400 to 1800 nm.
b) The pulse duration of the intense pulsed light ranges from 10 nanoseconds to 900 msec.
c) The energy density of the intense pulsed light ranges from 2 to 150 $J/cm^2$.
d) The level of the applied vacuum within the vacuum chamber ranges from 0 to 1 atmosphere.
e) The frequency of vacuum modulation ranges from 0.2 to 100 Hz.
f) The intense pulsed light is fired after a predetermined delay following application of the vacuum.
g) The predetermined delay ranges from 10 msec to 1 second.
h) The duration of vacuum application to the vacuum chamber is less than 2 seconds.
i) Vacuum modulation is electronically controlled.

Due to implementation of the method of the present invention, the treatment energy density level for various types of treatment is significantly reduced, on the average of 50% with respect with that associated with prior art devices. The treatment energy density level is defined herein as the minimum energy density level which creates a desired change in the skin structure, such as coagulation of a blood vessel, denaturation of a collagen bundle, destruction of cells in a gland, destruction of cells in a hair follicle, or any other desired effects. The following is the treatment energy density level for various types of treatment performed with use of the present invention:

a) treatment of vascular lesions, port wine stains, telangectasia, rosacea, and spider veins with light emitted from a dye laser unit and having a wavelength of 585 nm: 5.12 $J/cm^2$;
b) treatment of vascular lesions, port wine stains, telangectasia, rosacea, and spider veins with light emitted from a diode laser unit and having a wavelength of 940 nm: 10-30 $J/cm^2$;
c) treatment of vascular lesions with light emitted from an intense pulsed non-coherent light unit and having a wavelength of 570-900 nm: 5-20 $J/cm^2$;
d) photorejuvination with light emitted from a dye laser unit and having a wavelength of 585 nm: 1-4 $J/cm^2$;
e) photorejuvination with light emitted from an intense pulsed non-coherent light unit and having a wavelength of 570.900 nm: 5.20 $J/cm^2$;
f) photorejuvination with a combined effect of light emitted from an intense pulsed non-coherent light unit and having a wavelength of 570-900 nm and of a RF source: 10 $J/cm^2$ for both the intense pulsed non-coherent light unit and RF source; and
g) hair removal with light emitted from a Nd:YAG laser unit and having a wavelength of 1604 nm: 25.35 $J/cm^2$.

The present invention is also directed to an apparatus for enhancing the absorption of light in targeted skin structures, comprising:

a) a vacuum chamber placed on a skin target which is formed with an aperture on the distal end thereof and provided with a clear transmitting element on the proximate end thereof, said transmitted element being transparent to intense pulsed light directed to said skin target and suitable for transmitting the intense pulsed light in a direction substantially normal to a skin surface adjoining said skin target;
b) means for applying a vacuum to said vacuum chamber, the level of the applied vacuum suitable for drawing said skin target to said vacuum chamber via said aperture; and
c) means for modulating the applied vacuum in such a way that the concentration of blood and/or blood vessels is increased within a predetermined depth below the skin surface of said skin target, optical energy associated with the directed intense pulsed light being absorbed within said predetermined depth.

As referred to herein, "distal" is defined as a direction towards the exit of the light source and "proximate" is defined as a direction opposite from a distal direction.

The ratio of the maximum length to maximum width of the aperture formed on the distal end of the vacuum chamber ranges from approximately 1 to 4.

In one embodiment of the invention, the vacuum chamber is connected to, or integrally formed with, a proximately disposed handpiece through which intense pulsed light propagates towards the skin target.

The intense pulsed light is suitable for hair removal, photorejuvenation, treatment of vascular lesions, treatment of sebaceous or sweat glands, treatment of warts, or treatment of pigmented lesions.

The present invention is also directed to an apparatus for enhancing the absorption of light in targeted skin structures, comprising:

a) an intense pulsed light source;
b) a U-shaped evacuation chamber positionable on a skin target;
c) a handpiece for directing intense pulsed light to a skin target which is connected to, or integral with, said evacuation chamber;
d) a clear transmitting element mounted in the distal end of said handpiece, said transmitted element being transparent to intense pulsed light directed to said skin target and suitable for transmitting the intense pulsed light in a direction substantially normal to a skin surface adjoining said skin target;
e) a rim for sealing the peripheral contact area between the skin surface adjoining said skin target and the wall of the handpiece; and
f) means for applying a vacuum to said evacuation chamber, the level of the applied vacuum suitable for drawing said skin target to said evacuation chamber and for increasing the concentration of blood and/or blood vessels within a predetermined depth below the skin surface of said skin target, optical energy associated with the directed intense pulsed light being absorbed within said predetermined depth.

The terms "evacuation chamber" and "vacuum chamber" as referred to herein are interchangeable.

The vacuum applying means preferably comprises a vacuum pump and at least one control valve.

The apparatus preferably further comprises control means for controlling operation of the vacuum pump, the at least one control valve, and the intense pulsed light source. The control means is suitable for firing the intense pulsed light source after a predetermined delay following operation of the vacuum pump. Alternatively, the control means is suitable for firing the intense pulsed light source after a predetermined delay following opening of the at least one control valve.

The control means is also suitable for increasing the pressure in the evacuation chamber to atmospheric pressure following deactivation of the intense pulsed light source, to allow for effortless repositioning of the evacuation chamber to a second skin target.

The intense pulsed light source is selected from the group of Dye laser, Nd:YAG laser, Diode laser, Alexandrite laser, Ruby laser, Nd:YAG frequency doubled laser, Nd:Glass laser and a non-coherent intense pulse light source. The light emitted from the light source has any wavelength band between 400 nm and 1800 nm.

In one aspect, the apparatus further comprises a pulsed radio frequency (RF) source for directing suitable electromagnetic waves to the skin target. The frequency of the electromagnetic waves ranges from 0.2-10 MHz. The RF source is preferably a bipolar RF generator which generates alternating voltage applied to the skin surface via wires and electrodes. The control means is suitable for transmitting a first command pulse to the at least one control valve and a second command pulse to both the intense pulsed light source and RF source.

In one aspect, the apparatus further comprises an erythema sensor, said sensor suitable for measuring the degree of skin redness induced by the vacuum applying means. The control means is suitable for controlling, prior to firing the light source, the energy density of the light emitted from the light source, in response to the output of the erythema sensor.

The present invention is also directed to an apparatus for treating vascular lesions, comprising:
 a) a Dye laser unit;
 b) a vacuum chamber placed on a skin target which is formed with an aperture on the distal end thereof and provided with a clear transmitting element on the proximate end thereof, said transmitted element being transparent to light which is emitted from the laser unit and directed to said skin target and being suitable for transmitting the light in a direction substantially normal to a skin surface adjoining said skin target;
 c) a handpiece which is connected to, or integral with, said vacuum chamber, for directing light to a skin target;
 d) a rim for sealing the peripheral contact area between the skin surface adjoining said skin target and the wall of the handpiece;
 e) a vacuum pump for applying a vacuum to said vacuum chamber, the level of the applied vacuum suitable for drawing said skin target to said vacuum chamber via said aperture;
 f) a control unit for controlling operation of the vacuum pump and laser unit; and
 g) means for modulating the applied vacuum by said control unit in such a way that the concentration of blood and/or blood vessels is increased within a predetermined depth below the skin surface of said skin target, optical energy associated with the directed intense pulsed light capable of being absorbed within said predetermined depth and treating a vascular lesion.

The present invention also comprises an apparatus for evacuating condensed vapors produced during the cooling of skin prior to firing an intense pulsed light, comprising:
 a) a vacuum chamber having a proximate end and positionable on a skin target such that a gap is formed between the proximate end thereof and the skin target, said proximate end being transparent to intense pulsed light directed to said skin target and to targeted skin structures located below the epidermis within the projected area of the proximate end and suitable for transmitting the intense pulsed light in a direction substantially normal to a skin surface adjoining said skin target;
 b) means for skin cooling, said skin cooling means adapted to reduce the rate of temperature increase of the epidermis at the skin target; and
 c) means for applying a vacuum to said vacuum chamber, the level of the applied vacuum suitable for—
  i. drawing said skin target to said vacuum chamber;
  ii. increasing the concentration of blood and/or blood vessels within a predetermined depth below the skin surface of said skin target corresponding with the depth of said targeted skin structures, optical energy associated with the directed intense pulsed light being absorbed within said targeted skin structures; and
  iii. evacuating condensed vapors which are produced within said gap and condense on said proximate end during the cooling of skin.

In one aspect, the skin cooling means is a metallic plate in abutment with said vacuum chamber on the external side thereof and positionable on the skin surface adjoining said skin target, said plate being cooled by means of a thermoelectric cooler operative to cool the lateral sides of the vacuum chamber.

In another aspect, the skin cooling means is a gel, a low temperature liquid or gas applied onto the skin target.

The present invention is also directed to a method for treatment of lesions by the absorption of light in targeted skin structures, comprising the steps of:
 a) placing a U-shaped vacuum chamber which is transparent to intense pulsed light and provided with two opposed conduits on a skin target;
 b) applying a vacuum to said vacuum chamber via a first conduit;
 c) increasing the vacuum level within said vacuum chamber by occluding a second conduit, whereby said skin target is drawn to said vacuum chamber and the concentration of blood and/or blood vessels at a predetermined depth below the skin surface of said skin target is increased;
 d) firing the intense pulsed light source after a predetermined delay following step c) such that intense pulsed light is directed to targeted skin structures below said skin target, optical energy associated with the directed intense pulsed light capable of being absorbed within said predetermined depth and treating a lesion.

In one aspect, the second conduit is occluded by placement of a finger thereon.

In one aspect, the method further comprises the steps of increasing the pressure within the vacuum chamber to atmospheric pressure by opening the second conduit and repositioning the vacuum chamber.

The lesions are selected from the group of vascular lesions including port wine stains, telangectasia, rosacea, spider veins, unwanted hairs, damaged collagen, acne, warts, keloids, sweat glands, and psoriasis.

The present invention also comprises a method for evacuating condensed vapors produced during the cooling of skin prior to firing an intense pulsed light, comprising:
 a) placing a U-shaped vacuum chamber which is transparent to intense pulsed light and provided with two opposed conduits on a skin target;
 b) chilling the skin target;
 c) applying a vacuum to said vacuum chamber via a first conduit;
 d) increasing the vacuum level within said vacuum chamber by occluding a second conduit, whereby said skin target is drawn to said vacuum chamber and the concentration of blood and/or blood vessels at a predetermined depth below the epidermis of said skin target is increased;
 e) firing the intense pulsed light source after a predetermined delay following step d) such that intense pulsed light is directed to targeted skin structures below said skin target, optical energy associated with the directed intense pulsed light capable of being absorbed within said predetermined depth and treating a lesion.

f) evacuating condensed vapors which are produced within said gap during the cooling of skin prior to firing an intense pulsed light.

BRIEF DESCRIPTION OF THE DRAWINGS

In the drawings:

FIG. 1 illustrates a side view of various laser units equipped with a diffusing unit, in accordance with the present invention, wherein the delivery system shown in FIG. 1a is an articulated arm, in FIG. 1b is an optical fiber and in FIG. 1c is a conical light guide;

FIG. 3 is a schematic diagram of various configurations of prior art laser units, wherein

FIG. 4 is a schematic diagram illustrating the advantages of employing a diffusing unit of the present invention, wherein

FIG. 5 is a schematic drawing showing the propagation of a laser beam towards a blood vessel, wherein

FIG. 7 illustrates the production of a plurality of microlenses, wherein

FIG. 8 illustrates two types of a diffusing unit, wherein

FIG. 10 illustrates a diffusing unit which utilizes an angular beam expander without a light guide in FIG. 10a and with a light guide in FIG. 10b;

FIG. 12 illustrates a diffusing unit which includes two diffusers, one of which is axially displaceable, wherein FIG. 12a illustrates the unit in an active position and FIG. 12b in an inactive position;

FIG. 14 is another preferred embodiment of the present invention in which a non-scattering diverging unit is used to diverge an input laser beam, wherein

FIG. 15 is a schematic diagram of various means of cooling skin during laser-assisted cosmetic surgery, wherein

FIG. 17 schematic drawing of a flashing device, wherein

FIG. 31 schematically illustrates another embodiment of the invention which employs both an intense pulsed light source and a radio frequency source, for improved coagulation of blood vessels.

DETAILED DESCRIPTION OF PREFERRED EMBODIMENTS

Figure 2A:
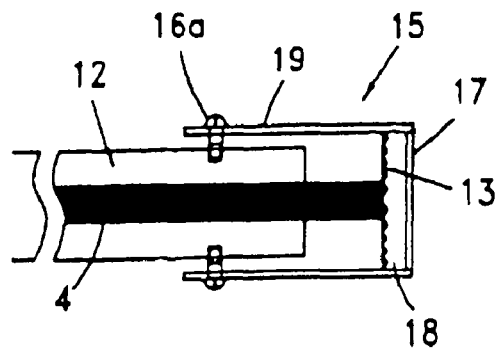
FIG. 2 illustrates a side view of the distal end of a laser unit, showing how the diffusing unit is attached thereto, wherein the diffusing unit is externally attached to the guide tube in FIG. 2a, is attached to a pointer in FIG. 2b, is releasably attached to the guide tube in FIG. 2c, is integrally formed together with the guide tube in FIG. 2d and is displaceable in FIG. 2e whereby at one position the exit beam propagates therethrough and at a second position the exit beam does not propagate therethrough.
Figure 2B:
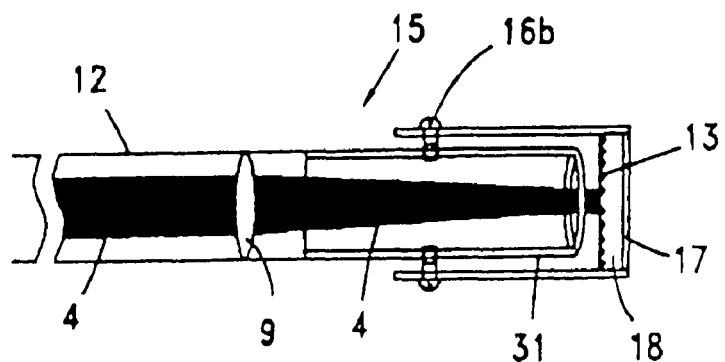
Figure 2C:
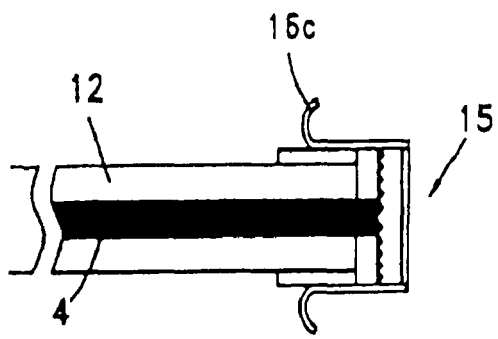
Figure 2D:
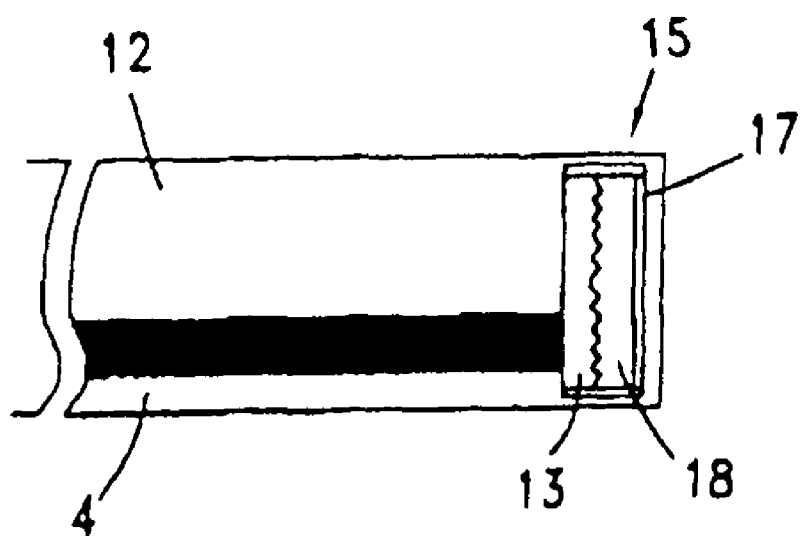

FIG. 1a illustrates a high-intensity laser unit, generally designated by 10, which is suitable for use with the present invention. Laser unit 10 operates at a wavelength ranging between 300 and 1600 nm or between 1750 nm and 11.5 microns, either pulsed, with a pulse duration of 1 nanosecond to 1500 milliseconds and an energy density of 0.01.200 J/cm$^2$, or continuous working with a power density higher than 1 W/cm$^2$. Laser unit 10 is provided with a diffusing unit, generally designated by 15, which induces the exit beam to be scattered. An exit beam is considered to be scattered according to this embodiment when its average half angle angular divergence is greater than 42 degrees relative to the propagation axis of collimated beam 4. A half angle of 60 degrees corresponds to the half angle generated by an "ideal transmitting diffuser," which herein refers to a diffuser with 100% transmission and is provided with Lambertian angular scattering properties. Such a scattering angle, in accordance with the present invention, allows the light which exits diffusing unit 15 to be safe to the eyes of a bystander, yet is provided with a sufficiently high energy density which is necessary for the clinical efficacy of the laser unit.

Laser unit 10 comprises amplifying medium 1 activated by power supply 2 for increasing the intensity of a light beam and two parallel mirrors 3 that provide feedback of the amplified beam into the amplifying medium, thereby generating a coherent beam of ultrapure frequency. The laser unit emits a coherent beam 4 which propagates through a delivery system 5 to distal end 6. The delivery system depicted in FIG. 1a is articulated arm 7a. Diffusing unit 15 is fixedly attached to the distal end of guidance tube 12 by attachment means 16, which may be a set of screws or by bonding or other means known to those skilled in the art, thereby inducing non coherent randomly scattered beam 14 associated with a narrow spectral bandwidth that does not present any risk of damage to bodily tissue if the laser is inadvertently directed to an incorrect target. The diffusing unit includes a passive refractive element that preserves the wavelength of coherent beam 4, as well as its narrow bandwidth, which is generally less than one Angstrom.

In one preferred embodiment of the invention, diffusing unit 15 is preferably cylindrical or rectangular, although any other geometrical shape is equally suitable, and comprises diffusively transmitting element 13, which is proximate to distal end 6 of the laser unit and clear transmitting element 17. Both diffusively transmitting element 13 and clear transmitting element 17 have the same dimensions and are bonded to diffusing unit 15. Diffusively transmitting element 13 and clear transmitting element 17 are preferably separated by narrow gap 18. Due to the existence of gap 18, the laser beam will remain scattered even if clear transmitting element 17 shatters, thereby preserving the inherent safety of a laser unit that incorporates the present invention. The width of gap 18 is as small as possible, usually 0.1 mm. However, diffusing unit 15 may be adapted to a configuration in which diffusively transmitting element 13 contacts clear transmitting element 17. Alternatively, diffusing unit may be provided without a clear transmitting element, whereby the frosted surface of diffusively transmitting element 13 faces the laser unit and its smooth surface faces the tissue.

Scattering is achieved by means of minute irregularities of a non-uniform diameter formed on the substrate of diffusively transmitting element 13. Diffusively transmitting element 13 is preferably produced from thin sand blasted or chemically etched glass, e.g. having a thickness from 0.1 to 0.2 mm, or a thin sheet of non-absorbing light diffusing polymer, e.g. having a thickness of less than 50 microns, such as light diffusing polycarbonate, Mylar or acrylic.

A diffusively transmitting element may also be produced by using a large angle holographic diffuser such as one produced by Physical Optics Corporation (PCO), USA, and is placed adjacent to an additional diffuser. A holographic diffuser illustrated in FIG. 11 induces a scattering half angle, for example, of at least 40 degrees and the second diffuser additionally induces the scattering so as to attain a scattering half angle of e.g. 60 degrees.

Figure 9A:
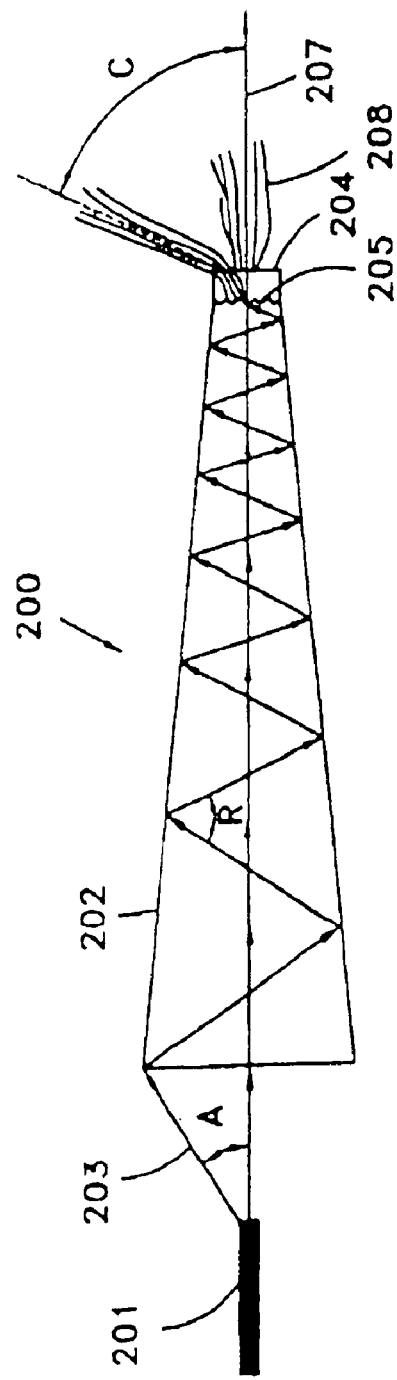
FIG. 9 illustrates a diffusing unit which employs a tapered light guide, such that the light guide receives monochromatic light from an optical fiber in FIG. 9a and from an array of microlenses in FIG. 9b.
Figure 9B:
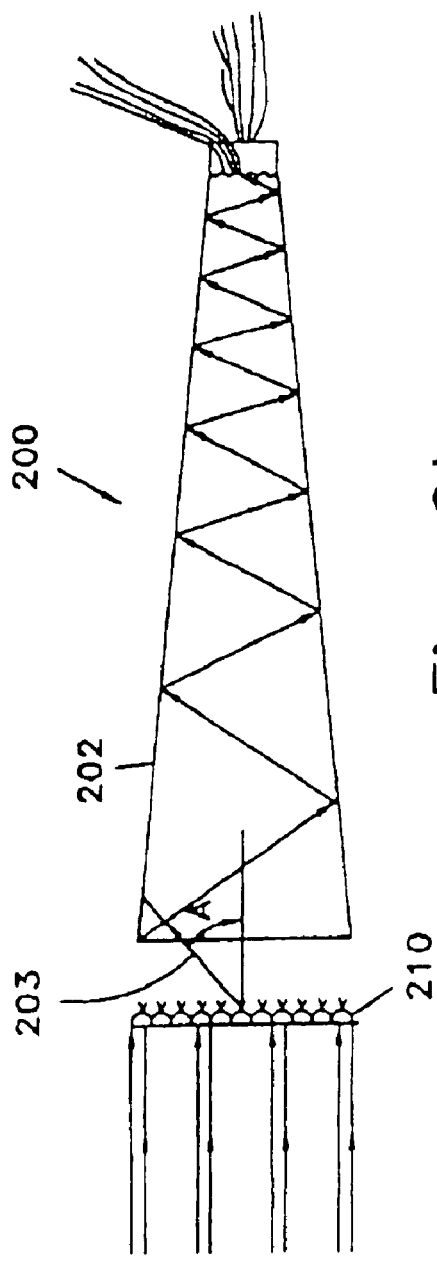

A diffuser which approaches an ideal transmitting diffuser and induces a scattering half angle of 60 degrees and a scattering solid angle of 3.14 sr may be produced from material such as acrylic or polycarbonate by pressing the material against an appropriate surface provided with a very dense array of Frensnel microlenses, such as those produced by Fresnel Technologies Inc., USA, or by placing arrays of microlenses surfaces separated from a light guide as depicted in FIG. 9b.

Similarly diffusively transmitting element 13 may be produced from light diffusing paper such as transparent "Pergament" drawing paper, and may also be produced from other materials such as ZnSe, BaF$_2$, and NaCl, depending on the application and the type of laser used. Both faces of clear transmitting element 17 are essentially planar and smooth. Clear transmitting element 17, which is capable of withstanding the thermal stress imposed by a scattered laser beam, is transparent and made from sapphire, glass, a polymer such as polycarbonate or acrylic, and may be produced from other materials as well, such as ZnF$_2$.

Diffusively transmitting element 13 may be chilled so that it will be capable of withstanding the high power densities which are necessary for attaining clinical efficacy.

As depicted in FIG. 1b, the delivery system may also be optical fiber 7b into which laser beam 4 is focused. Diffusing unit 15 is mounted on guidance tube 8, which directs the beam exiting the distal end of optical fiber 7b by attachment means 16. Furthermore, as depicted in FIG. 1c, the laser unit may be comprised of array 11 of miniature lasers, such as those provided with high power diode lasers, e.g. the Lightsheer produced by Coherent, USA, for hair removal. The beam delivery system for this configuration is preferably conical reflector 7c. In this configuration, diffusing unit 15 is fixed to distal end 6 of light guide 7c and transforms a high-risk beam into randomly scattered beam 14.

FIG. 2 illustrates various methods by which diffusing unit 15 is attached to a laser unit. In FIG. 2a, bracket 19 which supports diffusing unit 15 is attached to guidance tube 12 of an existing laser unit, such as one in use in a clinic, by attachment means 16a, which may be a set of screws or by bonding. As shown in FIG. 2b the laser unit is provided with pointer 31, or any other equivalent subdiffusing unit which enables the user to direct beam 4 to a desired target on the skin, by the focal length and beam diameter which are dictated by lens 9 mounted within guidance tube 12. In this alternative, diffusing unit 15 may be externally attached to guidance tube 12, or may be attached to pointer 19. In FIG. 2c, diffusing unit 15 is attached to Velcro tape 16c, or another type of adhesive tape. This type of attachment means is sufficient for temporary usage. In FIG. 2d, diffusing unit 15 is integrally formed together with guidance tube 12 during manufacturing, internal to the outer wall thereof. FIG. 2e illustrates a releasable attachment means, whereby in one position of a displaceable diffusing unit the exit beam is coherent, not propagating through a diffusively transmitting element, and in a second position in which diffusing unit 15 is attached to guidance tube 12, the exit beam is noncoherent and propagates through a diffusively transmitting element.

Figure 3B:
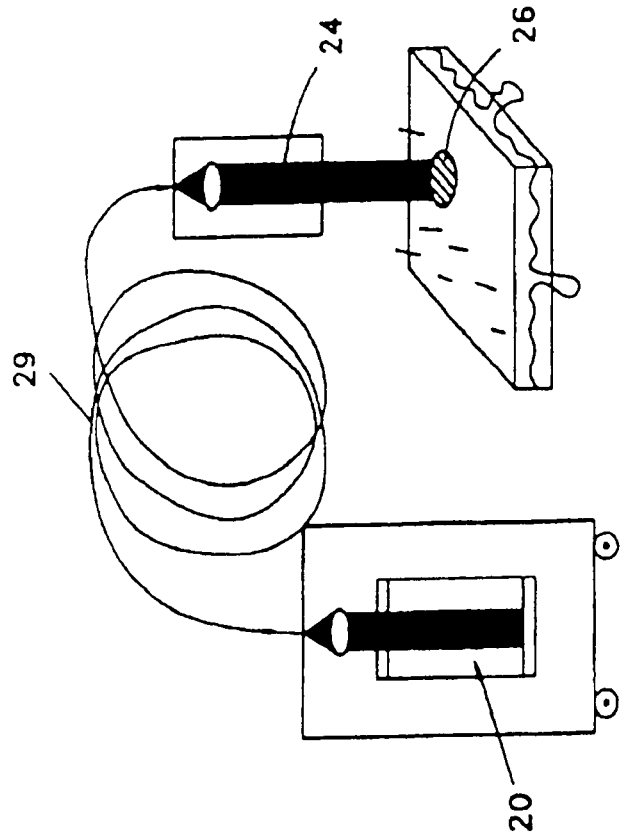
FIG. 3b shows a non-scattered beam directed by an optical fiber to a target.
Figure 3A:
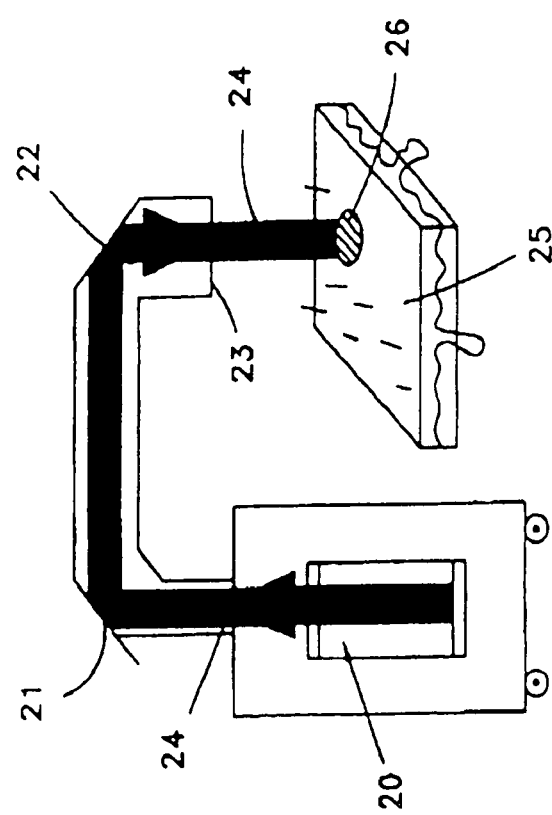
FIG. 3a shows a non-scattered beam directed by reflectors to a target.
Figures 3C, 3D:
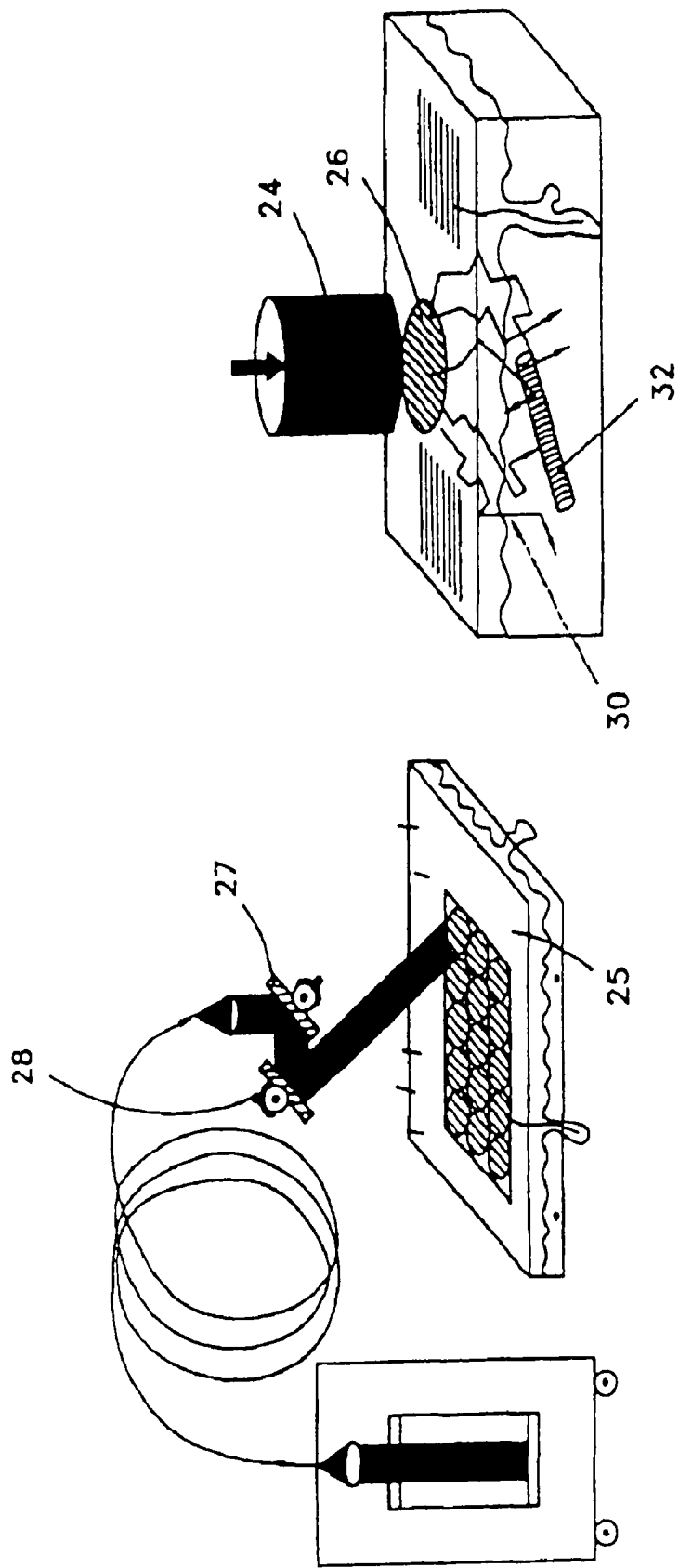
FIG. 3c illustrates prior art surgery performed with a laser beam and scanner.
FIG. 3d shows the propagation of prior art refracted laser beams towards a blood vessel.
Figure 3F:
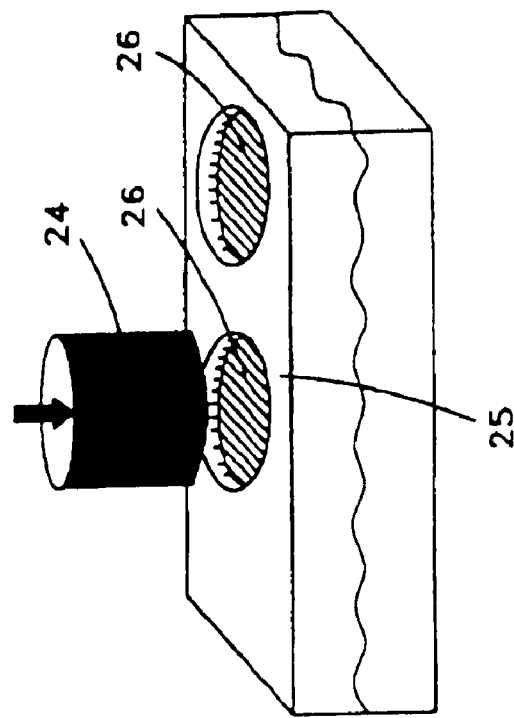
FIG. 3f shows the formation of a crater in tissue by an ablative beam.
Figure 3E:
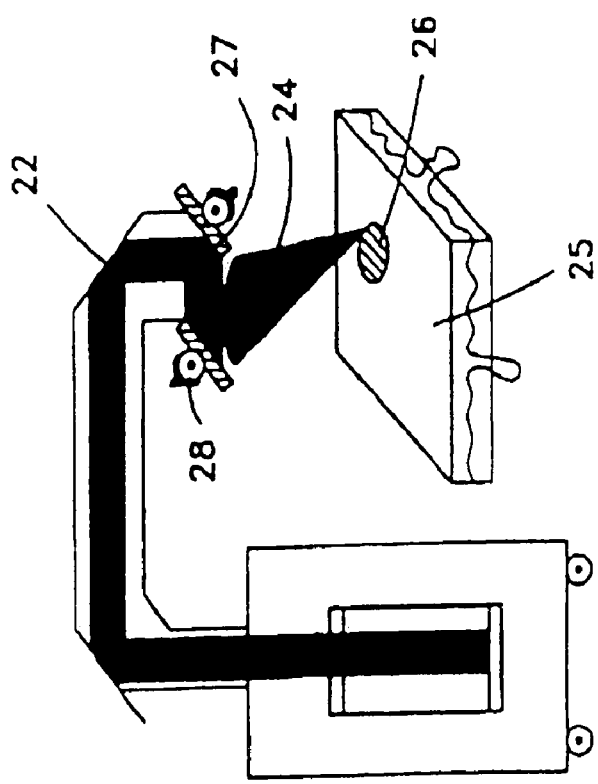
FIG. 3e shows an ablative laser beam focused on tissue in conjunction with a scanner.
Figure 4A:
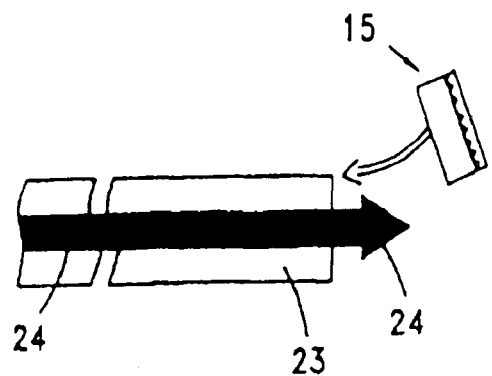
FIG. 4a shows the relative location of the diffusing unit.
Figure 4B:
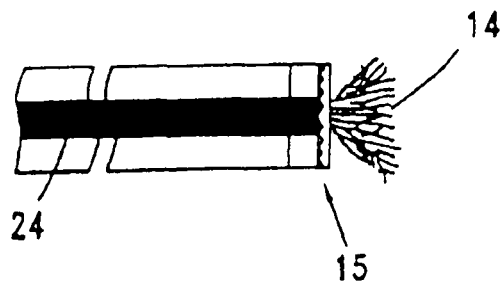
FIG. 4b shows that a collimated laser beam is transformed into a randomly scattered beam.
Figure 4C:
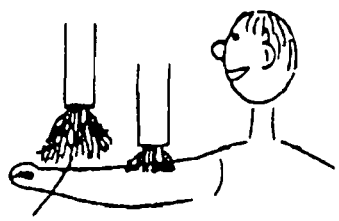
FIG. 4c shows that a scattered beam reduces risk of injury to the skin and FIG. 4d shows that a collimated laser beam reduces risk of injury to the eyes.
Figure 4D:
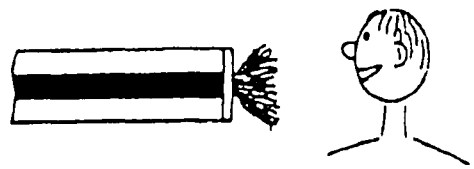

In prior art cosmetic laser surgery, as shown in FIG. 3a, laser unit 20 emits a non-scattered coherent beam 24 from distal end 23 via reflectors 21, 22, by optical fiber 29 in FIG. 3b, or alternatively by deflectors 27 as shown in FIG. 3c, to site 26 that is to be treated within tissue 25. Following the surgery, a well-defined spot is generally produced having a size of up to 20 mm, depending on the specific application and device. Furthermore, beam 24 may be directed by means of motor 28 as shown in FIG. 3c in those situations in which extensive surgery is desired and tissue 25 needs to be scanned. When the wavelength ranges from 310-1600 nm, i.e. ultraviolet and near-infrared, the beam is scattered into individual rays 30, as shown in FIG. 3d, while propagating to blood vessel 32 from site 26. Blood vessel 32 is presented as an example and could be replaced by a hair follicle or any type of skin lesion. At wavelengths ranging from 1750 nm to 11.5 microns, i.e. far infrared, lasers are often used in focused pin-point ablation, that is, having a diameter ranging from 50-200 microns at a shallow depth of 20-150 microns, of epidermal or papillary dermal tissue in conjunction with a scanner, as shown in FIG. 3e. The lasers are used mainly for ablation of tissue, the formation of a crater shown in FIG. 3f. Laser 20, which is capable of effecting the desired surgery at a large distance between distal end 23 and target site 26 for the various applications shown in FIGS. 3a-d, nevertheless can cause severe damage if the beam is not properly aimed.

In contrast, the present invention, which is schematically depicted in FIG. 4, presents a much lower risk to the patient and to observers. As shown in FIG. 4a, diffusing unit 15 is attached to distal end 23 of the laser unit. Diffusing unit 15 transforms the coherent, usually collimated laser beam 24 into homogeneous, randomly scattered beam 14 shown in FIG. 4b. As a result beam 14 significantly reduces risk of injury to the skin as shown in FIG. 4c or to the eyes as shown in FIG. 4d since a collimated beam is not directed to these parts of the body. At very short distances of less than one tenth of the diameter of beam 24 from distal end 23, beam 24 has not begun to completely scatter and increase its diameter and is therefore efficacious as a means for performing cosmetic surgery as shown in FIG. 4c, although an increase in the laser power level may sometimes be needed to compensate for reverse reflections from the diffusing unit into the laser unit. Compensation, in terms of an increase in the needed power level for the laser unit, for reverse reflections is usually be close to 16% due to four air-glass interfaces with 4% Fresnel reflection, and at times may attain 50%. An anti-reflection coating may be used to reduce reflection. For laser units which operate at approximately 10-20% of their maximum energy capacity, it is possible to place the exit plane of the diffusing unit, whether a frosted or clear transmitting element, at a distance from the skin corresponding to approximately 50% of the exit beam diameter.

Figure 5B:
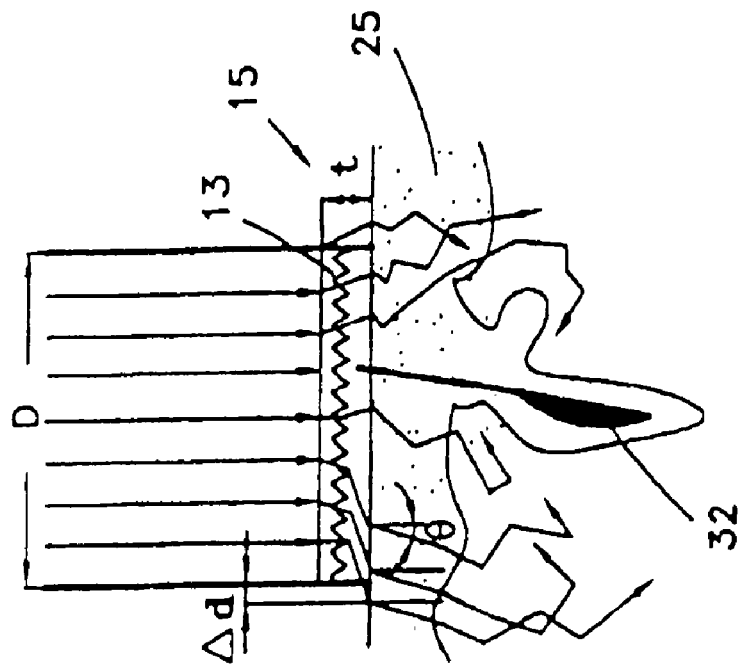
FIG. 5b shows the propagation of a scattered laser beam towards a blood vessel.
Figure 5A:
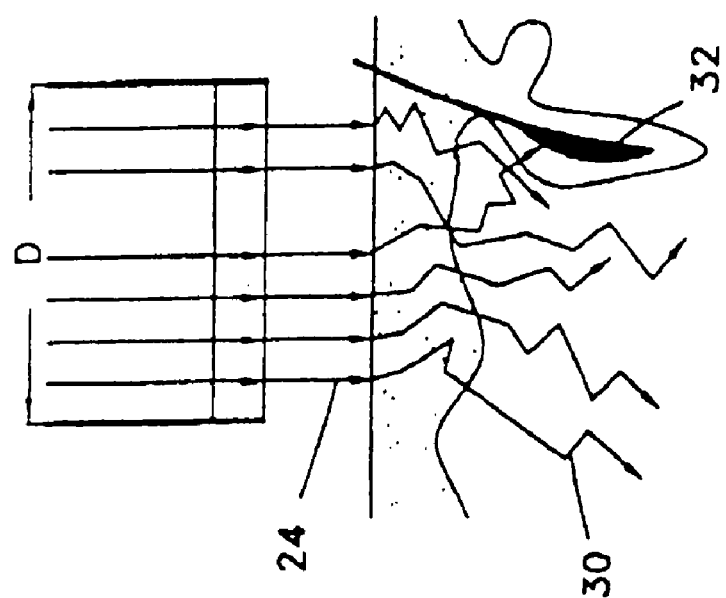
FIG. 5a shows the propagation of an unscattered laser beam towards a blood vessel.

FIG. 5 demonstrates the advantages of the present invention. FIG. 5a illustrates conventional coherent laser beam 24 at a wavelength of 308 to 1600 nm. The collimated beam contacts tissue 25 at a diameter of D before being scattered into individual rays 30 during propagation to target destination 32. FIG. 5b illustrates the result of attaching diffusing unit 15 to the laser unit. When diffusing unit 15 is disposed at a small distance from the tissue surface, the diameter of the scattered beam which contacts tissue 25 is increased by a negligible value of $\Delta d$, assuming uniform scattering, in comparison with the original beam diameter of D. If the thickness t of diffusing unit 15 is less than one-tenth of original beam diameter D, there will be a loss of less than 20 percent in the original beam energy density. Also, the refraction angle $\theta$, corresponding to an index of refraction of 1.5 for keratin, into the tissue relative to collimated beam 24, when a gap exists between diffusively transmitting element 13 and clear transmitting element 17, will never exceed the critical angle of 42 degrees. At a refraction angle less than this critical value, possible additional scattering in tissue is minimized. Consequently light intensity within the tissue is preserved, therefore generally retaining the clinical efficacy, i.e. the ability to perform a surgical or cosmetic procedure, of the laser unit.

Figures 5C, 5D, 5E:
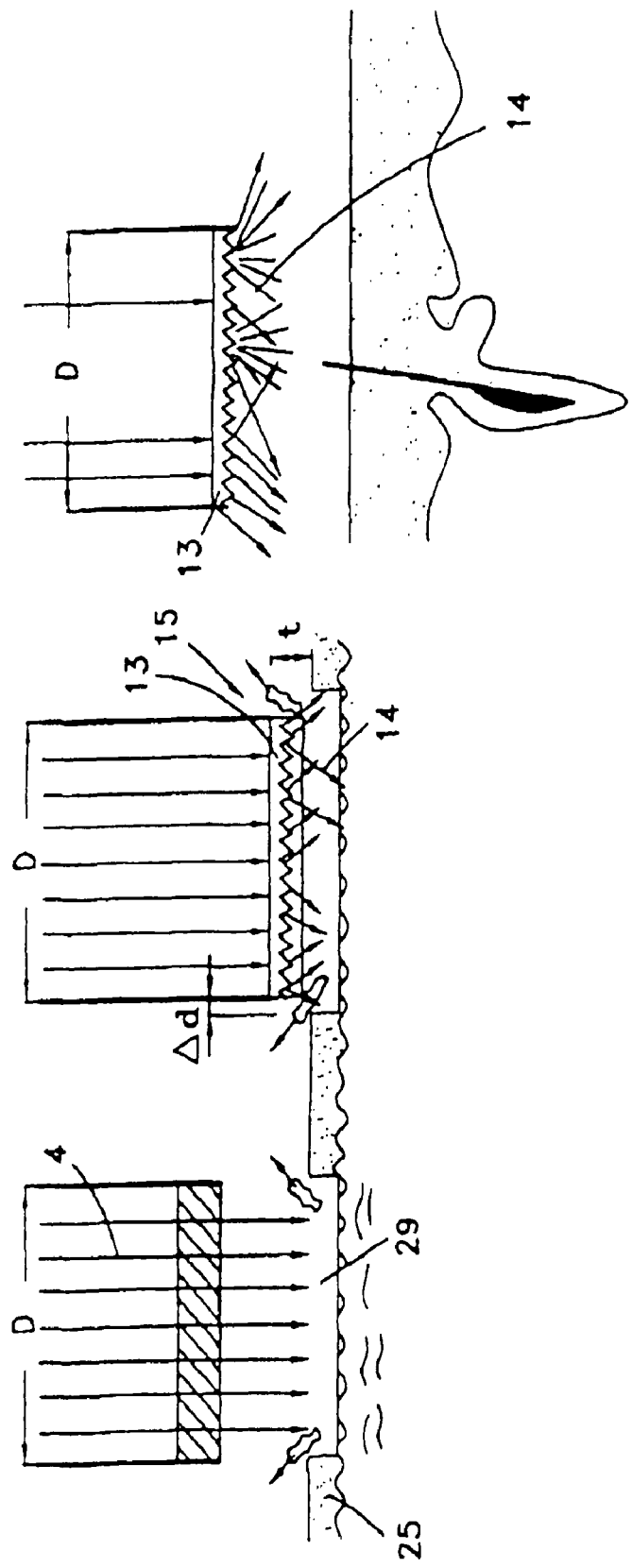
FIG. 5c illustrates the formation of an ablation by means of an unscattered laser beam.
FIG. 5d illustrates the formation of an ablation by means of an scattered laser beam in accordance with the present invention.
FIG. 5e illustrates the scattering of a laser beam distant from a blood vessel.

Just as superficial ablation 29 is formed in tissue 25 as a result of a high energy density beam in the 1.8 to 11.5 micrometer spectral range as shown in FIG. 5c, a similar ablation may be formed in tissue 25 with the use of diffusing unit 15, with the addition of $\Delta d$, as shown in FIG. 5d. A thin spacer (not shown) may be advantageously added in order to evacuate vapors or smoke that has been produced during the vaporization process. Such a spacer is e.g. U-shaped in vertical cross-transmission element, to allow for contact with a target at its lateral ends and for vapor evacuation along the gap formed by its central open region. For surgical procedures with which a very fast ablation rate is needed, e.g. 1 $cm^3$/sec for a skin thickness of 0.1 cm, the spacer is necessarily relatively thick and the gap between the ablated tissue and the diffusing unit is relatively large, e.g. approximately 20-30 mm.

When an excessive amount of smoke is produced and the exit beam becomes diffracted before impinging on the tissue, it may be necessary to add a relay optics device (not shown), which regenerates the degraded exit beam between the diffusing unit and the tissue. An optical regenerator is provided with an internal coating, such that a new and stronger beam with the same characteristics as the degraded beam is produced when the coating emits light energy when stimulated by the incoming photons of the degraded beam. Cylindrical or conical tubes internally coated with gold with an inlet diameter equal to the exit diameter of the diffusing unit are exemplary optical regenerators for this application. A small smoke evacuation port is preferably drilled in the wall of the tube.

When a long-wavelength laser, which does not focus on an eye retina and ranges from approximately 1345 nm to 10.6 microns, is employed, an diffusing unit may not be needed. To scatter the exit beam, an element may be externally attached to a surface which is in contact with the skin during a cosmetic or surgical procedure, so that the exit beam will diverge to a large extent and ensure eye safety from a distance of a few cm from a target, while the energy density is sufficiently high enough to allow for clinical efficacy. For example, a miniature 0.21 Joule/pulse Erbium laser, which produces a spot size of 1 $mm^2$ and generates an energy density of 2.1 $J/cm^2$, greater than the threshold for tissue ablation, will be safe to the eyes from a distance of 10 cm from a target if the beam has a divergence half angle of 45 degrees.

While the laser is an effective surgical tool when the diffusing unit is very close to the tissue surface, safety is ensured after the diffusing unit is repositioned so that it is disposed at a distance of a few millimeters, depending on the laser energy, from the tissue surface. As shown in FIG. 5e, the energy density of scattered beam 14 which impinges upon the surface of tissue 25 is much less than the energy density which results when the diffusing unit is proximate to the tissue surface.

The diffusing unit is adapted to induce random scattering despite any adverse external conditions encountered during the surgical procedure.

Figure 6A:
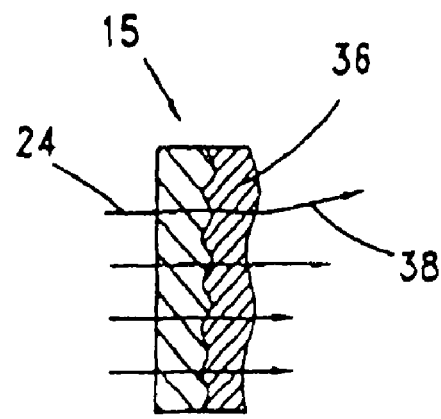
FIG. 6a is a schematic drawing showing the accumulation of liquid residue on a diffusively transmitting element and FIG. 6b is a schematic drawing in which a diffusively transmitting element is shown to be mounted within a hermetically sealed diffusing unit.

The most likely cause of a potential change in rate of scattering of the laser beam passing through diffusing unit 15 results from contact with tissue. Following a surgical procedure in which the diffusing unit contacts tissue, liquid residue 36, such as sebum, water and cooling gel, as shown in FIG. 6a, may accumulate on diffusively transmitting element 13. The refractive index of liquid residue 36 may be such that, in combination with the refractive index of diffusively transmitting element 13, refracted beam 38 approaches the pattern of collimated beam 24 that impinges on the diffusing unit.

Figure 6B:
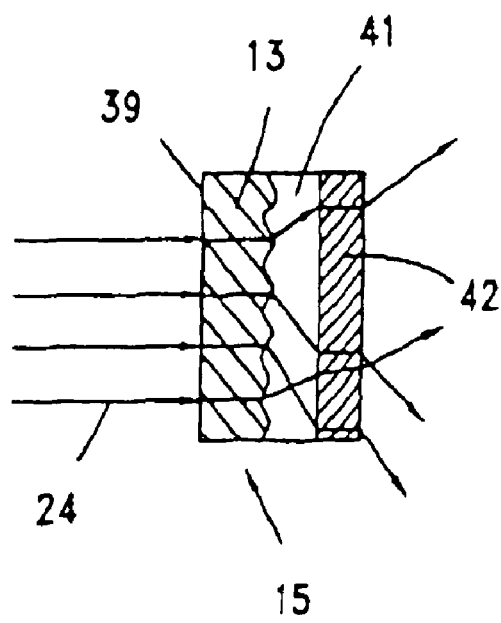
Figure 7A:
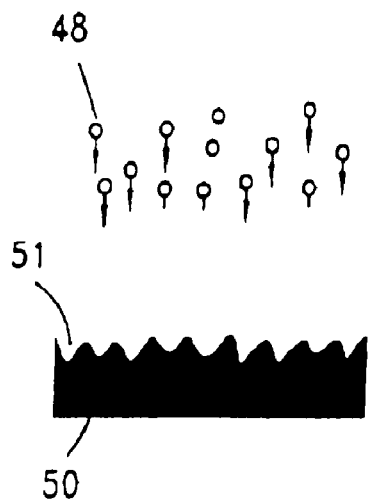
FIG. 7a illustrates the sandblasting of a metallic plate.
Figure 7B:
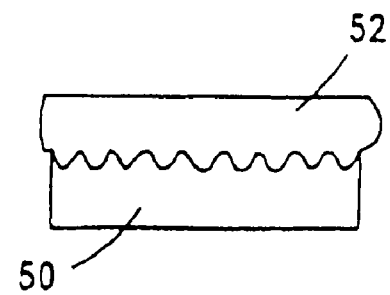
FIG. 7b illustrates the addition of a liquid sensitive to ultraviolet light.
Figure 7D:
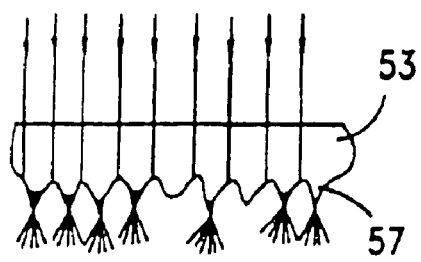
FIG. 7c illustrates the removal of the metallic plate and FIG. 7d illustrates the generation of a scattered laser beam through the microlenses.
Figure 7C:
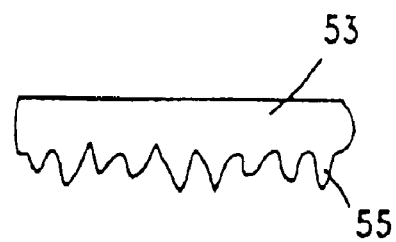

To minimize the risk of injury which may exist if the refracted beam is nearly collitated, diffusively transmitting element 13 is mounted within diffusing unit 15, which is preferably hermetically sealed with sealing element 39 as shown in FIG. 6b, to prevent the accumulation of liquid residue on the former. Clear transmitting element 42 is attached to the distal end of diffusing unit 15 by adhesion and by means of a spacer (not shown), and is separated from diffusively transmitting element 13 by air gap 41. Clear transmitting element 42 and diffusively transmitting element 13 are mutually parallel, and both are perpendicular to the longitudinal axis of diffusing unit 15. When the air gap is less than a predetermined value, a corresponding increase in beam diameter due to scattering is limited, thereby ensuring a minimal effectiveness of the radiation carried by the laser beam for clinical applications. It would be appreciated that accumulation of liquid residue on clear transmitting element 42 will not compromise the inherent safety of a laser unit equipped with a diffusing unit. Since scattering occurs at diffusively transmitting element 13, and the combined index of refraction of air gap 41, clear transmitting element 42 and liquid residue is not sufficient to cause the scattered beam to be once again collimated, the inherent safety of the laser unit is preserved. The accumulation of liquid residue will not affect the clinical efficacy of the laser unit since clear transmitting element 42 is held close to a target during a surgical procedure.

An additional advantage resulting from the separation of clear transmitting element 32 from diffusively transmitting element 13 relates to added safety. Even if clear transmitting element 42 is broken, diffusively transmitting element 13 will scatter the laser beam.

A diffusively transmitting element, adapted to achieve diffusing half angles greater than 45 degrees and as close as possible to an ideal transmitting diffuser, which generates a half angle of 60 degrees, may be produced in several ways:

Sandblasting the surface of a plate of glass, sapphire, acrylic or polycarbonate with fine particles having a size ranging from 1 to 200 microns, depending of the wavelength of the laser beam, comprised of, by example, aluminum oxide;

Sandblasting the surface of a mold plate with fine particles having a size ranging from 1 to 200 microns, depending on the wavelength of the laser beam, comprised of, by example, aluminum oxide and reproducing the contour of the newly formed mold plate surface by pressing hot acrylic, or other suitable material thereon;

Etching the surface of a glass or sapphire plate by chemical means, such as with hydrogen fluoride;

Etching the surface of a glass plate with a scanned focused $CO_2$ laser beam;

Applying a thin sheet of light-diffusing polymer, such as a polycarbonate sheet, a light diffusing acrylic plate, Mylar high quality wax paper or graphical "Pergament Paper" to a glass plate;

Generating a diffraction pattern on the surface of a glass or on a sheet of acrylic or polycarbonate by means of a holographic process to thereby control the divergence angle through the diffraction pattern, which is preferably as large as a half angle of at least 40-45;

Providing a randomly distributed array of thin fibers, arranged e.g. in the form of a conical fiber bundle light concentrator, such as that produced by Schott, Germany, whose aperture is provided with an exit half angle of greater than 40 degrees.

FIG. 7 illustrates the scattering effect that is achieved by sandblasting. As shown in FIG. 7a, metallic plate 50 is bombarded with aluminum oxide particles 48, thereby creating a random distribution of craters 51, each of which having a different size. Liquid 52, which is sensitive to ultraviolet light, is spilled on metallic plate 50 in FIG. 7b and polymerized by ultraviolet radiation. After removal of plate 50, for reuse in the next production batch, transparent frosted plate 53 is produced, as shown in FIG. 7c covered on one side with a random distribution of convex lenses 55 of miniature size. Lenses 55, which have a very short focal length of approximately a few wavelengths, convert a collimated laser beam into a strongly divergent beam with a complete loss of coherence. It is possible to use a similar technique to produce a surface with convex or concave microlenses 57, as shown in FIG. 7d. Microlenses may be produced as well by pressing melted acrylic onto a multimicrolens mold, instead of using a UV curing technique.

Figure 8A:
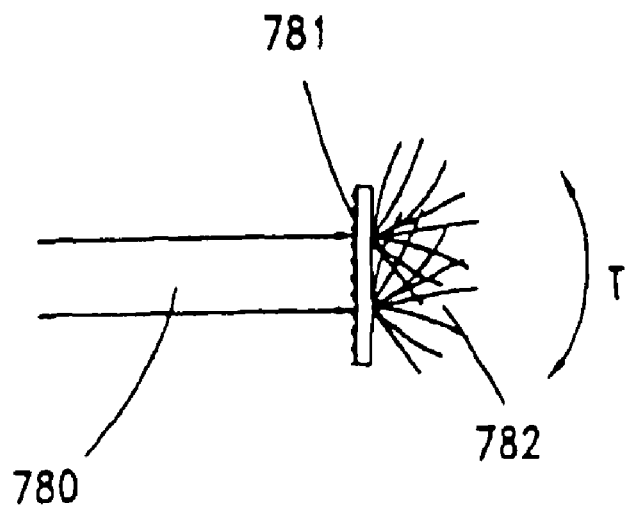
FIG. 8a illustrates one employing a single wide angle diffuser and FIG. 8b illustrates one employing a small angle diffuser.
Figure 8B:
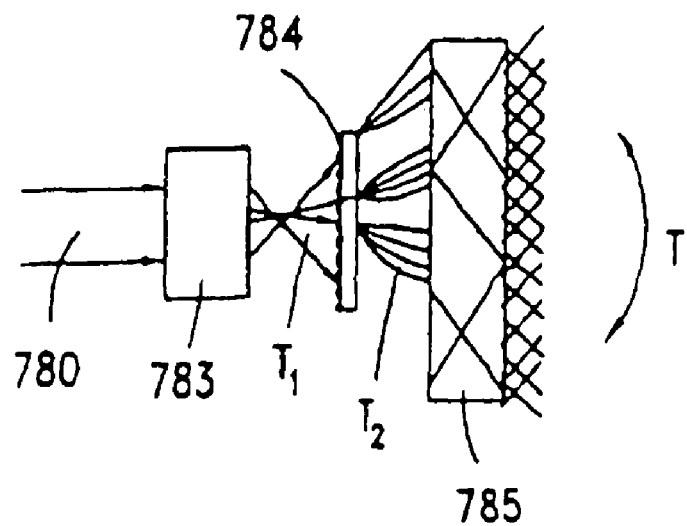

As described above, an exit beam from a laser unit is randomly scattered by a diffusing unit. One type of a diffusing unit is a single wide angle diffuser as shown in FIG. 8a and comprises a diffusively transmitting element 781 which produces scattered light 782 from laser beam 780 having a wide diffusing angle of T. Another type of diffusing unit is shown in FIG. 8b, wherein wide angle diffusion is attained by using divergent optical element 783, and at least one diffuser 784 and refractive/reflective element 785. With this type of diffusing unit, a wide diffusing angle of T is generated in three stages: optical element 783 produces wide angle divergent beam $T_1$ from laser beam 780, diffuser 784 produces a small diffusing angle of $T_2$, and refractive/reflective element 785 expands angle $T_2$ to achieve wide diffusing angle T. Such a multi-component diffusing unit may achieve a wide diffusing angle with the use of elements of high thermal resistance and durability. It will be appreciated that refractive/reflective element 785 may not necessarily be distally disposed with respect to diffuser 784, and may be configured in any other way in order to achieve wide diffusing angle T.

FIG. 9 illustrates another preferred embodiment of a diffusing unit, designated as numeral 200. Diffusing unit 200 is a wide angle diffusing unit, i.e. one that generates a scattering angle that approaches that of an ideal transmitting diffuser, yet is capable of enduring high power laser levels by using glass made of small angle diffusers. Such a diffusing unit is advantageously employed in those applications for which high energy densities are needed for clinical efficacy, and accordingly only a wide-angle scattering angle can ensure eye safety.

As depicted in FIG. 9a, optic fiber 201 is disposed adjacent to the proximate end of tapered light guide 202, such that light rays 203 that exit from fiber 201 with half angle divergence A impinge the inner wall of light guide 202. Rays 203 then are reflected from the inner wall of the light guide at an increasingly smaller reflection angle R. The inner wall is coated with a reflective coating so that reflection angle R will be less than the critical angle for total internal reflection. The tapering angle and the dimensions of the light guide as well as the distance of the fiber from the light guide are selected so that exit half angle C of diffused light 208 which propagates from distal end 204 of the light guide is at least 60 degrees. Also, the distance between fiber 201 and distal end 204 is selected so that the energy density of rays 207 emitted from fiber 202 to distal end 204 without any reflection from the light guide wall will be sufficiently low to be considered eye safe when scattered from small angle diffuser 205, e.g. 10 degrees, which induces a relatively small scattering angle and is proximately placed with respect to distal end 204 of the light guide. A small angle diffuser is advantageously selected due the availability of such diffusers, its high durability and capability to withstand a high energy density, as required for aesthetic and industrial applications. Small angle diffuser 205 increases the divergence of difused light 208, in addition to the divergence generated by tapered light guide 202.

In an exemplary diffusing unit, fiber 201 induces a half angle divergence of 25 degrees, the distance from fiber 201 to light guide 202 is 16 mm, the inner diameter of light guide 202 at its proximate end is 15 mm, the tapering angle of light guide 202 is 3 degrees, and the length of light guide 202 is 142 mm.

Diffusing unit 200 may also include a second light guide (not shown) which receives diffused light 208 from the distal end of light guide 202. This second light guide is sufficiently long so that diffused light 208, which propagates from small angle diffuser 205, will be emitted from the entire surface of the exit plane of the second light guide. The exit plane of the second light guide therefore functions as an extended diffused source. For example, a second light guide having a length of 50 mm and a small angle diffuser which induces a scattering angle of 10 degrees will enable diffused light to span a diameter of greater than 5 mm at the exit of the second light guide.

As shown in FIG. 9b, diffusing unit 200 comprises array of microlenses 210, instead of an optic fiber as in FIG. 8a, which is disposed adjacent to the proximate end of tapered light guide 202. Array 210 is configured such that light rays 203 that exit therefrom with half angle divergence A impinge the inner wall of light guide 202.

FIG. 10 illustrates diffusing unit 700, which comprises another type of angular beam expander, namely one which comprises a set of concave and convex mirrors. Small angle fiber 701 from which light rays 703 exit with a small half angle divergence A, such as 5 degrees, is advantageously employed since diffuser unit 700 provides a high angular amplification.

As shown in FIG. 10a, half angle divergence A is selected so that a light ray 703 impinges on convex mirror 702 and is reflected therefrom to concave mirror 705. A ray 703 is further reflected from mirror 705 at an angle that enables it to impinge upon, and be scattered by, diffusively transmitting element 710, which is affixed to concave mirror 705. In FIG. 10b, diffuser unit 700 is additionally provided with light guide 715. The light which exits from diffusively transmitting element 710 is received by light guide 715 and is reflected within its inner wall, resulting in wide angle diffusing from the entire exit surface of light guide 715. Light guide 715 therefore functions as an ideal extended diffused light source.

Figure 11:
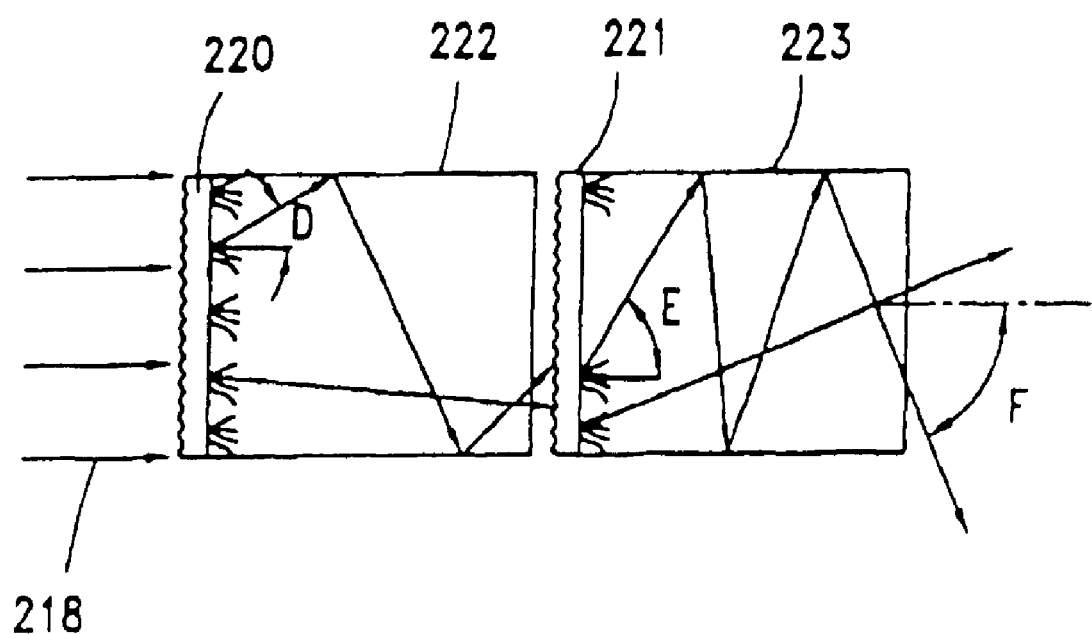
FIG. 11 illustrates a diffusing unit which employs two holographic diffusers, each of which is attached to a corresponding light guide.

FIG. 11 illustrates a diffuser unit in which two 40.45 degrees holographic diffusers 220 and 221 are attached to light guides 222 and 223, respectively. Each holographic diffuser induces a half angle divergence of approximately 45-50 degrees. In order to increase the divergence, two holographic diffusers are used. Light rays 218 propagating from a monochromatic light source are scattered by diffuser 220 to a half angle of D and then are reflected within the inner wall of light guide 222. The scattered light rays are further scattered by diffuser 221 to a half angle of E, are reflected within light guide 223, and exit the diffuser unit at a half angle of F, which approaches 60 degree, the value corresponding to an ideal transmitting diffuser. The light guides are chilled so that the holographic diffusers, which are usually made from plastic material, will also be chilled so that they will be able to withstand the high thermal stress imposed by a high power laser beam. Each light guide may be solid or hollow, and may be made from glass, sapphire, a liquid dielectric, or plastic.

FIG. 12 illustrates another preferred embodiment of the invention in which diffuser unit 300 comprises two distinct diffusers 301 and 302, wherein at least one is axially displaceable. FIG. 12a illustrates diffuser unit 300 in an active position, such that diffusers 301 and 302 are essentially in contact with each other. When in an active position, diffusers 301 and 302 act as a singular randomly scattering diffuser, since substantially all of the monochromatic light 305 that impinges on diffuser 301 is transmitted to diffuser 302. Although the energy density needed for performing an efficacious treatment with monochromatic light 305 is minimally affected, a slight increase of the laser energy can compensate for any energy density losses. FIG. 12b illustrates diffuser unit 300 in an inactive position, such that diffusers 301 and 302 are separated from each other by a distance L, which is sufficiently long to ensure that the radiance of the scattered light which exits diffuser 301 and is additionally scattered by diffuser 302 is below a level that is safe to one's eyes.

As shown, diffuser 301 is axially displaceable by means of a plurality of springs 308 that connect diffuser mount 301a to diffuser mount 302a. When lever 315, which is connected to diffuser mount 301a, is depressed springs 308 are compressed and diffuser 301 becomes substantially in contact with diffuser 302, as shown in FIG. 12a. Distal end 317 of handpiece 303 is then brought in contact with a skin location to be treated by monochromatic light 305 having a high energy density and a high radiance. Upon completion of a desired surgical or cosmetic procedure, lever 315 is released and springs 308 are biased to separate diffuser 301 from diffuser 302 by a distance of L, as shown in FIG. 12b, whereby the radiance of the scattered light is below a safe level. It will be appreciated that any other means well known to those skilled in the art for axially displacing one or more of the diffusers may be used.

Figure 13:
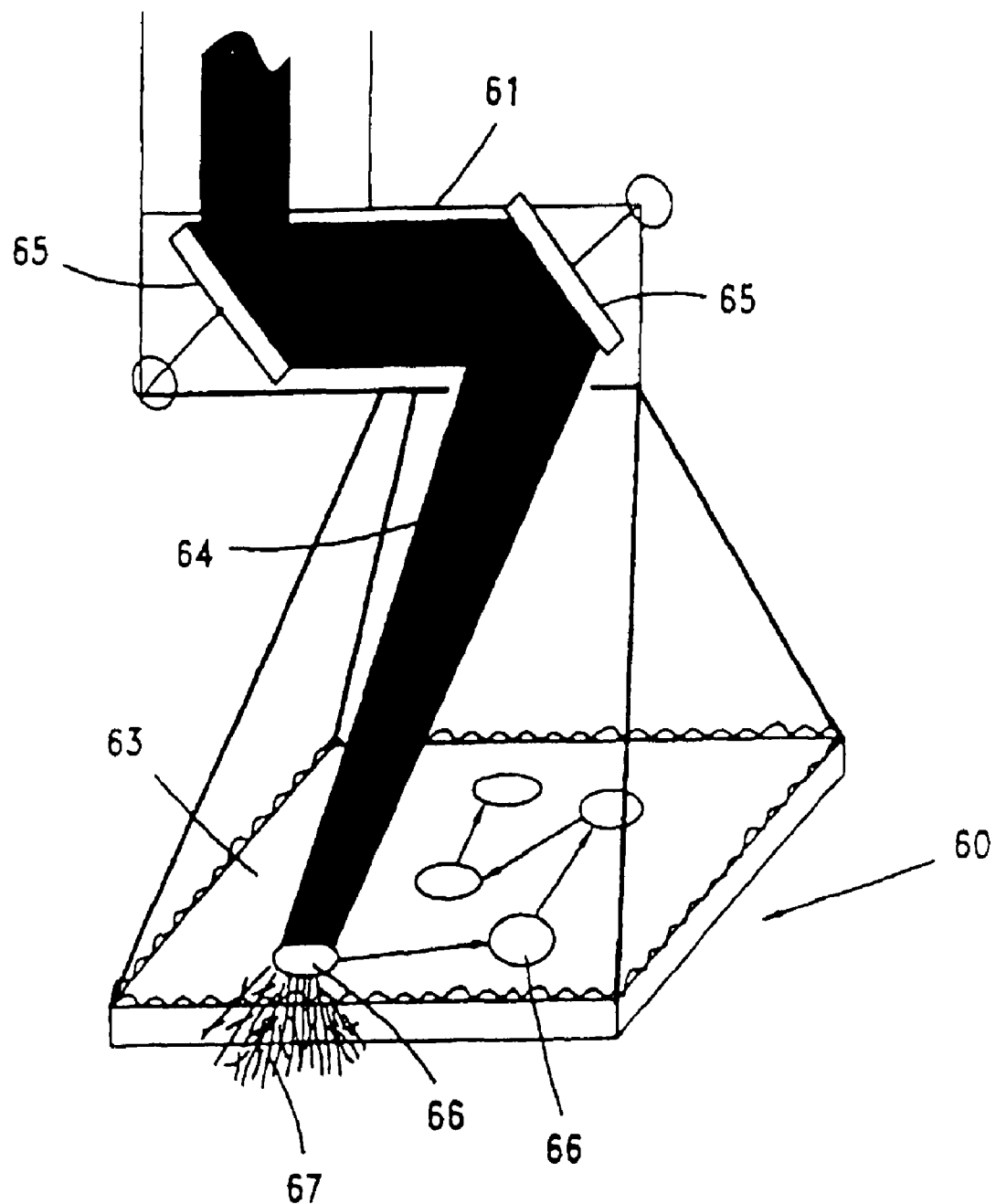
FIG. 13 is a schematic drawing of another preferred embodiment of the present invention in which a scanner rapidly repositions a coherent laser beam onto a plurality of targets on a diffusively transmitting element.

FIG. 13 illustrates an embodiment of the present invention by which tissue, having a larger surface area than the area of the beam impinging thereon, may be treated without overexposure to a laser beam. In prior art systems using a scanner, the treatment beam is quickly displaced in a programmable fashion from one location to another on the tissue to be treated. Although this method provides rapid and reliable treatment, there is a significant risk, however, that the laser beam is liable to be aimed at eyes, skin or flammable materials located in the vicinity of the laser unit.

The diffusing unit generally designated by 60 is shown. In this embodiment the diffusing unit is rigidly attached to delivery system 61, which is provided with a scanner. Diffusively transmitting element 63 is formed with a plurality of visible targets 66 and is placed close to the skin, facing the distal end of delivery system 61. Diffusing unit 60 is preferably provided with a clear transmitting element, as described hereinabove. Coherent collimated or convergent exit beam 64 is directed via a plurality of repositionable reflectors 65 to a predetermined target 66 graphically indicated on diffusively transmitting element 63. The beam that impinges upon a predetermined target 66 is randomly scattered and converted into non-coherent beam 67 whose energy density is essentially similar to that of exit beam 64. Reflectors 65 are controllably repositionable by means of a scanner, whereby they may be displaced from one position and angular disposition to another, so as to accurately direct exit beam 64 to another target 66. The sequence of which target is to receive exit beam 64 after a selected target is programmable and is preferably semi-random to reduce pain which may be felt resulting from the treatment of two adjacent targets, with the time increment between two doses of laser treatment being less that less than a preferred value. A programmable sequence precludes on one hand the chance of a target not to receive an exit beam at all, and on the other hand precludes the chance of not to be inadvertently exposed twice to the exit beam. With the usage of diffusing unit 60, small-diameter beams, e.g. 0.1-7.0 mm, may be advantageously employed to treat a tissue having an area of 16 cm$^2$. Similarly, a scanner may be employed for any other feasible wide-area diffusing unit, such as an array of diffusers/light guides incorporating those units illustrated in FIGS. 9-12, whereby an exit laser beam may be directed to each of the diffusers/light guides. Such an array may consist of 9 diffuser/light guides, each having a 3-mm diameter, to cover an area of 81 mm$^2$. Scanning may also be achieved by laterally moving an angular expander over the diffuser/light guide array.

FIG. 14 illustrates another preferred embodiment of the invention in which a diffusing unit is not used, but rather a diverging optical element is employed to produce an exit beam having radiance, or alternatively, energy density, depending on the wavelength, below a safe level.

Figure 14A:
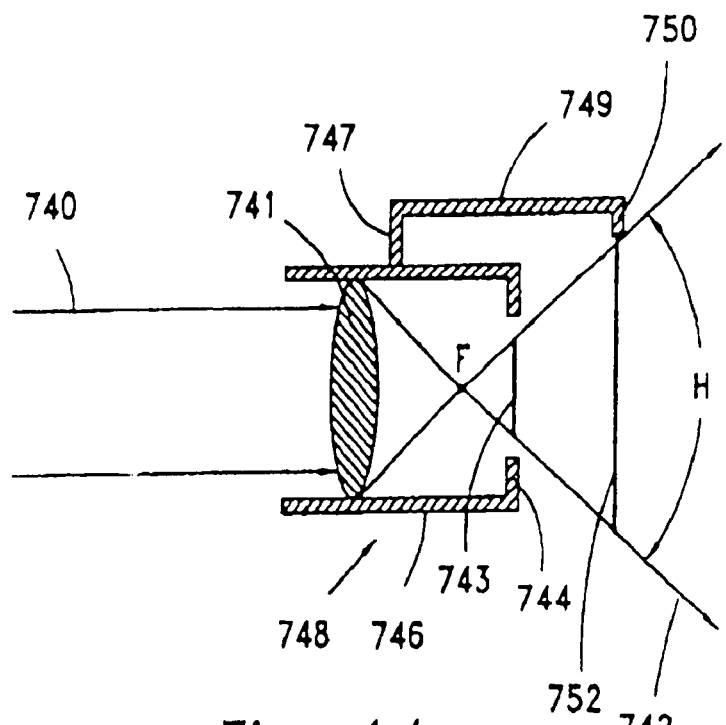
FIG. 14a illustrates a single optical element and FIG. 14b illustrates a plurality of elements.

As shown in FIG. 14*a*, diverging optical element 741 is placed in diverging unit 748, which is attached to the distal end of the laser unit by any means depicted hereinabove in FIG. 2. Divergent element 741, which is provided with a relatively short focal length, focuses input beam 740 at point F. The beam diverges at a point distally located with respect to point F, as well known to those skilled in the art, and produces divergent beam 742 having a divergent angle of H, a cross section 743 at a plane coplanar with distal end 744 of diverging unit 748 and a cross section 752 at a plane coplanar with shield 750. When divergent beam 742 has a cross sectional dimension at least equal to cross section 752, its radiance is less than an eye safe level.

Pulsed laser radiation in the wavelength range of 1400 nm to 13 microns, according to the ANSI Z 136.1 standard, is considered eye safe if the Accessible Energy Limit (AEL) at the ocular plane is less than a value of $0.56*t(¼)$ J/cm$^2$, where t is the pulse duration in seconds. For example, a typical pulse duration ranging from 1 to 100 msec is associated with an AEL ranging from 0.1 to 0.3 J/cm$^2$, respectively. Accordingly, diverging unit 748 is provided with at least one shield 750, each of which prevents one's head from entering a zone of the divergent beam at which the energy density is greater than the AEL. Shield 750 is connected to tube 746 of diverging unit 748 by means of rigid member 747, and cross member 749. The length of cross member 749 and the degree of angular divergence H is selected to ensure that the energy density distal to shield 750 is less than the AEL. Normally, cross member 747 is unyielding to head pressure, thereby ensuring eye safety. However, when a lever is actuated, for example, cross member 747 is opened and a spring (not shown), which is normally in a relaxed state and connected to both rigid member 747 and cross member 749, becomes tensed and allows the shield to be proximately displaced. When shield 750 is proximately displaced, distal end 744 of diverging unit 748 may be in contact with a target skin location and cross section 743 of beam 742 having a sufficiently high energy density for a desired application may be utilized. For example, diverging unit 748** is suitable for those applications by which a laser beam is greatly absorbed by water.

Figure 14B:
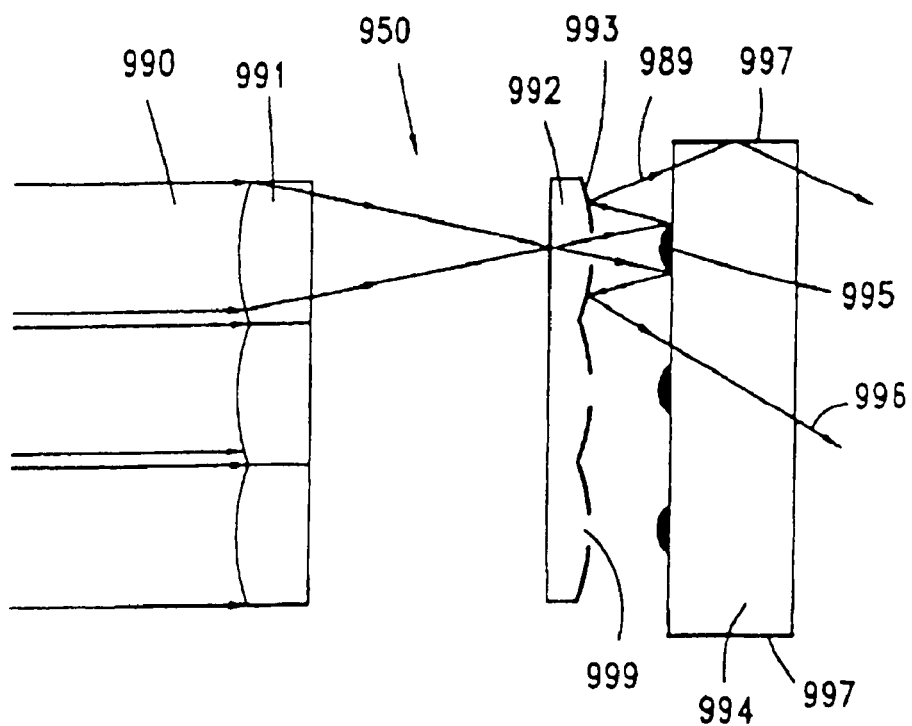

FIG. 14*b* illustrates diverging unit 950, which comprises array 991 of focusing lenslets each of which has a diameter of e.g. 0.7 mm, array 992 of lenses each of which is provided with reflective coating 993 on its distal side, and a plurality of convex reflectors 995 attached to transparent plate 994. Rays 990 from a collimated laser beam are focused by lenslets 991 and transmitted through non-reflective area 999 formed on the distal side of each lens 992. The location of each non-reflective area 999 is selected so that a focused ray propagating therethrough will impinge upon a corresponding reflector 995 at such a reflecting angle such that it will be reflected therefrom and strike a corresponding reflective coating 993, from which it is again reflected and propagates through transparent plate 994. Most rays, such as ray 996 then exit plate 994. However, some rays, such as ray 989, strike a transversal side 997 of plate 994, which is provided with a reflective coating and causes these rays to exit plate 994. Plate 994 accordingly functions as a light guide when transversally reflecting light rays strike a side 997. The length, i.e. the distance between sides 997, of plate 994 is substantially equal to the length of array 991, and therefore the energy density of an input beam is preserved at the exit of plate 994. In order to comply with the requirements of the aforementioned standards, namely to achieve a safe radiance level with a lens having a diameter of 0.7 mm and producing a divergent half angle of 60 degrees, a lenslet 991 with a focal length of 3 mm may be used to achieve a uniform radiance at a solid angle of approximately Π steradians.

The distal end of plate 994 may be etched to further diffuse the divergent light exiting therefrom, so that the distal end may function as an extended diffused light source. If desired, the transparent plate may be substituted by a light guide.

In summation, the present invention incorporates four groups of units which cause a monochromatic light to diverge at a sufficiently wide angle so that the radiance of an exit beam is eye safe:

1) A diverging unit provided with a single diverging optical element;

2) A multi-component diverging unit provided with reflective and refractive optical elements, and without any diffusers;

3) A diffusing unit provided with a single thin diffusively transmitting element; and 4) A multi-component diffusing unit, whereby a wide divergent, diffusing angle is achieved by using a high thermally resistant refractive/reflective optical component, as well as at least one thermally resistant low angle diffuser.

When a multi-component diffusing or diverging unit is employed, a relatively simple eye safety monitoring device can be used. Due to the high thermal durability of the selected multi-component unit, the radiance homogeneity is essentially preserved from the proximate end to the distal end thereof. Consequently, limited sampling of the radiance level is required, and an expensive monitoring device is rendered unnecessary. Another advantage of a multi-component unit is that monochromatic light reflected from the skin returns to the corresponding unit via a light guide with respect to a diffusing unit and via a transparent plate with respect to a diverging unit, preventing an adverse effect to the skin if reflected monochromatic light were to return thereto.

FIG. 15 illustrates another preferred embodiment of the invention in which a diffusing unit is provided with a skin cooling system. Transparent skin cooling devices are often used in conjunction with skin laser treatments. However they do not scatter laser light and do not reduce the risks associated with exposure to a laser beam. FIGS. 13a-d illustrate prior art skin coolers. In FIGS. 15a and 15b transparent lenses or plates 80 are in contact with tissue 79. Cooling liquid 81, which flows through conduit 83, conducts heat from the heated skin to a cooler. Treatment laser beam 82 propagates without being scattered through the cooling device and penetrates the skin. In FIG. 15c gaseous coolant 84 is used. In FIG. 15d, highly conductive plate 86 is in contact with tissue 79 and chilled by thermoelectric cooler 85.

Figure 15A:
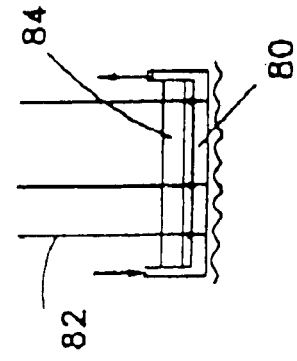
FIGS. 15a-d are prior art means, while FIG. 15e utilizes cooling fluid and FIG. 15f utilizes a thermoelectric cooler.
Figure 15B:
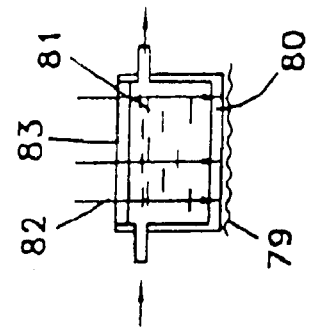
Figure 15C:
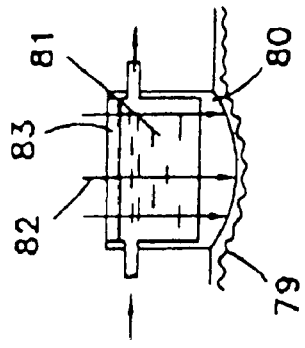
Figure 15D:
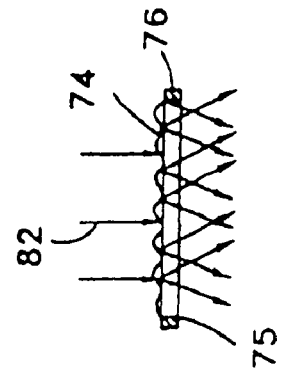
Figure 15E:
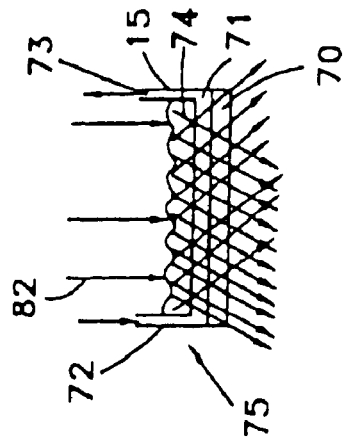
Figure 15F:
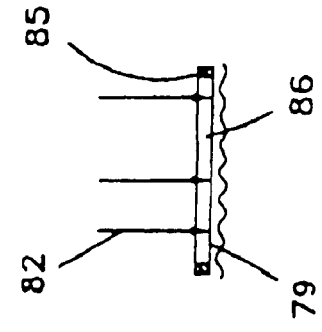

As shown in FIG. 15e, diffusing unit 75 comprises diffusively transmitting element 74, clear transmitting element 70 and conduit 71 formed therebetween. Conduit 71 is filled with a low temperature gas or liquid of approximately 4° C., which enters conduit 71 through opening 72 and exits at opening 73. The cooling fluid preferably flows through a cooler (not shown). Diffusing unit 75 is positioned in contact with the skin, for treatment and cooling thereof. Clear transmitting element 70 is preferably produced from a material with a high thermal conductivity such as sapphire, in order to maximize cooling of the epidermis. Diffusively transmitting element 74 is disposed such that its proximal face is frosted side and its distal face is planar, facing conduit 71. In FIG. 15f, the diffusing unit comprises diffusively transmitting element 74 made from sapphire, which is chilled at its lateral sides 75 by thermoelectric cooler 76. The proximal side of 74 is frosted and the smooth distal side faces the skin. The parameters of the flowing fluid and of the cooler are similar, by example, to the Cryo 5 skin chiller produced by Zimmer, Calif., USA. It will be appreciated that any of the skin cooling means illustrated in FIGS. 15d-f may be used to cool skin which is heated as a result of the impingement of monochromatic light thereon even though a diffusively transmitting element is not used.

The eye safety when exposed to the exit beam of a diffusing or diverging unit is significantly improved relative to prior art devices.

Parameters for eye safety analysis are presented in "Laser Safety Handbook," Mallow and Chabot, 1978 in which the standard ANSI Z 136.1 is cited. A laser beam which is reflected from a light diffusing surface is categorized as an extended diffused source if it may be viewed at a direct viewing angle A, greater than a minimum angle Amin, with respect to a direction perpendicular to the source of the laser beam. If a reflected beam may not be viewed at angle A, it is categorized as an intrabeam viewing source. Since a reflected beam is more collimated when viewed at a distance, viewing conditions are intrabeam if the distance R from the source of the laser is greater than a distance Rmax.

Another significant parameter is the maximum permitted radiance, normally referred to as Accessible Energy Limit (AEL) while staring at a diffusing surface which completely reflects a laser beam. AEL depends on the energy density, exposure duration, and wavelength of the laser beam, as well as the solid angle into which the laser beam is diffused. The safety level of a laser unit is evaluated by comparing the AEL to the actual radiance (AR) of the laser beam. Staring at the exit of a diffusing unit according to the present invention is equivalent to staring at a reflecting extended diffuser with 100% reflectivity. The AEL for visible and near infrared radiation exiting a diffusing unit for which protective eyeglasses are unnecessary based on an extended diffuser source is defined by ANSI Z 136.1, as $10*k1*k2*(t^{1/3})$ J/cm$^2$/sr, where t is in seconds and k1=k2=1 for a wavelength of 400-700 nm, k1=1.25 and k2=1 at 750 nm, k1=1.6 and k2=1 at 810 nm, k1=3 and k2=1 at 940 nm and k1=5 and k2=1 at a wavelength of 1060 to 1400 mm. The safety limit set by ISO 15004: 1997 E for pulsed radiation is 14 J/cm$^2$/sr.

The actual radiance (AR) is the actual energy per cm$^2$ per steradian emitted from a diffusing unit. The ratio between AEL and AR indicates the safety level of the laser unit employing a diffusing unit, according to the present invention. A ratio less than 1 is essentially unsafe. A ratio between 1.0 and 5 is similar to that of high intensity flashlight sources used in professional photography and intense pulsed light sources used in aesthetic treatments, and is much safer than prior art laser sources. Prior art laser sources which do not incorporate a diffusing unit have a ratio which is several orders of magnitudes less than 1.

Table I below presents a comparison in terms of eye safety between the exit beam of monochromatic light after being scattered by a diffusing unit into a solid angle of 3.14 sr, which is equivalent to that attained by an ideal transmitting diffuser, according to the present invention. The parameters for a non-coherent diode-based laser unit are based on one produced by Dornier Germany. The parameters for a non-coherent Alexandrite-based laser unit are based on one produced by Sharplan/ESC (Epitouch). The parameters for a non-coherent Nd:YAG-based laser unit intended for hair removal are based on one produced by Altus, USA. The parameters for a non-coherent Nd:YAG-based laser unit intended for photo-rejuvenation are based on one produced by Cooltouch, USA. The parameters for a non-coherent dye-based laser unit are based on one produced by ICN (Nlight). The parameters for an intense pulsed light laser unit are based on one produced by ESC. The AEL for a particular wavelength and pulse duration is based on the aforementioned ANSI Z 136.1 standard.

TABLE I

| System type | Non coherent Diode based | Non coherent Alexandrite based | Non coherent Nd:YAG based | Non coherent Nd:YAG based | Non coherent Dye based | Intense Pulsed Light | CW Diode 60 degrees diffuser |
|---|---|---|---|---|---|---|---|
| Application Parameters | Hair removal | Hair removal | Hair removal | Photo-rejuvenation | Photo-rejuvenation | Hair removal | Tooth whitening |
| Wavelength | 940 nm | 755 nm | 1064 nm | 1320 nm | 585 nm | 645-900 nm | 980 nm |
| Energy | 6 J | 10 J | 11.3 J | 7 J | 0.6 J | 90 J | 1.5 J |

TABLE I-continued

| System type | Non coherent Diode based | Non coherent Alexandrite based | Non coherent Nd:YAG based | Non coherent Nd:YAG based | Non coherent Dye based | Intense Pulsed Light | CW Diode 60 degrees diffuser |
|---|---|---|---|---|---|---|---|
| Pulse duration | 50 msec | 40 msec | 60 msec | 60 msec | 0.5 msec | 40 msec | 1 sec |
| Spot size | 5 mm | 7 mm | 6 mm | 6 mm | 5 mm | 10 × 30 mm$^2$ | 5 × 5 mm$^2$ |
| Energy density | 30 J/cm$^2$ | 25 J/cm$^2$ | 40 J/cm$^2$ | 25 J/cm$^2$ | 3 J/cm$^2$ | 30 J/cm$^2$ | 6 J/cm$^2$ |
| Extended view parameters | | | | | | | |
| A min | 8 mrad | 3.5 mrad | 4 mrad | 4 mrad | 2.5 mrad | 5 mrad | 15 mrad |
| R max | 0.4 m | 2 m | 2 m | 2 m | 1.3 m | 4 m | 0.33 m |
| Eye safety Parameters | | | | | | | |
| AEL/sr | 11 J/cm$^2$/sr | 4.3 J/cm$^2$/sr | 19.5 J/cm$^2$/sr | 20 J/cm$^2$/sr | 0.79 J/cm$^2$/sr | 3.4 J/cm$^2$/sr | 35 J/cm$^2$/sr |
| AR/sr | 9.6 J/cm$^2$/sr | 8 J/cm$^2$/sr | 12.7 J/cm$^2$/sr | 8 J/cm$^2$/sr | 0.79 J/cm$^2$/sr | 9.5 J/cm$^2$/sr | 8 J/cm$^2$/sr |
| Eye safety Figure of merit AEL/AR | 1.14 | 0.53 | 1.54 | 2.5 | 1 | 0.35 | 4.1 |

The table shows that the exit beam according to the present invention is essentially as eye-safe, or safer than, broad band non-coherent intense pulsed light sources, such as those used for professional photography or those used for cosmetic surgery. The scattered monochromatic light, for most of the light sources, does not necessitate protective eyeglasses and is safer than an accidental glance into the sun for a fraction of a second. Although the ratio for the Alexandrite and Intense Pulsed Light sources is less than 1 and protective eyeglasses must be worn, the required optical attenuation for these light sources is less than 3, much less than the required optical attenuation with the use of a conventional monochromatic light source not provided with a diffusing unit, which is on the order of $10^4 \cdot 10^7$. It will be appreciated that a similar level of eye safety for laser units utilizing a diffusing unit may be achieved with a very wide scattering angle, approaching a half angle of 60 degrees or a solid angle of Π steradians. Small angle scattering may result in a different level of eye safety when operated at an energy density suitable for aesthetic treatments; nevertheless, such a scattered exit beam is much safer than the exit beam of a conventional coherent laser unit.

Figure 16:
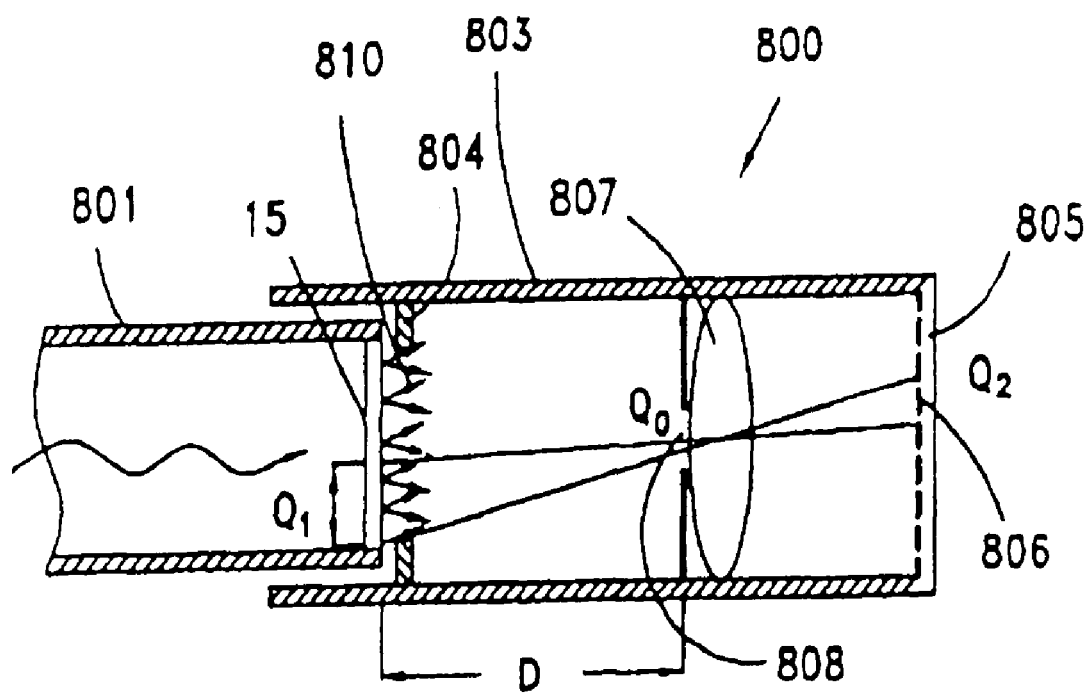
FIG. 16 illustrates an eye safety measurement device.

The radiance of the light emitted by a diffusing unit can be measured to verify that it is in compliance with the appropriate standards for laser eye safety. In one embodiment, a converted laser utilizing a diffusing unit in accordance with the present invention is provided with an eye safety measurement device. Such a device may be an energy meter such as that produced by Ophir, USA or an array of light detectors 805 as depicted in FIG. 16. The eye safety measurement device is provided with control circuitry which is in communication with the operating system of the laser unit, so that, as a result of a mishap, a warning is issued indicating that protective eyeglasses are required if the measured radiance of a scattered laser beam is greater than a predetermined safe value. Alternatively, the control circuitry may discontinue operation of the laser unit if the measured radiance of a scattered laser beam is greater than a predetermined safe value.

FIG. 16 illustrates an exemplary eye safety measurement device, designated as numeral 800. Device 800 is operative to measure the radiance of scattered light 810, which is scattered by means of diffusing unit 15 attached to distal end 809 of laser unit handpiece 801. Device 800 is provided with an array of light detectors 806, e.g. complementary metal oxide semiconductor (CMOS) detectors which provide light imaging, at distal end 805 thereof, on which scattered light 810 impinges after passing through aperture 808 of diameter $Q_0$ and lens 807. After distal end 809 is inserted into a complementary opening formed within device 800 until contacting annular abutment plate 804 perpendicular to outer wall 803 of device 800, the laser unit is fired. For purposes of clarity, light which propagates through segment $Q_1$ of diffusing unit 15 impinges on segment $Q_2$ of detector array 806. The radiance of scattered light 810 therefore is determined by dividing the amount of energy sensed by detectors 806 by diameter $Q_0$ of aperture 808 and by the solid angle characteristic of the detector structure. For example, the distance D between abutment plate 804 and aperture 808 is 200 mm, segment $Q_i$ of the diffusing element 15 is 0.7 mm, and diameter $Q_0$ of the aperture is 7 mm, to comply with the regulations set forth in ANSI Z 136.1.

FIG. 17 illustrates another embodiment of the invention, wherein eye safety in the vicinity of a laser unit that emits an infrared beam or other invisible radiation is increased by adding a flashing device to the laser system to cause one's eyes to blink during the propagation of the laser beam.

Figure 17A:
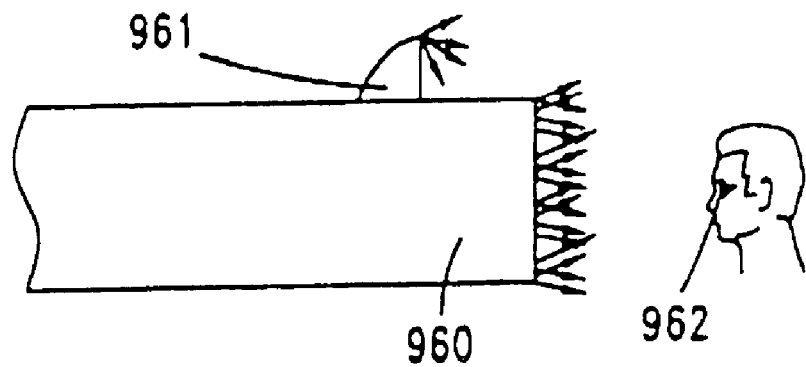
FIG. 17a illustrates one that induces uncontrolled blinking before firing a laser beam.

FIG. 17a illustrates distal end 960 of a laser unit, which emits light 955 generated therefrom, preferably being scattered monochromatic light when a diffusing unit is employed. To prevent damage to eye 962 of a bystander located in the vicinity of the laser unit, flashing device 961 is added to distal end 960. Flashing device 961 generates a short visible light flash a fraction of a second prior to the firing of a laser beam.

Figure 17B:
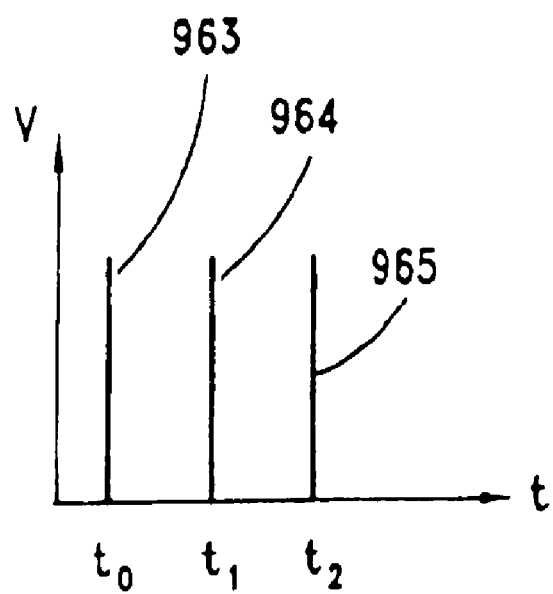
FIG. 17b is a timing diagram corresponding to the flashing device of FIGS. 17a, and 17c illustrates a flashing device that detects a retroreflected beam from an eye within firing range of a laser beam.

As shown in FIG. 17b, activation of the laser unit initiates an electrical pulse 963 at time t$_0$, which triggers a timer circuit (not shown). The timing circuit is adapted to generate and transmit pulse 964 at time t$_1$ to flashing device 961, to produce a flash is sensed by eye 962. Flashing device 961 may be a well known flashing means associated with cameras or may utilize diodes, or any other feasible means to produce an instantaneous flash. After a predetermined period of time, the timing circuit transmits a pulse to the control system of the laser unit to fire a laser beam at time t$_2$. This predetermined period of time, namely the difference between t$_2$ and t$_1$, is approximately 0.25 seconds, equal to the reaction time of uncontrolled blinking as a response to light, and is preferably no more than 0.20 seconds. A flashing device 961 may be added to any source of monochromatic light, such as any type of laser or IPL sources, whether producing visible or invisible light.

Figure 17C:
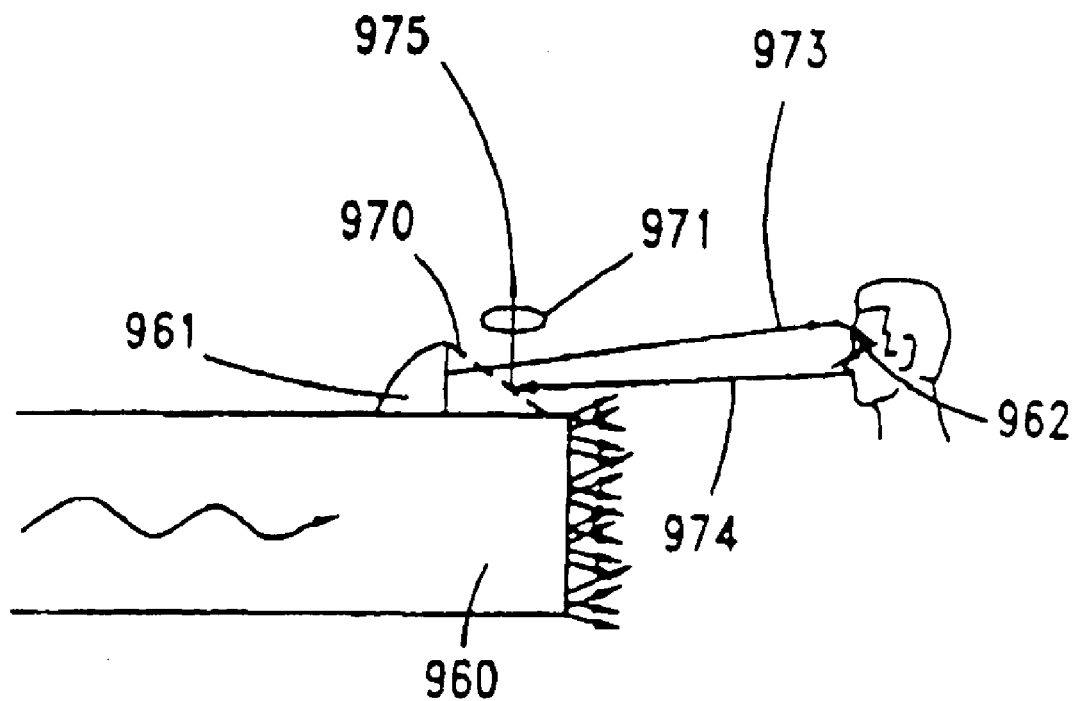

FIG. 17c illustrates another application of flashing device 961. By generating a flash with device 961 and determining whether detector 975 senses light retroreflected from eye 962, a microprocessor (not shown) in communication with a control circuit (not shown) and with detector 975, e.g. a photodetector, can determine that eye 962 is in danger of being injured from the imminent firing of a laser beam from the laser unit. The choroid layer of the retina diffusely reflects light source 973 that impinges thereon from the previously generated flash, and the optics of eye 962, re-image, or retroreflect, the light back to flashing device 961. Retroreflected beam 974 is reflected from beam splitter 970 through a lens (not shown) onto 975. Two additional adjacent detectors (not shown) detect light reflected from other areas in the room in which the laser unit is disposed. If the signal generated by detector 975 has a much larger amplitude than the signals generated by the additional detectors, the microprocessor determines that eye 962 is in firing range of a laser beam. The control circuit of flashing device 961then sends a disabling signal to the control system of the laser unit to thereby prevent firing of a laser unit. When detector 975 is used to detect a retroflected beam, and a flash is generated within the predetermined time before the firing of a laser beam, as illustrated in FIG. 17b, in order to cause uncontrollable blinking of the eye during propagation of the beam, the laser unit is inherently fail-safe. That is to say, even if the eye does not blink, detector 975 will determine that eye 962 is in firing range of a laser beam and the laser unit will cease operation.

As can be seen from the above description, a diffusing/diverging unit of the present invention, which is mounted to the exit aperture of a conventional laser unit, induces the exit beam to be divergent/ and or scattered at a wide angle. As a result the exit beam is not injurious to the eyes and skin of observers, as well as to objects located in the vicinity of the target. Nevertheless, the exit beam generally retains a similar level of energy density as the beam generated from the exit aperture when the diffusing unit is very close or essentially in contact with the target, and is therefore capable of performing various types of treatment, both for cosmetic surgery and for industrial applications. Protective eyeglasses are generally not needed, and if they are needed, conventional sunglasses would be the only requirement, thereby allowing work in an aesthetic clinic to be less cumbersome.

In another embodiment of the invention, the apparatus is provided with a unit for evacuating vapors, such as condensed vapors that were produced during the chilling of skin prior to the firing of the laser unit. The evacuation unit comprises a U-shaped vacuum chamber through which monochromatic light passes as it is directed to a skin target and a vacuum pump. During operation of the vacuum pump, the vacuum level within the vacuum chamber is increased by occluding a conduit of the vacuum chamber by a finger of the operator. As vacuum is applied to the skin target, skin is drawn toward the vacuum chamber and the concentration of blood vessels in the vicinity of the target increases. The added concentration of blood vessels increases the absorption of light within the tissue, and therefore facilitates treatment of a skin disorder.

Figure 18:
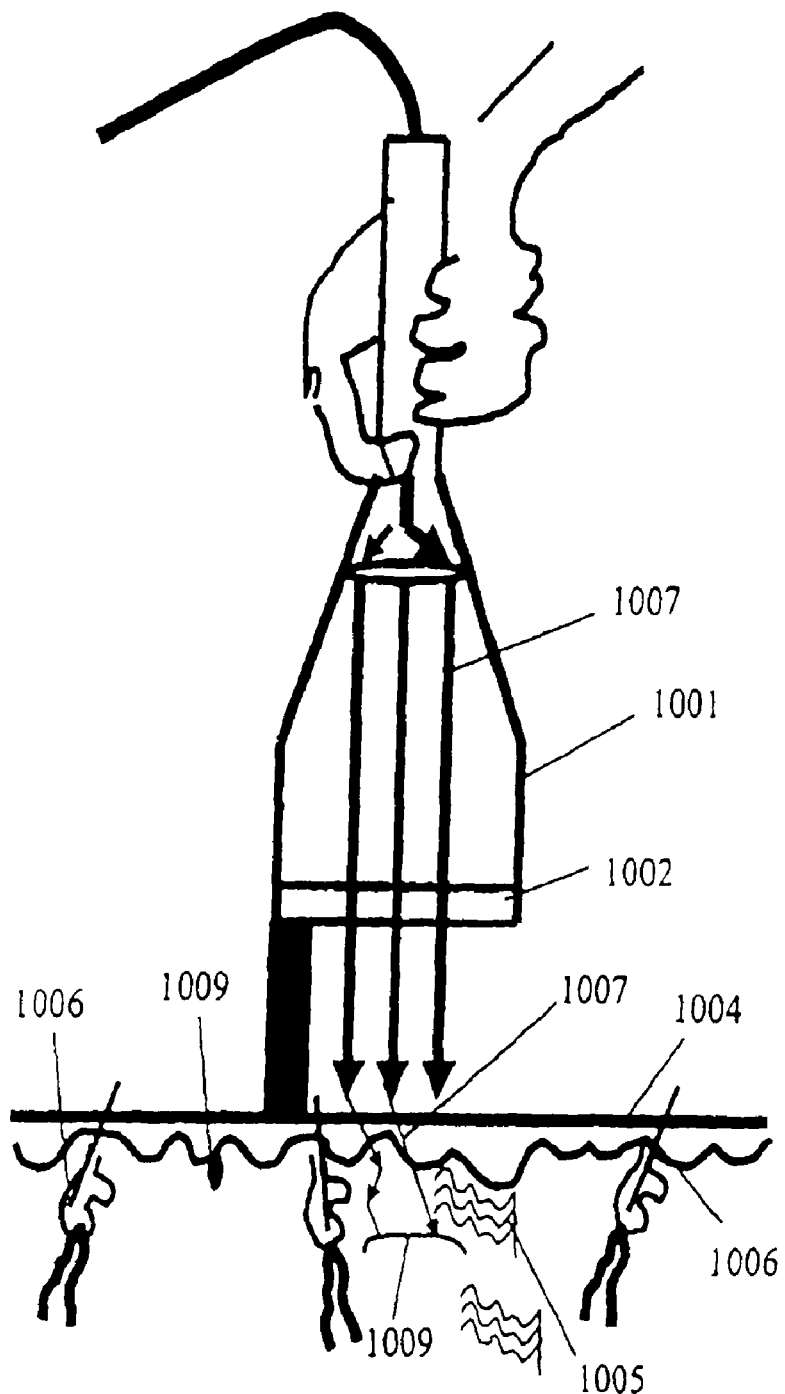
FIG. 18 is a schematic drawing which illustrates the propagation of an intense pulsed laser beam from a handpiece to a skin target according to a prior art method.

FIG. 18 illustrates the propagation of an intense pulsed laser beam the wavelength of which is in the visible or near infrared region of the spectrum, i.e. shorter than 1800 nm, from the distal end of a handpiece to a skin target according to a prior art method. Handpiece 1001 comprises clear transmitting element 1002, such as a lens or a window, which transmits monochromatic beam 1007 emitted from the laser unit and impinges skin target 1004. The beam penetrates skin target 1004 and selectively impinges a subcutaneous skin structure to be thermally injured, such as collagen bundle 1005, blood vessel 1009, or hair follicle 1006. In this method, external pressure or vacuum is not applied to the skin.

Figure 19:
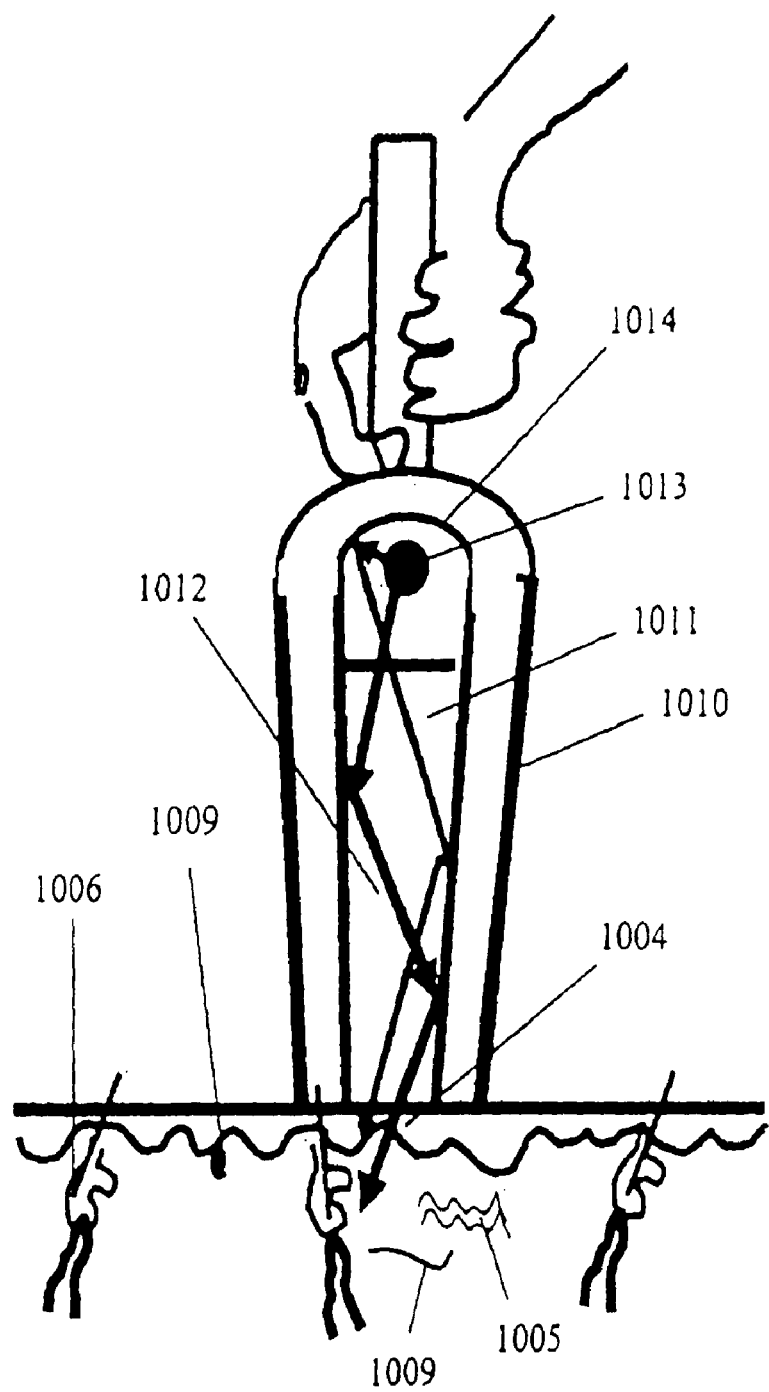
FIG. 19 is a schematic drawing which illustrates the propagation of an intense pulsed non-coherent light beam from a handpiece to a skin target according to a prior art method.

FIG. 19 illustrates a prior art non-coherent intense pulsed light system from which light is fired to a skin target for e.g. treatment of vascular lesions, hair removal, or photorejuvenation. Handpiece 1010 comprises light guide 1011 which is in contact with skin target 1004. Beam 1012, which is generated by lamp 1013 and reflected from reflector 1014, is non-coherent and further reflected by the light guide walls. In some handpieces, such as those produced by Deka (Italy), a clear transmitting element is utilized, rather than a light guide. Chilling gel is often applied to the skin when such a light system is employed. In this method, external pressure or vacuum is not applied to the skin, and the handpiece is gently placed on the skin target, so as to avoid removal of the gel layer, the thickness of which is desired to remain at approximately 0.5 mm.

Figure 20:
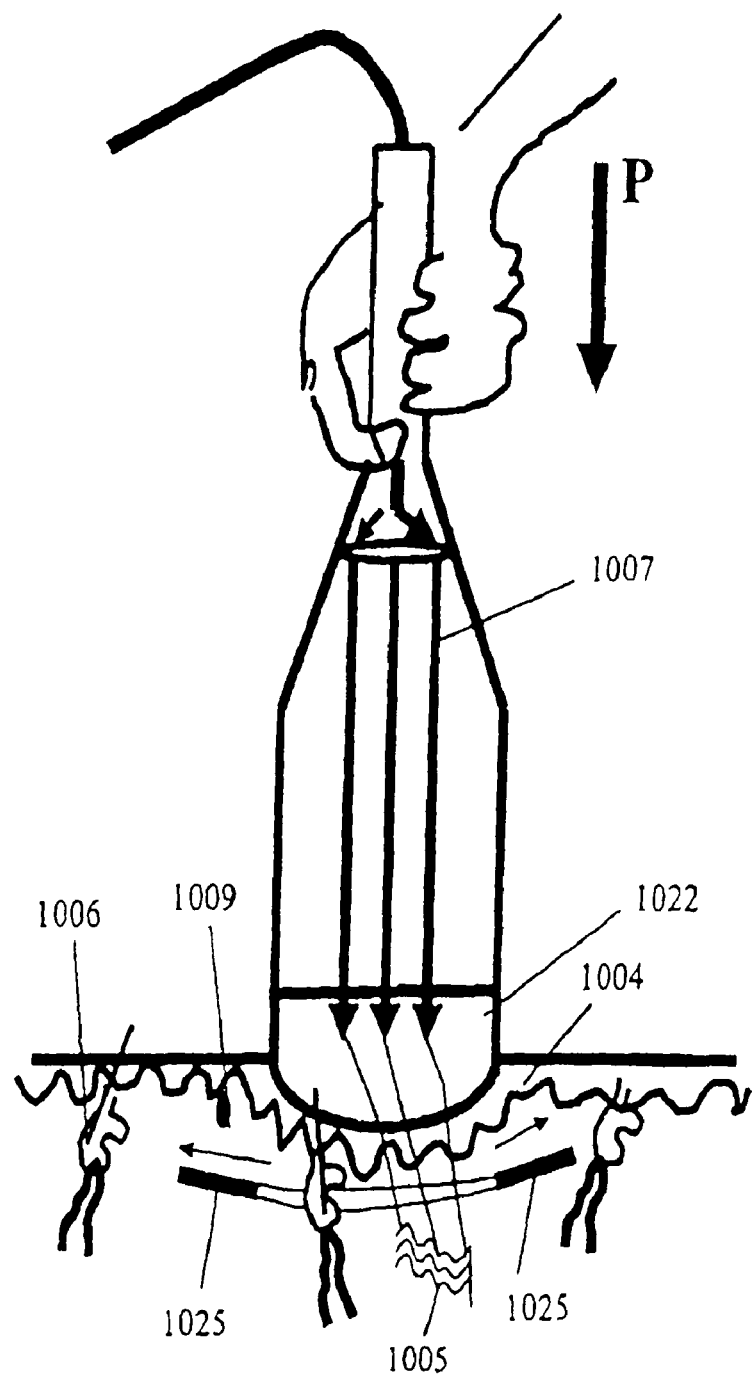
FIG. 20 is a schematic drawing of a prior art treatment method by which pressure is applied to a skin target, in order to expel blood from those portions of blood vessels which are in the optical path of subcutaneously scattered light.

FIG. 20 illustrates a prior art laser system similar to those of U.S. Pat. Nos. 5,595,568 and 5,735,844, which employs an optical component 1022 at the distal end thereof in contact with skin target 1004. Pressure is applied to skin target 1004, in order to expel blood from those portions of blood vessels 1025, as schematically illustrated by the arrows, which are in the optical path of subcutaneously scattered light, thereby allowing more monochromatic light to impinge hair follicle 1006 or collagen bundle 1005. Concerning hair removal, melanin is generally utilized as an absorbing chromophore.

Figure 21:
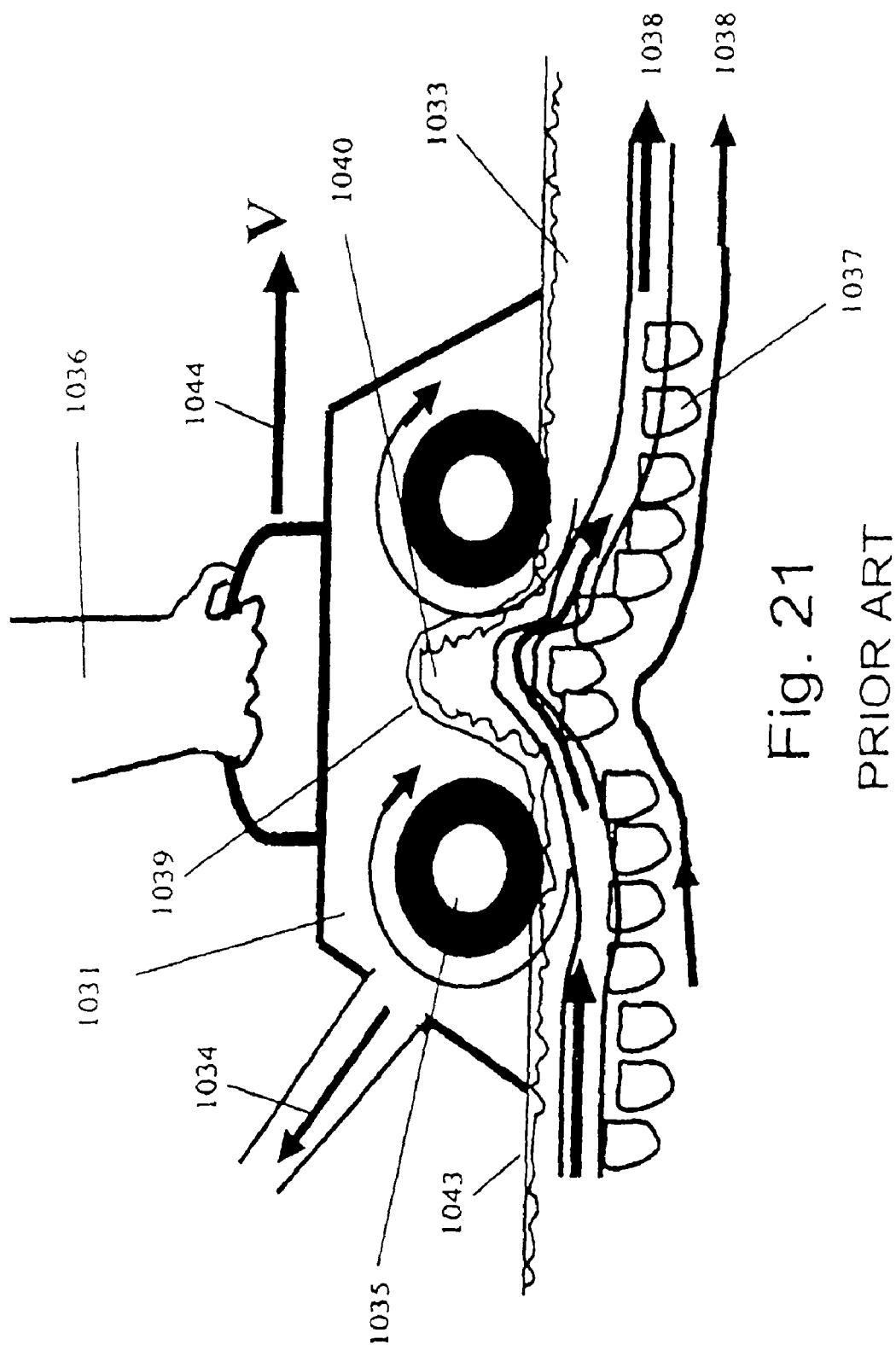
FIG. 21 is a schematic drawing of a prior art vacuum-assisted rolling cellulite massage device.

FIG. 21 illustrates a prior art device 1031, such as that produced by LPG (France), which is in pressing contact with skin 1033 in order to perform a deep massage of cellulite adipose layer 1037. Device 1031 is formed with a convex surface 1039 in a central region of its planar skin contacting surface 1043. Device 1031 stimulates the flow of lymphatic fluids in their natural flow direction 1038 in order to remove toxic materials from the adjoining tissue. The stimulation of lymphatic fluid flow is achieved by applying a vacuum to the interior of device 1031 so that air is sucked therefrom in the direction of arrow 1034 of the skin. The application of the vacuum draws skin toward convex surface 1039 and induces the temporary formation of skin fold 1040, which is raised in respect to adjoining skin 1033. Due to the elasticity of skin, skin fold 1040 returns to its original configuration, similar to the adjoining skin, upon subsequent movement of device 1031, while another skin fold is formed. As device 1031 is moved by hand 1036 of a masseur in direction 1044 of the device, similar to natural flow direction 1038 the lymphatic fluids flow in their natural flow direction. However, the lymphatic fluids will not flow if device 1031 were moved in a direction opposite to direction 1044. Wheels 1035 enable constant movement of device 1031.

In some cellulite massage devices, such as those produced by Deka (Italy) or the Lumicell Touch (USA), a low power continuous working infrared light source with a power level of 0.1-2 W/cm$^2$ provides deep heating of the cellulite area and additional stimulation of lymphatic flow. Such a light source is incapable of varying the temperature by more than 2-3° C., since higher temperatures would be injurious to the tissue and cause hyperthermia. Consequently these massage devices are unable to attain the temperatures necessary for achieving selective thermal injury of blood vessels, hair follicles or for the smoothening of fine wrinkles. Due to the movement of the device, the amount of optical energy, e.g. by means of an optical meter, to be applied to the skin cannot be accurately determined.

Figure 22:
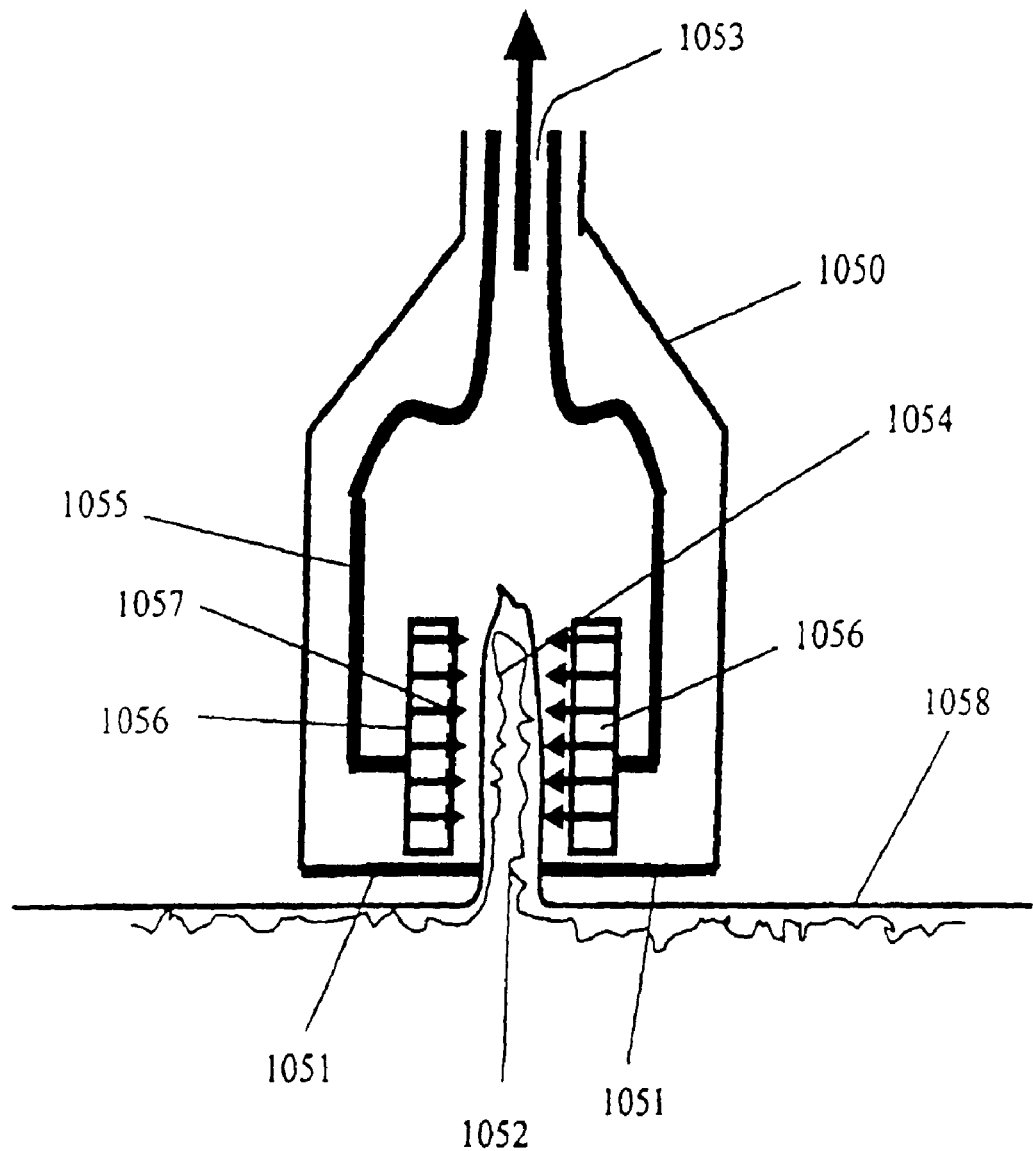
FIG. 22 is a schematic drawing of a prior art vacuum-assisted hair removal device adapted to reduce the blood concentration within a skin fold formed thereby, in order to illuminate two opposed sides of the skin fold and consequently remove melanin-rich hair shafts.

FIG. 22 illustrates a prior art hair removal device, similar to the device of U.S. Pat. No. 5,735,844, which is provided with a slot 1052 within a central region of skin contacting surface 1051 of handpiece 1050. When handpiece 1050 is placed on skin surface 1058 and a vacuum is applied to the handpiece via opening 1053, skin fold 1054 is formed. A narrow slot 1052 induces formation of a correspondingly longer skin fold 1054. Optical radiation is transmitted to the two opposed sides 1056 of skin fold 1054 by a corresponding optical fiber 1055 and optical element 1057. Upon application of the vacuum, skin fold 1054 is squeezed to prevent blood flow therethrough. This device is therefore intended to reduce the concentration of blood within skin fold 1054, in order to increase illumination of melanin-rich hair shafts, in contrast with the apparatus of this embodiment by which blood concentration is increased within the slight vacuum-induced skin protrusion so as to induce increased light absorption, as will be described hereinafter. Furthermore, this prior art device, due to the reduced concentration of blood within skin fold 1054, is not suitable for treatment of vascular lesions, photo-rejuvination, or the method of hair removal which is aided by the absorption of optical energy by blood vessels that surround or underly hair follicles (as opposed to the method of hair removal which is aided by the absorption of optical energy by melanin.

Figure 23:
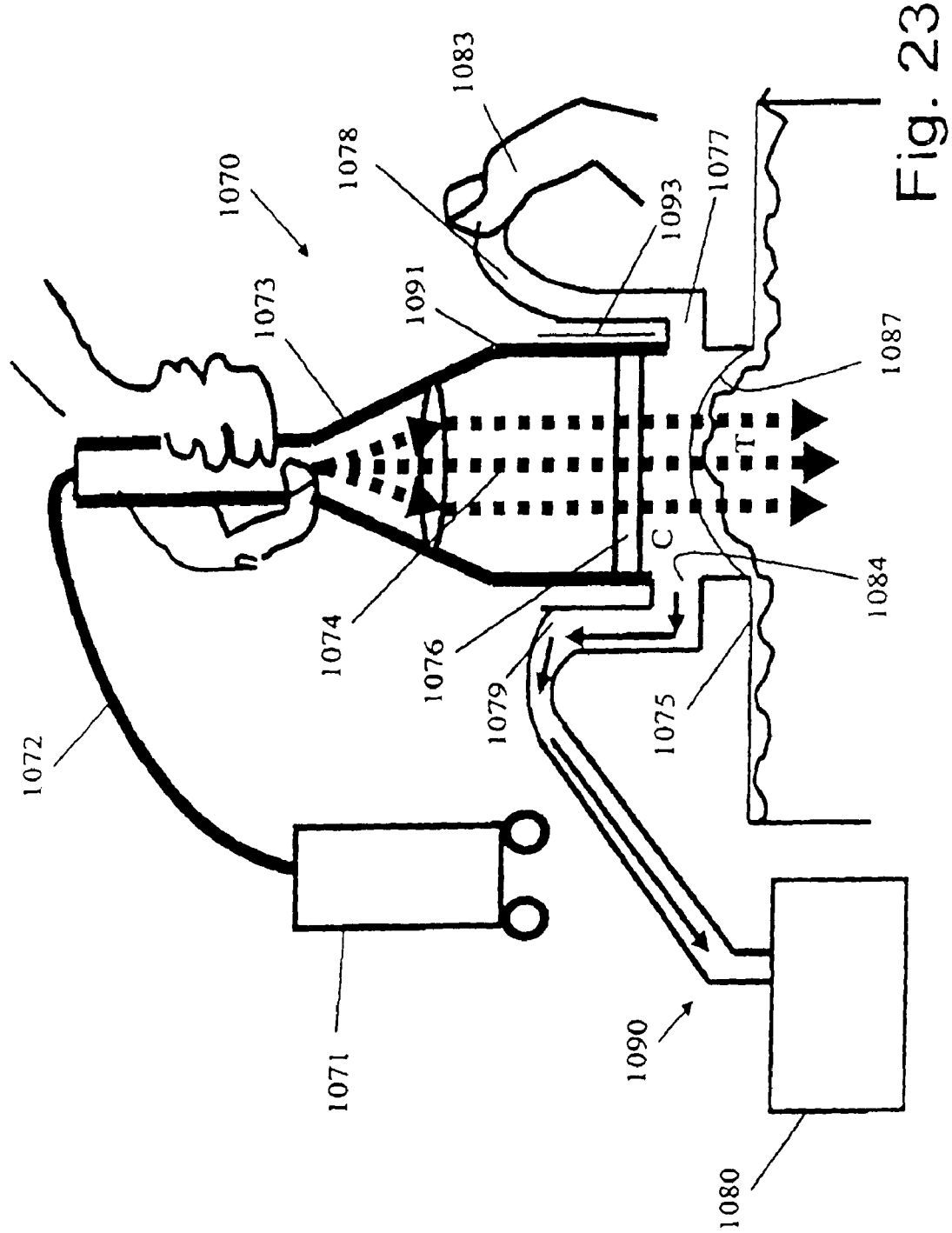
FIG. 23 is a schematic drawing of apparatus in accordance with one embodiment of the present invention, employing a manually occluded U-shaped evacuation chamber.

FIG. 23 illustrates the apparatus according to an embodiment of the invention, which is generally designated by numeral 1070. Apparatus 1070 comprises monochromatic light source 1071, handpiece 1073 provided with clear transmitting element 1076 at its distal end, and an evacuation unit which is designated by numeral 1090.

Evacuation unit 1090 comprises vacuum pump 1080, vacuum chamber C, and conduits 1078 and 1079 in communication with chamber C. Vacuum chamber C, which is placed on skin surface 1075, is formed with an aperture (not shown) on its distal end and is provided with a clear transmitting element 1076 on its proximate end. Vacuum chamber C is integrally formed with handpiece 1073, such that cylindrical wall 1091 is common to both handpiece 1074 and vacuum chamber C. Element 1076 is transparent to beam 1074 of intense pulsed light which is directed to skin target T. Element 1076 is positioned such that beam 1074 is transmitted in a direction substantially normal to skin surface 1075 adjoining skin target T. The ratio of the maximum length to maximum width of the opening, which may be square, rectangular, circular, or any other desired shape, ranges from approximately 1 to 4. Since the aperture is formed with such a ratio, skin target T is proximately drawn, e.g. 1 mm from skin surface 1075, and is slightly deformed, as indicated by numeral 1087, while increasing the concentration of blood in skin target T. Likewise, employment of an aperture with such a ratio precludes formation of a vacuum-induced skin fold, which has been achieved heretofore in the prior art and which would reduce the concentration of blood in skin target T.

Wall 1091 is formed with openings 1077 and 1084 in communication with conduits 1078 and 1079, respectively. The two conduits have a horizontal portion adjacent to the corresponding opening, a vertical portion, and a long discharge portion. Openings 1077 and 1084 are sealed with a corresponding sealing element 1093, to prevent seepage of fluid from the vacuum chamber. Conduit 1079 is also in communication with vacuum pump 1080, which draws fluid, e.g. air, thereto at subatmospheric pressures. U-shaped vacuum chamber C is therefore defined by clear transmitting element 1076 of the handpiece, slightly deformed skin surface 1087, wall 1091 and conduits 1078 and 1079.

A suitable light source is a pulsed dye laser unit, e.g. produced by Candela or Cynosure, for the treatment of vascular lesions, which emits light having a wavelength of approximately 585 nm, a pulse duration of approximately 0.5 microseconds and an energy density level of 10 J/cm$^2$. Similarly any other suitable high intensity pulsed laser unit, such as a Nd:YAG, pulsed diode, Alexandrite, Ruby or frequency doubled laser, operating in the visible or near infrared region of the spectrum may be employed. Similarly, a laser unit generating trains of pulses, such as the Cynosure Alexandrite laser, the Lumenis "Quatim" IPL or Deka "Silkapill". The emitted light is transmitted via optical fiber 1072 to handpiece 1073. Handpiece 1073 is positioned such that clear transmitting element 1076 faces skin surface 1087. Beam 1074 propagating towards slightly protruded skin surface 1087 is substantially normal to skin surface 1075.

Following operation of vacuum pump 1080, air begins to become evacuated from vacuum chamber C via conduit 1079. Occluding conduit 1078, such as by placing finger 1083 of an operator on its outer opening increases the level of the vacuum within chamber C to a pressure ranging from 200 to 1000 millibar. The application of such a vacuum slightly draws skin target T towards chamber C without being pressed, as has been practiced heretofore in the prior art, thereby increased the concentration of blood vessels within skin target T. The efficacy of a laser unit in terms of treatment of vascular lesions is generally greater than that of the prior art, due to the larger concentration of blood vessels in skin target T, resulting in greater absorption of the optical energy of beam 1074 within bodily tissue.

The operator may fire the laser following application of the vacuum and the subsequent change in color of skin target T to a reddish hue, which indicates that the skin is rich in blood vessels. The time delay between the application of the vacuum and the firing, of the laser is based on clinical experience or on visual inspection of the tissue color.

Figure 24:
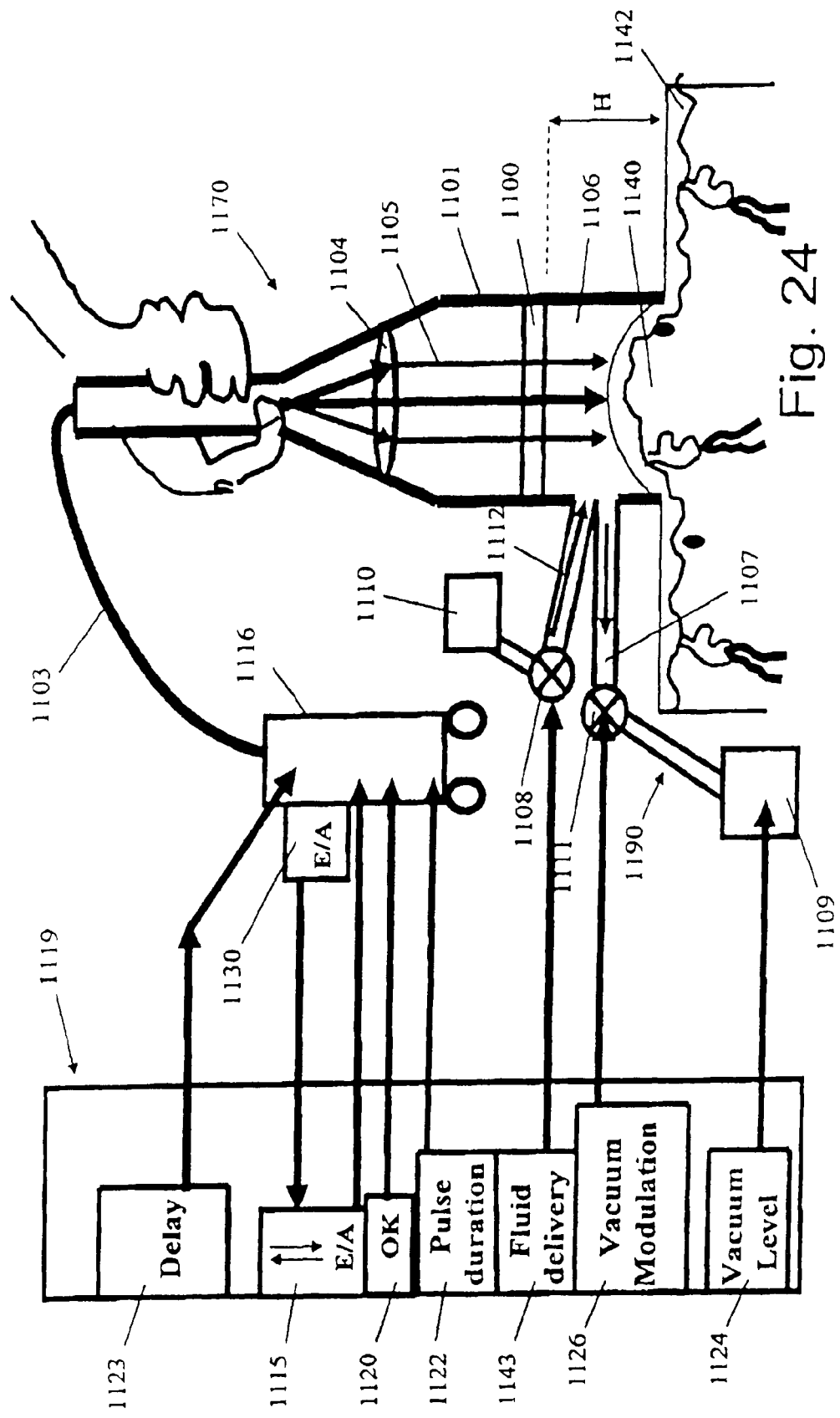
FIG. 24 is a schematic drawing of apparatus in accordance with another embodiment of the present invention, employing an electronically occluded evacuation chamber.

FIG. 24 illustrates another embodiment of the present invention wherein the operation of the vacuum pump and the pulsed laser unit are electronically controlled. The depth of light penetration within the tissue may be controlled by controlling the time delay between application of the vacuum and the firing of the pulsed laser. If the time delay is relatively short, e.g. 10 msec, blood vessel enrichment will occur only close to the surface of the skin at a depth of approximately 0.2 mm, while if the delay is approximately 300 msec, the blood vessel enrichment depth may be as great as 0.5-1.0 mm.

Apparatus 1170 comprises handpiece 1101, laser system 1116, evacuation unit 1190 and control unit 1119.

Laser system 1116 includes a power supply (not shown), a light generation unit (not shown), and power or energy detector 1130 for verifying that the predetermined energy density value is applied to the skin target. Handpiece 1101 held by the hand of the operator is provided with lens 1104, which directs monochromatic beam 1105 transmitted by optical fiber 1103 from laser system 1116 to skin target area 1140. Clear transmitting element 1100 defining vacuum chamber 1106 is generally in close proximity to skin surface 1142, at a typical separation H of 1.2 mm and ranging from 0.5 to 4 mm, depending on the diameter of the handpiece. The separation is sufficiently large to allow for the generation of a vacuum within chamber 1106, but less than approximately one-half the diameter of the window 1100, in order to limit the protrusion of skin target 1140 from the adjoining skin surface 1142. By limiting the separation of element 1100 from skin surface 1142 while maintaining the vacuum applied to skin target 1140, formation of a skin fold is precluded while more blood may be accumulated in a smaller skin thickness. Therefore a significant local rise in the temperature of a blood vessel, which ranges from 50.70° C., is made possible.

Evacuation unit 1190 comprises vacuum chamber 1106 which is not U-shaped, miniature vacuum pump 1109 suitable for producing a vacuum ranging from 200-1000 millibar, conduit 1107 and control valve 1111 through which subatmospheric fluid is discharged from chamber 1106, and miniature pressurized tank 1110 containing, e.g 100 ml, which delivers air through conduit 1112 and control valve 1108 to chamber 1106. If so desired, a clear transmitting element need not be used, and vacuum chamber 1106 defined by lens 1104 will have an accordingly larger volume.

Control unit 1119 comprises the following essential elements:

a) Display 1115 of the energy density level of the monochromatic light emitted by laser system 1116 and a selector for selecting a predetermined energy density.

b) Confirmation indicator 1120 which verifies that the selected energy density is being applied to the skin. Control circuitry deactivates the laser power supply if a beam having an energy density significantly larger than the predetermined value is being fired.

c) Display 1122 concerning the pulse structure, such as wavelength, pulse duration and number of pulses in a train.

d) Control circuitry 1123 for selecting the time delay between operation of vacuum pump 1109 and laser system 1116.

e) Selector 1124 for controlling the vacuum level in vacuum chamber 106 by means of pump 1109.

f) Control circuitry 1126 for controlling the vacuum duty cycle by regulating the operating cycle of vacuum pump 1109, the open and close time of control valve 1111, the average vacuum pressure, the vacuum modulation frequency, and the repetition rate.

g) Control circuitry 1143 for delivering fluid from positive pressure tank 1110 by controlling the duty cycle of control valve 1108.

Tank 1110, in which air having a pressure ranging from 1.2 atmospheres is contained, provides a fast delivery of less than 1 msec of air into chamber 1106, as well as a correspondingly fast regulation of the vacuum level therein by first opening control valves 1108 and 1111 and activating vacuum pump 1109. After a sufficient volume of fluid, e.g 1 ml, is delivered to chamber 1106, control valve 1108 is closed. Control circuitry 1126 and 1143 then regulate the operation of the control valves so to maintain a predetermined level of vacuum. Upon achieving the predetermined vacuum level, control circuitry 1123 fires laser system 1116 after the predetermined time delay, which may range from 1-1000 msec.

Figure 25:
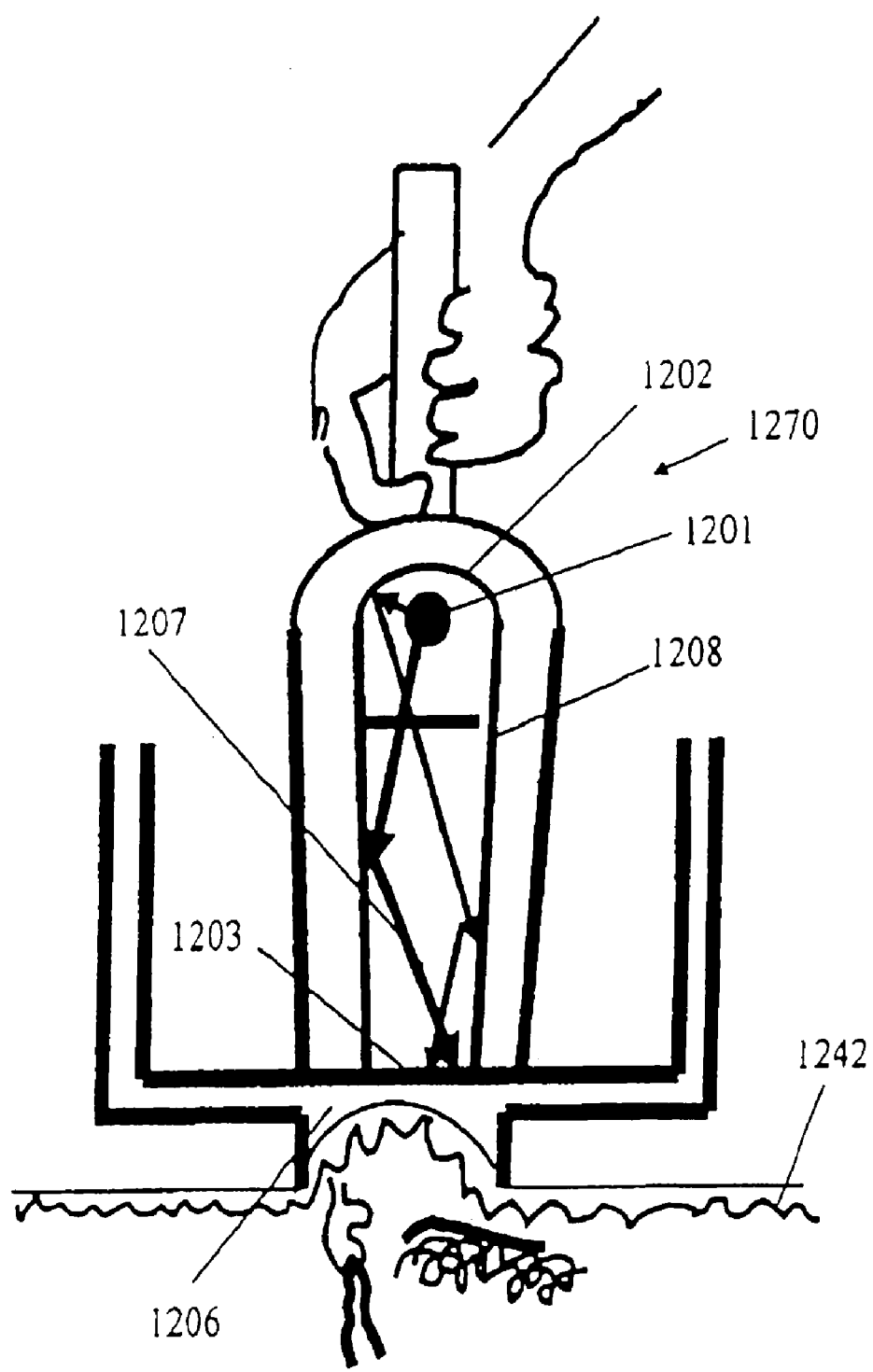
FIG. 25 is a schematic drawing of apparatus in accordance with the present invention, employing an intense pulsed non coherent light source.

FIG. 25 illustrates apparatus 1270, which comprises a non-coherent intense pulsed light system similar to that described with respect to FIG. 19 and provided with Xe flashlamp 1201, such as one manufactured by Lumenis, Deka, Palomar, or Syneron. Reflector 1202 reflects the emitted light 1207 to light guide 1208. Distal end 1203 of light guide 1208 is separated 1-2 mm from skin surface 1242 to allow for the generation of a vacuum in vacuum chamber 1206 without compromising treatment efficacy by limiting the protrusion of the skin target from the adjoining skin surface 1242.

Figure 26:
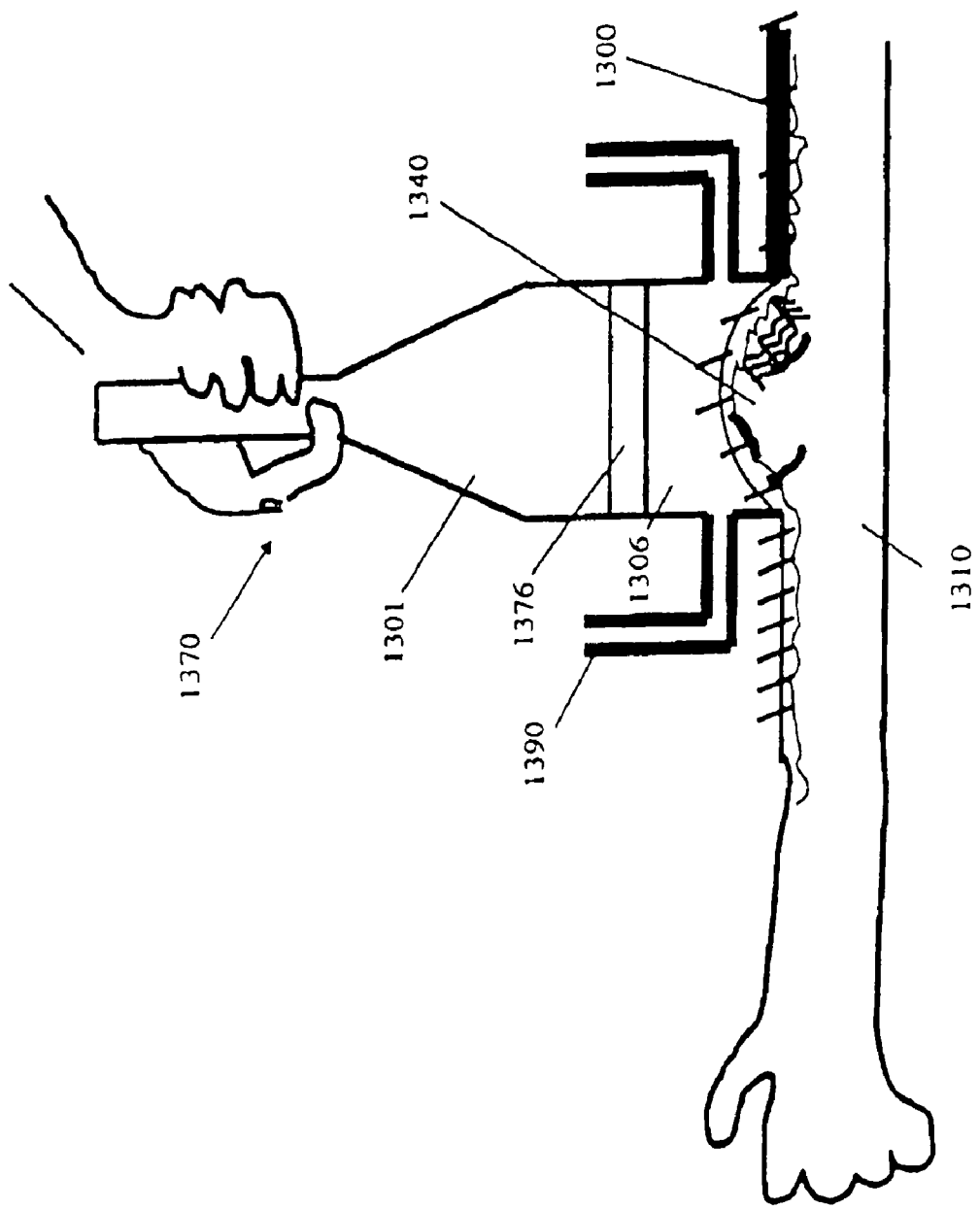
FIG. 26 is a schematic drawing of apparatus in accordance with the present invention, which is provided with a skin chiller.

FIG. 26 illustrates the placement of apparatus 1370 onto arm 1310. Apparatus 1370 comprises handpiece 1301, evacuation unit 1390, and skin chiller 1300 for cooling the epidermis of arm 1310, which is heated as a result of the impingement of monochromastic light thereon. Skin chiller 1300 is preferably a metallic plate made of aluminum, which is in contact with the epidermis and cooled by a thermoelectric cooler. The temperature of the plate is maintained at a controlled temperature, e.g. 0° C. The chilled plate is placed on a skin region adjacent to skin target 1340. The epidermis may be chilled prior to the light treatment by other suitable means, such as by the application of a gel or a low temperature liquid or gas sprayed onto the skin target.

Figure 2E:
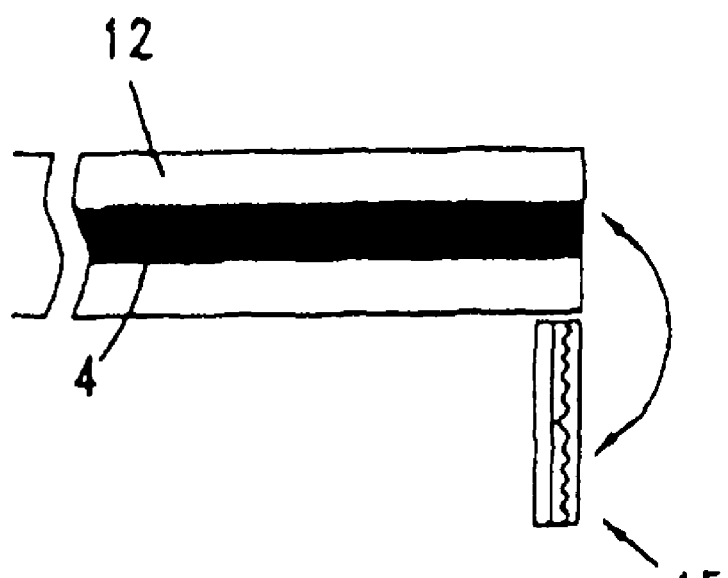

It will be appreciated that the utilization of a U-shaped vacuum chamber 1306 for the evacuation of vapors which condense on clear transmitting element 1376 is particularly advantageous when a skin chiller in permanent contact with the handpiece outer wall is employed. Such a skin chiller is illustrated in FIG. 26 or FIG. 15*f*, resulting in condensation of vapors on the transmitting element that would not be evacuated without employment of an evacuation unit in accordance with the present invention. When the skin chiller of FIG. 15*f* is employed, the skin chiller is displaced, for example by a releasable attachment means as shown in FIG. 2*e* or by any other suitable method, such that it is contact with the vacuum chamber.

Figure 27:
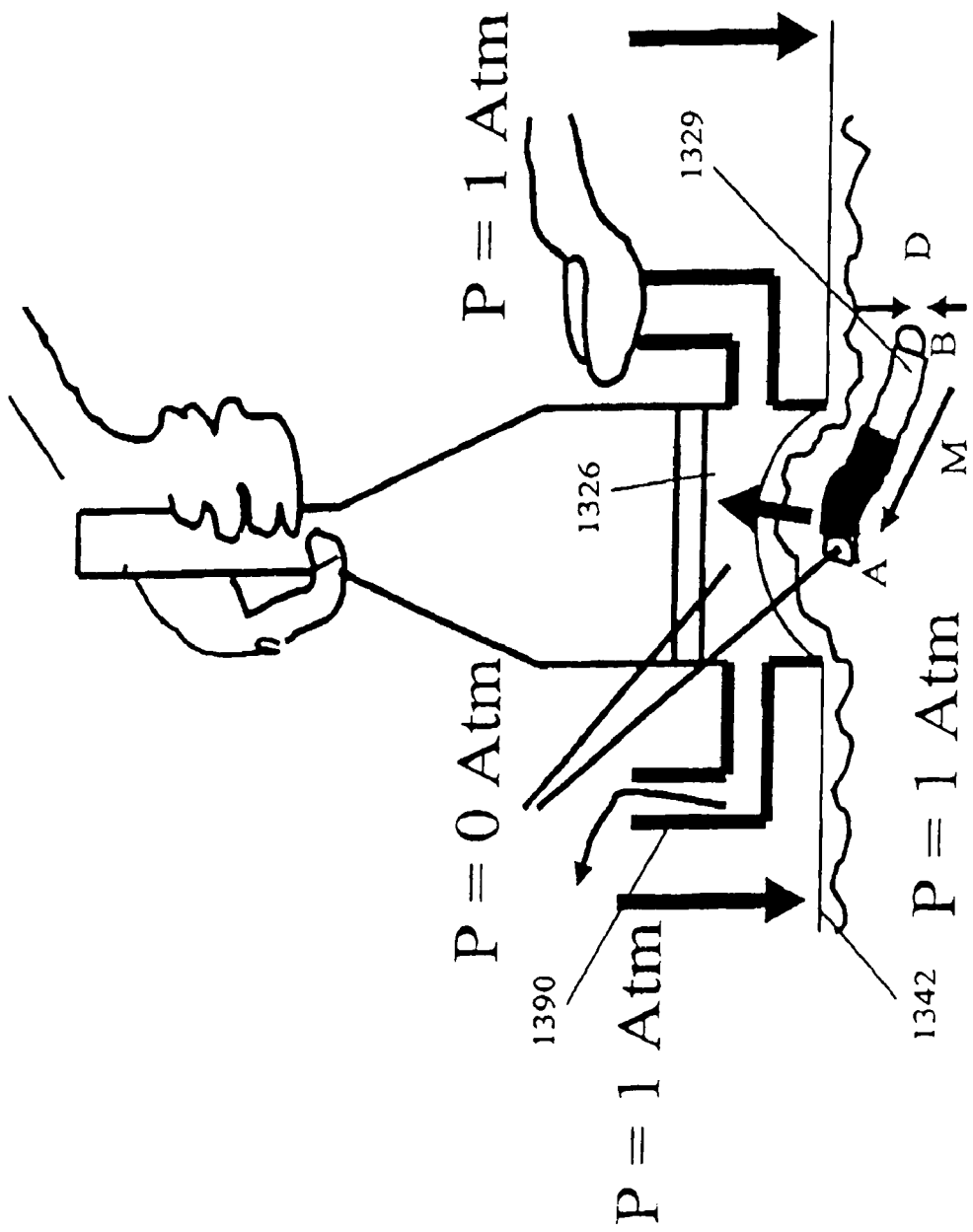
FIG. 27 is a drawing which schematically illustrates the effect of applying a subatmospheric pressure to a vacuum chamber in order to increase the blood concentration in skin drawn towards the vacuum chamber.

FIG. 27 schematically illustrates the effect of applying a subatmospheric pressure to a skin target, in accordance with the present invention, in order to enhance the absorption of light by blood vessels within the skin target. For clarity, the drawing illustrates the effect with respect to a single blood vessel; however, it should be appreciated that many blood vessels contribute to the effect of increased blood transport whereby a plurality of blood vessels are drawn to the epidermis, resulting in increased absorption of the optical energy. The protrusion of the skin target relative to the adjoining skin surface is also shown in disproportionate fashion for illustrative purposes.

The increase in light absorption within blood vessels due to the application of a vacuum in the vicinity of a skin target depends on the vacuum level, or the rate of vacuum modulation, and the skin elasticity which is reduced with increased age. As shown, blood vessel 1329 of diameter D is in an underlying position relative to vacuum chamber 1326. By applying a vacuum by means of evacuation unit 1390, blood flow is established in blood vessel 1329 in the direction of arrow M, due to a difference of pressures between points A and B closer and farther from vacuum chamber 1326, respectively. If the blood vessel is a vein, the flow will be established in only one direction, due to the influence of the corresponding vein valve.

According to the Hagen-Poisseuille equation concerning the flow of viscous fluids in tubes, the discharge from a tube and consequently the duration of flow therethrough depends on a pressure gradient along the tube, the fourth power of the diameter of the tube, and the length thereof. For example, diameters of 100 microns are common for capillaries adjacent to the papillary dermis at a depth of approximately 200 microns and 500 micron blood vessel diameters can be found in the hair bulb at a depth of 3 mm. A typical blood vessel length is approximately 1-2 cm. It will be appreciated that although the blood vessel diameters generally increase with depth, the pressure gradient along the blood vessel is smaller at deeper layers of the skin. As a result, for a given pressure, such as the application of a zero millibar vacuum, each depth from the skin surface corresponds to a characteristic time response for being filled by blood. As a result, modulation of the vacuum by opening and closing control valve 1111 (FIG. 24) controls the flow of blood through blood vessels and consequently controls the degree of light absorption by a blood vessel at a given depth from skin surface 1342. In a realistic situation wherein a plurality of blood vessels are located within a skin target, each skin layer is characterized by a different modulation frequency which typically ranges between 100 Hz for upper layers and 1 Hz for the deep layers under the hair follicles. By opening control valves 1108 and 1111 (FIG. 24) by a varying frequency, the operator may modulate the vacuum applied to the skin target and thereby vary the blood richness of different skin layers.

The operator typically determines an instantaneous modulation frequency of control valves 1108 and 1111 by visually inspecting the skin target and viewing the degree of redness thereat in response to a previous control valve modulation frequency. In addition to improving the treatment efficacy, an increased degree of redness within the skin target advantageously requires a lower energy density of intense pulsed light for achieving blood coagulation or blood heating resulting in the heating of the surrounding collagen. Alternatively, an erythema, i.e. skin redness, meter, e.g. produced by Courage-Hazaka, Germany, may be employed for determining the degree of redness, in order to establish the necessary energy density for the treatment.

For example, a modulation frequency as high as 40 Hz or the firing of a Dye laser unit approximately 1/40 seconds after application of a, vacuum may be necessary for applications of port wine stains. In contrast, a delay of approximately a half second for fine wrinkle removal and of approximately 1 second for hair removal may be needed for a depth of 1-3 mm under the skin surface.

Figure 28:
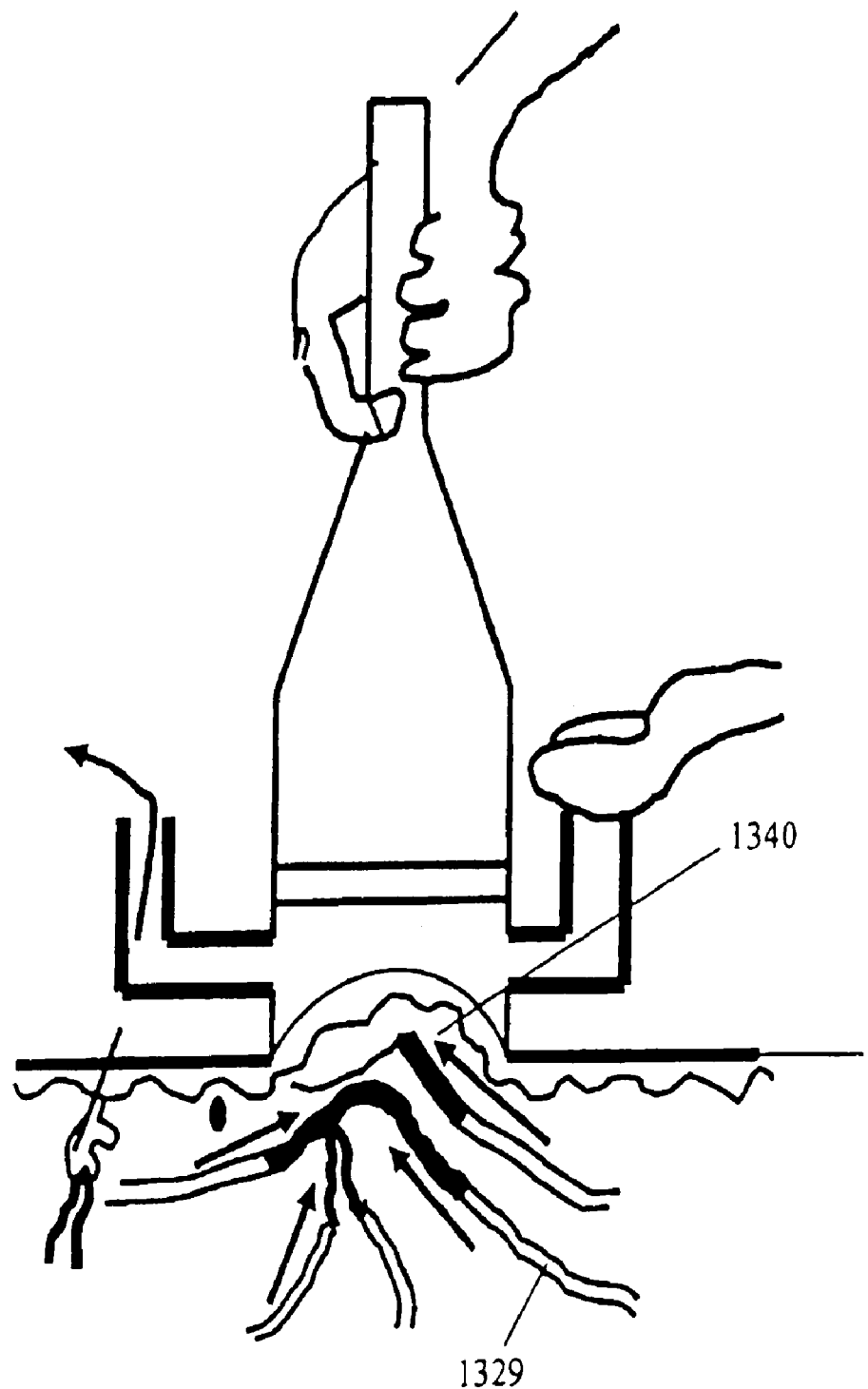
FIG. 28 is a drawing which schematically illustrates the increased concentration of a plurality of blood vessels in a skin target following application of a vacuum to a vacuum chamber, resulting in increased redness of skin and enhanced absorption of light.

FIG. 28 illustrates the concentration of a plurality of blood vessels 1329 in a skin target 1340, which results in the increase of redness of skin and enhanced absorption of light with respect to the hemoglobin absorption spectrum and scattering properties of skin. Light absorption is enhanced by a larger number of blood vessels per unit volume due to the correspondingly larger number of light absorbing chromophores. The beneficial effect of vacuum assisted absorption by Dye lasers or any yellow light, which is strongly absorbed by hemoglobin, is more pronounced on white or yellow skin not rich in blood vessels, such as that of smokers. Such types of skin suffer from enhanced aging and require photorejuvenation, the efficacy of which is improved with the use of the present invention. Enhanced absorption of light is also advantageously achieved when infrared lasers and intense pulsed light sources are employed.

Figure 29:
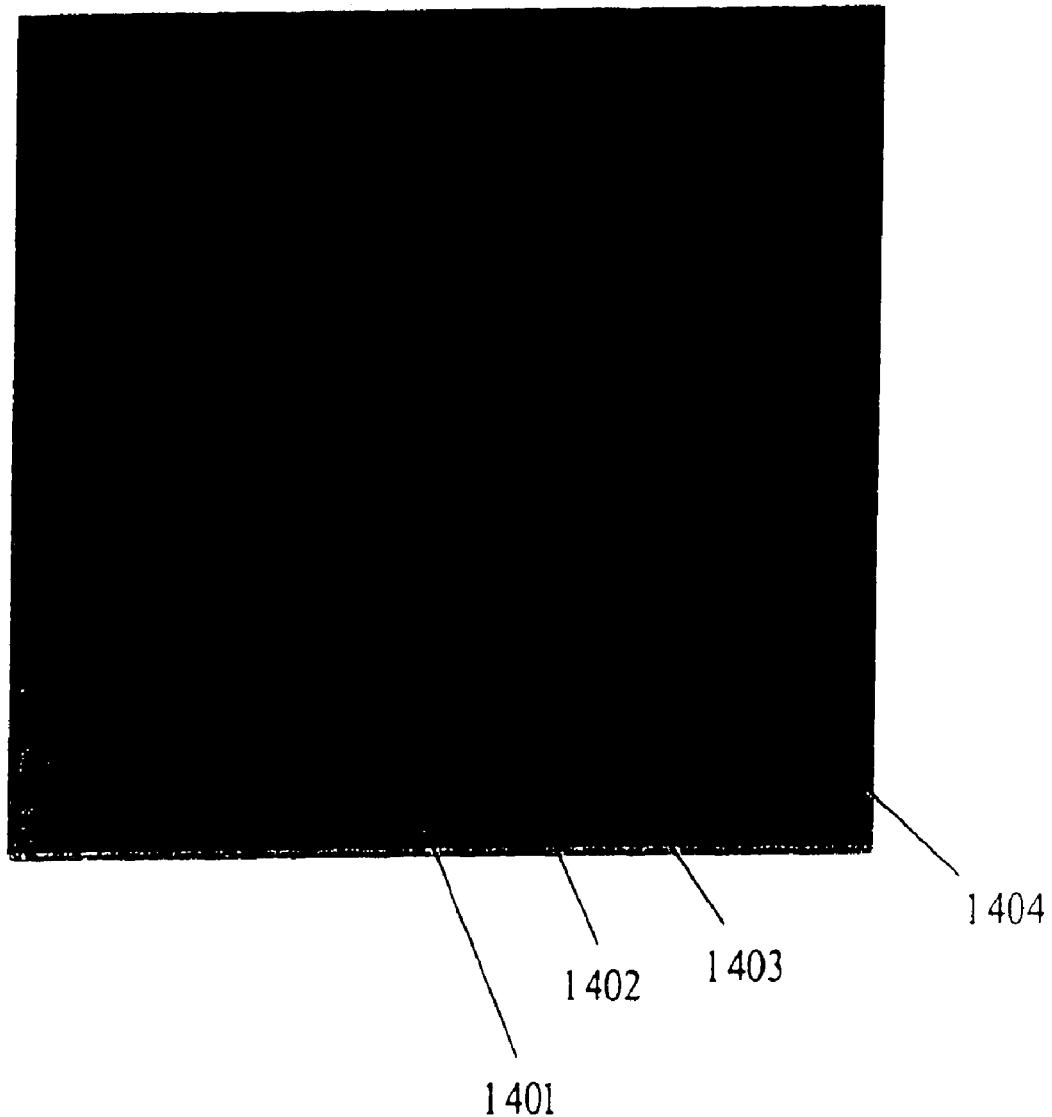
FIG. 29 is a photograph illustrating the change in skin color following treatment of a fine wrinkle by use of a vacuum assisted handpiece in accordance with the present invention.

FIG. 29 is a photograph illustrating the treatment of a fine wrinkle 1401 by means of a vacuum assisted handpiece according to the current invention, which was taken one-half of a second after the application of a vacuum. Circles 1402-4 indicate the sequential treatment spots. The color in the circle 1403 has changed.

Figure 30:
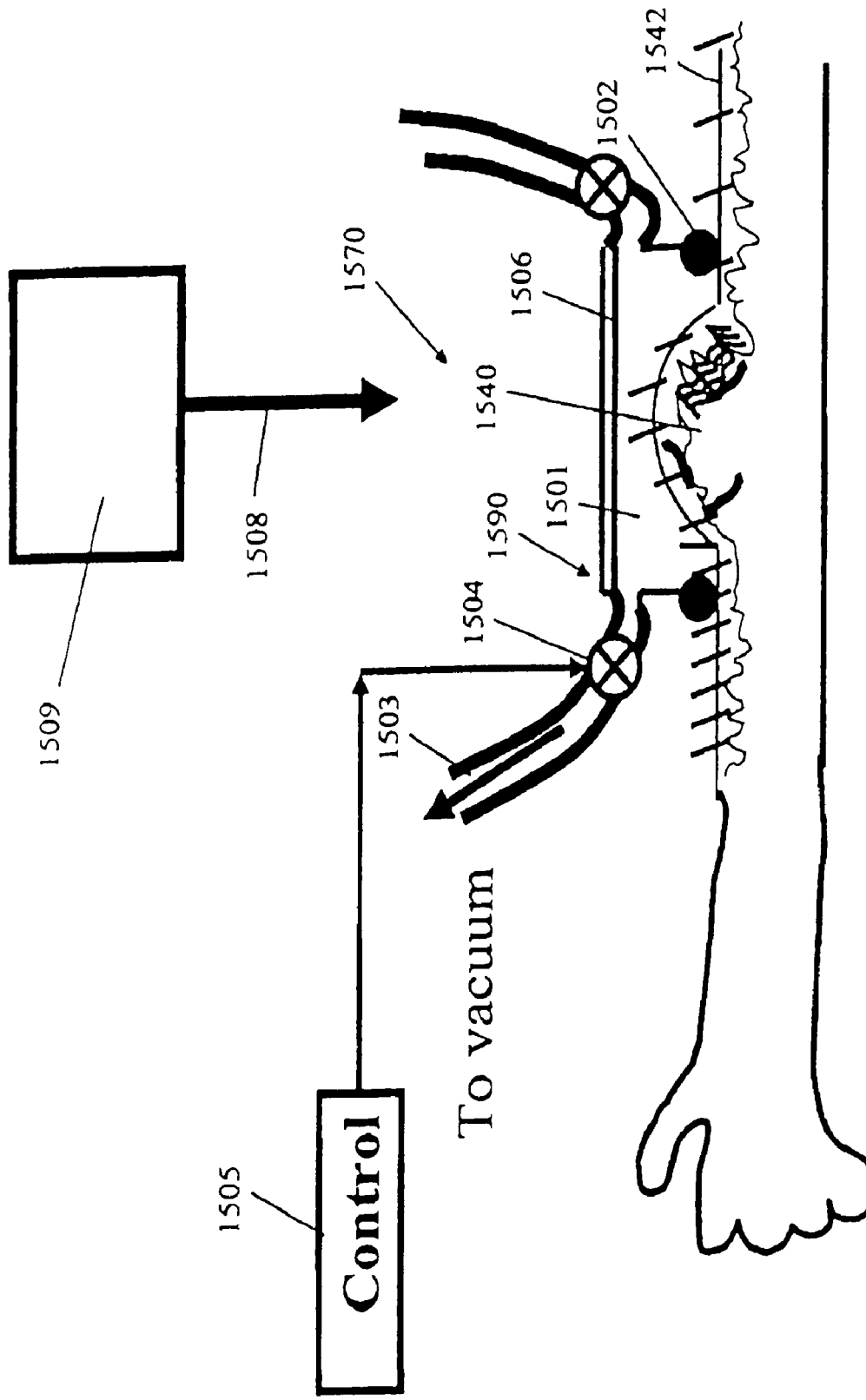
FIG. 30 is a schematic drawing of another embodiment of the invention, illustrating propagation of intense pulsed light from an external light source to a transparent modulated vacuum chamber.

FIG. 30 illustrates apparatus 1570 which increases blood vessel concentration within a skin target without use of a handpiece. Apparatus 1570 comprises evacuation unit 1590 having a transparent vacuum chamber 1501 made of a thin, transparent polymer 1506, such as polycarbonate or glass, which is transparent to visible or near infrared light. Vacuum chamber 1501 has a diameter of 5.20 mm and a height of approximately 1.3 mm, in order to avoid excessive protrusion of the skin. Chamber 1501 is preferably cylindrical, although other configurations are also suitable. Soft silicon rim 502 is adhesively affixed to the periphery of the chamber 1501, in order to provide good contact with skin surface 1542. Conduit 1503 in communication with control valve 1504 allows for the evacuation of vacuum chamber 1501 by means of a miniature vacuum pump (not shown) and control unit 1505. After chamber 1501 is placed on skin target 1540, pulsed beam 1508 from any existing intense pulsed laser or light source 1509 which operate in the visible or near infrared regions of the spectrum may propagate therethrough and effect treatment of a skin disorder. The advantage of this apparatus is its low price and its ability to interact with any intense pulsed laser or non-coherent light source which is already installed in a health clinic.

The absorption of visible intense pulsed light in blood vessels when vacuum is applied to a skin target may be enhanced by the directing electromagnetic waves to the skin target. Radio frequency waves operating in the range of 0.2-10 Mhz are commonly used to coagulate tiny blood vessels. The alternating electrical field generated by a bipolar RF generator, such as produced by Elman, USA, follows the path of least electrical resistance, which corresponds to the direction of blood flow within blood vessels.

FIG. 31 illustrates apparatus 1870 which comprises intense pulsed laser or intense pulsed light source 1821, RF source 1811, and evacuation unit 1890. Evacuation unit 1890 comprises vacuum chamber 1801, which is placed on skin surface 1802 to be treated for vascular lesions, miniature vacuum pump 1805, and control valve 1804 for regulating the level of the vacuum in chamber 1801. Clear transmitting element 1806 is positioned in such a way that beam 1820 generated by light source 1821 propagates therethrough and impinges skin surface 1802 at an angle which is substantially normal to the skin surface.

RF source 1811 is a bipolar RF generator which generates alternating voltage 1807 applied to skin surface 1802 via wires 1808 and electrodes 1809. Electric field 1810 generally follows the shape of blood vessels 1813, which are the best electrical conductors in the skin. Due to the concentration of blood vessels 1813 in the epidermis, the depth of which below skin surface 1802 depending on the vacuum level and the frequency of vacuum modulation, the combined effect of optical energy in terms of beam 1820 and pulsed RF field 1810 heats or coagulates the blood vessels.

Control valve 1804 is regulated by means of control unit 1812. A first command pulse 1 of control unit 1812 controls valve 1804 and a second command pulse 2 controls a delayed radio frequency pulse as well as a delayed light source pulse.

Example 1

An experiment was performed to demonstrate the operating principles of the present invention in which transparent light diffusing adhesive "Magic Tape," manufactured by 3M, having a thickness of 100 microns was attached to the distal end of an Alexandrite laser unit having a diameter of 8 mm. The energy level of the laser beam is 11 J/pulse. The laser beam was directed to the white (rear) side of a black developed photographic paper having a thickness of 300 microns. For comparison, the laser beam was also directed to the photographic paper without the use of the adhesive tape.

The ablation of the black paper after the beam had propagated and scattered through the white paper provides a visual simulation of the capability of the laser beam to penetrate transparent light-scattering skin in order to treat black hair follicles (or any other type of lesion) under the skin.

The energy of the laser beam transmitted through the adhesive tape, which caused the laser beam to scatter, was measured by directing the beam to an energy meter located at a distance of 1 mm from the distal end of the laser unit. The energy of the scattered laser beam dropped from 11 to 10 J. The results of this experiment indicate that the diffusively transmitting element did not absorb a significant amount of energy, since a loss of 10% is expected in any case due to Fresnel reflection.

When the laser beam was directed to the white (rear) side of a developed photographic plate at a distance of 1 mm, an ablation of the black color on the opposite side of the photographic paper resulted. There was no difference in the results between usage of light diffusing tape or not. This experiment demonstrates that the performance of a non-coherent Alexandrite laser beam, according to the present invention, at a distance of 1 mm is essentially equal to the corresponding coherent laser beam.

When the laser beam was directed, without the addition of light diffusing tape, at the photographic paper from a distance of at least 8 mm, an ablation resulted that is identical to that which was generated from a short distance of 1 mm. However, when light diffusing tape was applied to the exit aperture of the laser unit from a distance of at least 8 mm, the scattered beam did not result in an ablation. Accordingly, the present invention allows for a high level of safety and lack of damage to bodily tissue when disposed at a relatively large distance therefrom.

Example 2

In a second experiment a long pulse Alexandrite laser unit having a wavelength of 755 nm, pulse duration of 90 msec, and having an energy density of 25 J/cm$^2$ was used for hair removal. A diffusing unit with an ultra-densely woven polymer-based diffuser having a half angle of 15 degree produced by Barkan or a holographic diffuser produced by Physical Optics Corporation (USA) having a half angle of 40 degrees was employed. The diffusers were used in a one-time basis. Chilling gel was applied between the diffuser and the skin.

Each pulse of a laser beam scattered by a diffusing unit formed a spot of 5.5 mm on various skin locations including arms, bikini lines and armpits of 10 patients. Full hair removal was noticeable immediately after the firing of the laser beam. Each spot was compared to a control area with an identical diameter formed by an unscattered laser beam generated by the same laser unit with similar parameters, and similar results were achieved. Hair did not return to those spots for a period of one month.

Example 3

A long pulse Alexandrite laser unit having a wavelength of 755 nm, pulse duration of 40 msec, and having an energy level of 1.20 J is suitable for hair removal.

The diameter of the diffusing unit is 7 mm, and its scattering half angle is 60 degrees. A diffusing unit comprising a diffuser with a small scattering angle, a highly divergent lens and a light guide is added to the distal end of the laser unit.

The prior art energy density of 10.50 J/cm$^2$ is not significantly reduced with the employment of a diffusing unit. The laser unit operates at 25 J/cm$^2$ and generates a radiance of 8 J/cm$^2$/sr. Since the acceptable radiance limit according to ANSI Z 136.1 is 4.3 J/cm$^2$/sr, bystanders are required to use protective eyeglasses with 50% optical attenuation, an attenuation similar to that of sunglasses and an order of 100,000 less than typical protective eyeglasses worn during operation of a laser unit. For a larger target area, a scanner such as the Epitouch model manufactured by Lumenis may be used.

A diffusing unit having a diameter of up to 7 mm is particularly suitable for lower energy lasers, which are relatively small, remove hair at a slower speed from limited area and are inexpensive. An application of such a laser, when employed with a diffusing unit, includes the removal of eyebrows.

Example 4

A pulsed Nd:YAG laser unit such as one produced by Altus (USA) or Deka (Italy) having a wavelength of 1064 nm, pulse duration of 100 msec, and having an energy level of 0.5-60 J is suitable for hair removal at an energy density ranging from 35-60 J/cm$^2$.

A diverging unit with an array of focusing lenslets, an array of lenses provided with reflective coating on its distal side, and a plurality of convex reflectors attached to a transparent plate is used, such that the diverging half angle is close to 60 degrees. When a laser beam having an energy density of 40 J/cm$^2$ is generated, a radiance of 12.7 J/cm$^2$/sr at the exit of the diverging unit is induced, approximately half of the maximal permitted radiance according to ANSI Z 136.1.

Example 5

A long pulse diode laser unit having a wavelength ranging from 810-830 nm, or of 9.10 nm or 940 nm pulse duration ranging from 1.200 msec, and having an energy level of 0.5-30 J is suitable for hair removal at an energy density ranging from 20-50 J/cm$^2$.

The diameter of the treated area, or spot size, ranges from 1.20 mm. The diffusively transmitting element is preferably made from fused silica, sapphire, or is a holographic diffuser used in conjunction with a light guide or with any other diffusing unit described hereinabove. The scattering half angle is close to 60 degrees. A scanner may be integrated with the diffusing unit. The delivery system to which the diffusing unit is attached may be a conical light guide, such as that manufactured by Coherent or Lumenis, a guide tube produced e.g. by Diomed or a scanner produced e.g. by Assa. With a diffusing unit having a diameter of 5 mm and a laser beam generated with an energy density of 20 J/cm$^2$ and a pulse duration of 100 msec, the radiance at the exit of the diffusing unit is 9.6 J/cm$^2$/sr, lower than the maximal permitted radiance value of 11.0 J/cm$^2$/sr.

Example 6

A miniature diode laser unit for home use operating at a wavelength of approximately 810 nm, or 940 nm, such as one produced by Dornier, Germany, and having a power level of 4 W is suitable for hair removal. The invention converts a continuous working diode laser unit, which is in a high safety class and usually limits operation to the medical staff, into a lower safety class, similar to non-coherent lamps of the same power level.

The diffusing unit utilizes an angular beam expander with a convex reflector, a concave reflector having an inner diameter of 16 mm, a 10-degree glass diffuser, and a light guide having a length of 20 mm and an inner diameter of 2 mm. The diameter of the treated area, or spot size, is approximately 2 mm. The energy density at the exit of the light guide is 30 J/cm$^2$ and the radiance thereat is approximately 10 J/cm$^2$/sr. A scanner may be integrated with the diffusing unit. The diode laser may also be used without a scanner, in which case the laser will be pulsed for a duration of approximately 300 msec.

Example 7

A Ruby laser unit having a wavelength of 694 nm, pulse duration ranging from 0.5-30 msec, and having an energy level of 0.2-20 J is suitable for hair removal.

The diameter of the treated area, or spot size, ranges from 1-20 mm. The larger spot sizes can be generated by Ruby lasers manufactured by Palomar, ESC and Carl Basel, which provide an energy density ranging from 10-50 J/cm$^2$. The smaller spot sizes can be generated by inexpensive low energy lasers, which are suitable for non-medical personnel.

A multi-component diffusing or diverging unit may be used. The laser unit is much safer than a conventional laser unit A scanner, such as manufactured by Assa of Denmark or by ESC, may be used to displace a reflected collimated beam from one aperture to another formed within the diffusing or diverging unit. The scanning rate is variable, and the dwelling time at each location ranges from 20-300 msec.

Example 8

High risk laser units, such as Nd:YAG having a wavelength of 1.32 microns and manufactured by Cooltouch with a pulse duration of up to 40 msec, a dye laser having a wavelength of 585 nm and manufactured by N-Light/SLS/ICN, or a Nd:Glass laser having a wavelength of 1.55 microns with a pulse duration of 30 millisec may be used for non-ablative skin rejuvenation. This application is aimed at the treatment of rosacea, mild pigmented lesions, reduction of pore sizes in facial skin and mild improvement of fine wrinkles, without affecting the epidermis. The advantage of these lasers for non-ablative skin rejuvenation is related to the short learning curve and more predicted results due to the small number of treatment parameters associated with the single wavelength. By implementing a diffusing unit, the laser unit becomes safe and may be operated by non-medical personnel.

An N-Light laser unit is initially operated at an energy density of 2.5 $J/cm^2$ for collagen contraction. The addition of a diffusing unit makes the laser unit as safe as an IPL. The addition of a multi-component diffusing or diverging unit with a divergent half angle of 60 degrees and an exit diameter of 5 mm results in a radiance level of 0.79 $J/cm^{2/}sr$, which is equal to maximal accepted limit.

A laser beam may be generated with a considerably less expensive laser unit, having an energy level ranging from 0.5-3 J and a slow repetition rate such as 1 pps, and generating a spot size ranging from 2-4 mm. In the case of wrinkle removal, the operator may follow the shape of the wrinkles with a small beam size. Such a non-coherent laser beam having a beam size of 2-4 mm is particularly suitable for aestheticians. Using a diffusing unit depicted in FIG. 10b with a 10 degree diffuser and a light guide having a length of 30 mm results in a laser unit with a radiance of approximately 0.5 $J/cm^2/sr$.

Example 9

A pulsed Nd:YAG laser unit having a wavelength of 1064 nm and manufactured by ESC and having an energy level of 0.5-60 J is suitable for treatment of vascular lesions. The pulse duration ranges from 1.200 msec, depending on the size of the vessels to be coagulated (300 microns to 2 mm) and the depth thereof below the surface of the skin. A LICAF (Litium Calcium Fluoride) laser unit at a wavelength of 940 nm may also be advantageously used for this application, and its associated laser beam is better absorbed by blood than the Nd:YAG or Dye laser. A Dye laser at a wavelength of 585 nm and manufactured by Candela may be used to treat vessels located at a low depth below the skin surface, such as those observed in port wine stain, telangectasia and spider veins.

The diameter of the treated area, or spot size, ranges from 1-10 mm, depending on the energy level. A multi-component diffusing or diverging unit is used, due to the relatively high energy density of greater than 90 $J/cm^2$ needed for the treatment of deep vascular lesions. A scanner may be integrated with the diffusing unit.

Example 10

Q-Switch laser units having a pulse duration ranging from 10-100 nsec and having an energy density of 0.2-10 $J/cm^2$ is suitable for removal of pigmented spots, mostly on the face and hands, as well as removal of a tattoos. A Q-switched Ruby laser as manufactured by ESC or Spectrum, a Q-Switch Alexandrite laser manufactured by Combio, and a Q-Switch Nd:YAG laser may be used for such an application.

The diameter of the treated area, or spot size, ranges from 1-10 mm, depending on the energy level. A diffusing unit utilizing two diffusively transmitting elements is used, wherein one is fixed while the other is axially displaceable such that both elements are essentially in contact with each other in an active position, e.g. a gap of approximately 0.2 mm when a laser beam is fired. The gap between the two elements is approximately 15 cm when the laser is not fired. The diameter of the diffusing unit is 6 mm. Each diffusively transmitting element is preferably made from glass, sapphire or polymer.

The addition of such a diffusing unit with an axially displaceable diffuser to the aforementioned laser units is instrumental in rendering pigmented lesion and tattoo removal to be a considerably less risky procedure. Tattoo removal is achieved only by means of a laser beam, and is not attainable with intense pulse light sources.

The removal of pigmented lesions may also be performed with the use of an Erbium laser unit operated at a wavelength of 3 microns. Most pigmentation originates from the epidermis, and such a laser beam penetrates only a few microns into the skin. With implementation of a diffusing unit, this procedure may not necessarily be performed by medical specialists. Aestheticians will be able to treat a large number of patients, particularly since an Erbium laser is relatively inexpensive.

Another application of the present invention involves the field of dentistry, and relates to the treatment of pigmented lesions found on the gums. Q-switched as well as Erbium lasers may be used for this application.

Example 11

A $CO_2$ laser may be used for wrinkle removal. In prior art devices, such a laser is used in two ways in order to remove wrinkles: by ablation of a thin layer of tissue at an energy density greater than 5 $J/cm^2$ with a Coherent Ultrapulse, ESC Silktouch, or Nidek Coe laser and scanner for a duration less than 1 msec; or by non-ablative heating of collagen in the skin for lower energy densities, such as at 3 W, which may be achieved by operation of a continuously working ESC derma-K laser for 50 msec on a spot having a diameter of 3 mm.

With implementation of the present invention in which a multi-component diffusing or diverging unit is attached to a $CO_2$ laser, a laser beam having a wavelength of 10.6 microns may be generated. As opposed to other far infrared sources whose thermal and spectrally broad bandwidth involves less control of penetration depth, the interaction of a laser beam with tissue according to the present invention is highly controllable and its duration can be very short.

The diffusing and diverging units are preferably made from a lenslet that is transparent to a $CO_2$ laser beam such as ZnSe or NaCL. The diameter of the diffusing unit ranges from 1.10 mm. The divergent angle is greater than the minimal acceptable value so as to produce a radiance level at the exit beam that is essentially eye safe.

During ablation, a clear transmitting element of the diffusing unit is separated from the tissue to be treated by a thin spacer having a thickness of approximately 1 mm to allow for the evacuation of vapors or smoke produced during the vaporization process.

Similarly an Erbium laser unit operating at an energy density above 2 J/cm$^2$ and generating a laser beam greater than 3 microns may be used for wrinkle removal. Ablation is shallower than attained with a $CO_2$ laser and application of an Erbium laser unit can be extended to tattoo or permanent make up removal.

Example 12

A Nd:YAG or other laser unit may be used for treatment of herpes. A diode laser with selective absorption of Cyanin green or other materials by fatty lesions may be used for treatment of acne. Both of these lasers may be used for treatment of hemorrhoids and for podiatric lesions on the feet.

Example 13

A dye laser unit operating at a wavelength of approximately 630 nm or 585 nm, or at other wavelengths which are absorbed by natural porpherins present in P acne bacterias, such as produced by Cynachore or SLS, as well as a laser unit operating at 1.45 microns as produced by Candella, may treat acne lesions. The addition of a diffusing or diverging unit to the laser unit may considerably enhance eye safety and simplify the use of the laser unit for such treatments by nurses and non-medical staff.

Example 14

$CO_2$, diode and Nd:YAG laser units operating at an average power of approximately 1-10 W are currently used by physicians to treat pain. The addition of a diffusing unit may enable the use of a highly safe device for that procedure in pain clinics by non-medical personnel. Each laser unit may generate a number of repetitively occurring sets of pulses, during a period of approximately 3 seconds. The delivery system of the laser beam may be an articulated arm or an optical fiber.

Example 15

A diode laser unit manufactured by Candella (USA) generating a laser beam with an energy density of 10 J/cm$^2$, a wavelength of 1445 nm, a pulse duration of 100 msec and a spot size of 3 mm is suitable for non-ablative photorejuvenation.

A diverging unit with a single converging lens focuses the beam to a focal zone 1.5 mm proximate to the distal end of the diverging unit and produces a half angle divergence of 45 degrees. The diverging unit is provided with a shield located 10 mm distal to the focal point, whereat the energy density is reduced to an eye safe level of 0.2 J/cm$^2$ and a spot size is 23 mm.

Example 16

It is advantageous to use an eye-safe laser unit for welding. The employment of a diffusing unit is an excellent way to reduce the risks associated with laser welding.

When welding thin transparent parts, such as those made from plastic, e.g with a diode laser unit, it is often advantageous to employ a large surface scanner or a large diameter beam which will irradiate a large surface area and selectively activate all targets with appropriate chromophores (by heat). Such a scanner is in contrast to a scanner which is specifically targeted to the geometrical locations at which welding materials are present. The dwelling time of the welding laser beam at the targets depends on the size of the welding element and the depth of material to be melted. The dwelling time is also dependent on the size of a target treated in photothermolysis. As an example, welding a strip having a thickness of 50 micron to a substrate necessitates a dwelling time of approximately 1 msec, while a strip having a thickness of 200 microns requires a dwelling time of 16 msec. The dwelling time is proportional to the square of the thickness. Some welding chromophores are transparent in the visible part of the spectrum, but exhibit strong absorption in the near infrared part of the spectrum.

Example 17

Another industrial application for the present invention is associated with microstructures to be evaporated. Paint stains or ink may be selectively evaporated from surfaces such as clothes, paper and other materials that need cleaning by use of various pulsed lasers. One example of this application is related to the restoration of valued antiques. Another example is the selective vaporization of metallic conductors which are coated on materials such as glass, ceramics or plastics. Vaporization of metallic conductors can be achieved with a pulsed laser, which is generally separated by a short distance from a target and whose beam has a duration ranging from 10 nanoseconds to 10 milliseconds. Pulsed Nd:YAG lasers are the most commonly used ablative industrial lasers, although other lasers are in use as well. Pulsed Nd:YAG industrial lasers may attain an energy level of 20 J concentrated on a spot of 1 mm, equivalent to an energy density of 2000 J/cm$^2$. The addition of a diffusing unit to an industrial laser considerably increases the safety of the ablative device.

Pulsed Nd:YAG laser units are also suitable for improving the external appearance of larger structures, such as the cleaning of buildings, stones, antique sculptures and pottery. The laser units in use today are extremely powerful, having a continuously working power level of up to 1 kW, and are therefore extremely risky. The addition of a diffusing unit considerably improves the safety of these laser units.

A diffusing unit, when attached to an Excimer laser unit, is suitable for photo-lithography, or for other applications which use an Excimer laser unit for a short target distance.

With the addition of a multi-component diffusing or diverging unit, all of these applications become much safer to a user.

Example 18

An experiment was performed to determine the time response of skin erythema following application of a vacuum onto various skin locations. A pipe of 6 mm diameter was sequentially placed on a hand, eye periphery, arm, and forehead at a subatmospheric pressure of approximately 100 millibar. The skin locations were selected based on the suitability for treatment: the hands and eye periphery for wrinkle removal, arm for hair removal, and forehead for port wine stain treatment. The vacuum was applied for the different periods of time of 1/10, 1/4, 1, 2, 3 seconds and then stopped. The erythema level and erythema delay time were then measured.

The response time of the hand and eye periphery was ½ sec, the response time of the arm was 1 second and the response time of the forehead was ½ second. Accordingly, the experimental results indicate that the necessary delay between the application of the vacuum and firing of the laser or intensed pulsed light is preferably less than 1 second, so as not to delay the total treatment time, since the repetition rate of most laser or intensed pulsed light sources is generally less than 1 pulse/sec.

The erythema delay time was less than 1 second, and therefore the experimental results indicate that patients will not sense appreciable aesthetic discomfort following treatment in accordance with the present invention.

Example 19

An intense pulsed light system comprising a broad band Xe flashlamp and a cutoff filter for limiting light transmission between 755 nm and 1200 nm is suitable for aesthetic treatments, such that light delivered through a rectangular light guide is emitted at an energy density of 20 J/cm$^2$ and a pulse duration of 40 milliseconds, for hair removal with respect to a treated area of 15×45 mm.

While efficacy of such a light system for the smoothening of fine wrinkles, i.e. photorejuvenation, is very limited by prior art devices, due to the poor absorption of light by blood vessels at those wavelengths, enhanced light absorption in targeted skin structures in accordance with the present invention would increase the efficacy.

A transparent vacuum chamber of 1 mm height is preferably integrally formed with a handpiece through which intense pulsed light is directed. A diaphragm miniature pump, such as one produced by Richly Tomas which applies a vacuum level of 100 millibar, is in communication with the chamber and a control valve is electronically opened or closed. When the control valve is opened, the pressure in the vacuum chamber is reduced to 100 millibar within less than 10 milliseconds. As a result of the application of vacuum, the skin slightly protrudes into the vacuum chamber at an angle as small as $1/15$-$1/45$ radian (height divided by size of skin target) and a height of 1 mm. Blood is drawn into the drawn skin target, which achieves a much pinker hue and therefore has a higher light absorbence. The increased redness of the skin increases the light absorption by a factor of 3. As a result, the efficacy of the aforementioned light system is similar to that of a prior art system operating at 60 Joules/cm$^2$, which is known to provide adequate results in wrinkle removal procedures. At energy density levels as high as 20 J/cm$^2$, it is preferable to chill the epidermis in order to avoid a risk of a burn. Epidermis chilling is accomplished by means of an aluminum plate, which is chilled by a thermoelectric chiller. The plate is in contact with the skin and chills the skin just before the handpiece is moved to the chilled skin target, prior to treatment.

The invention has thereby converted an intense pulsed light device for hair removal into an efficient photorejuvenation device as well.

Example 20

An Nd:YAG laser operating at 1064 nm, 90 milliseconds pulse duration, and energy density of 70 J/cm$^2$ is suitable for prior art hair removal having a spot size of 7 mm. By prior art hair removal, absorption of light in the hair shaft melanin is limited, with a contributory factor in hair removal being attributed to the absorption of light by blood in the hair follicle bulb zone. Since the energy density level of 70 J/cm$^2$ is risky to the epidermis of dark skin, it would be preferable to operate the laser at 40 J/cm$^2$.

A vacuum chamber is preferably integrally formed with a handpiece through which intense pulsed light is directed, at a distance of 1 mm from the skin target. A vacuum is applied to the skin target for 2 seconds. The blood concentration near the follicle bulb and in the bulge at a depth of 4 and 2 mm, respectively, is increased by a factor of 2. As a result the laser is operated with the same efficacy at energy levels closer to 40 J/cm$^2$ and is much safer.

Example 21

A Dye laser emitting light at a wavelength of 585 nm, with a spot size of 5 mm and pulse duration of 1 microsecond, is used by prior art methods for treatment of vascular lesions, such as telangectasia, and port wine stains, at an energy density level ranging from 10.15 J/cm$^2$ and for the smoothing of wrinkles at an energy density level of 3-4 J/cm$^2$. Some disadvantages of the prior art method are the purpura that is often produced on the skin during vascular treatments and the very large number of treatments (more than 10) which are necessary for the smoothening of wrinkles.

By applying a controlled vacuum to a vacuum chamber in contact with a skin target, having either a moderate vacuum level of approximately 600 miilibar or a vacuum which is modulated at a frequency of 10 Hz for 1 seconds prior to the firing of the laser, the efficacy of the laser is enhanced. Consequently it is possible to treat vascular lesions at 7 J/cm$^2$ without creating a purpura and to remove wrinkles with a much smaller number of treatments (5).

Example 22

A prior art diode laser operated at 810 nm or a Dye laser is suitable for treating vascular rich psoriatic skin, wherein the treated area per pulse is approximately 1 cm$^2$. By employing a vacuum chamber attached to the distal end of the handpiece of either of these lasers, blood is drawn to the lesion and treatment efficacy is improved. The vacuum may be applied for 2 seconds prior to firing the laser beam.

Example 23

A deep penetrating laser, such as a pulsed diode laser at 940 nm, an Nd:YAG laser, or an intense pulsed light source operating at an energy density of 30 J/cm$^2$, is suitable for thermally damaging a gland, when a vacuum chamber is attached to the distal end of the handpiece thereof. When vacuum is applied for a few seconds, e.g. 1.10 seconds, above a gland such as a sweat gland, excessive blood is drawn into the gland. After the pulsed laser beam is directed to the skin, the absorption of the laser beam by the drawn blood generates heat in the gland, which is thereby damaged. It is therefore possible to more efficiently thermally damage glands with a laser or intense pulsed light source when vacuum is applied to the skin.

Example 24

By placing a vacuum chamber on a skin target in accordance with the present invention prior to the firing of an intense pulsed light source, the treatment energy density level for various types of treatment is significantly reduced with respect with that associated with prior art devices. The treatment energy density level is defined herein as the minimum energy density level which creates a desired change in the skin structure, such as coagulation of a blood vessel, denaturation of a collagen bundle, destruction of cells in a gland, destruction of cells in a hair follicle, or any other desired effects.

The following is the treatment energy density level for various types of treatment performed with use of the present invention and with use of prior art devices:

a) treatment of vascular lesions, port wine stains, telangectasia, rosacea, and spider veins with light emitted from a dye laser unit and having a wavelength of 585 nm: 5-12 J/cm$^2$ (present invention), 10-15 J/cm$^2$ (prior art);

b) treatment of vascular lesions, port wine stains, telangectasia, rosacea, and spider veins with light emitted from a diode laser unit and having a wavelength of 940 nm: 10-30 J/cm$^2$ (present invention), 30-40 J/cm$^2$ (prior art);

c) treatment of vascular lesions with light emitted from an intense pulsed non-coherent light unit and having a wavelength of 570-900 nm: 5-20 J/cm$^2$ (present invention), 12-30 J/cm$^2$ (prior art);

d) treatment of vascular lesions with light emitted from a KPP laser unit manufactured by Laserscope, USA, and having a wavelength of 532 nm: 4-8 J/cm$^2$ (present invention), 8.16 J/cm$^2$ (prior art);

e) photorejuvination with light emitted from a dye laser unit and having a wavelength of 585 nm: 2-4 J/cm$^2$ and requiring 6 treatments (present invention), 2-4 J/cm$^2$ and requiring 12 treatments (prior art);

f) photorejuvination with light emitted from a an intense pulsed non-coherent light unit and having a wavelength ranging from 570.900 nm: 5.20 J/cm$^2$ (present invention), approximately 30 J/cm$^2$ (prior art);

g) photorejuvination with a combined effect of light emitted from an intense pulsed non-coherent light unit and having a wavelength ranging from 570-900 nm and of a RF source: 10 J/cm$^2$ for both the intense pulsed non-coherent light unit and RF source (present invention), 20 J/cm$^2$ for both the intense pulsed non-coherent light unit and RF source (prior art); and h) hair removal with light emitted from a Nd:YAG laser unit and having a wavelength of 1604 nm: 25-35 J/cm$^2$ (present invention), 50-70 J/cm$^2$ (prior art).

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. An apparatus for enhancing the absorption of light in targeted skin structures, comprising:
    an intense pulsed light source;
    a U-shaped evacuation chamber positionable on a skin target;
    a handpiece for directing intense pulsed light to the skin target which is connected to, or integral with, the evacuation chamber;
    a clear transmitting element mounted in the distal end of the U-shaped evacuation chamber, the transmitting element being transparent to intense pulsed light directed to the skin target and suitable for transmitting the intense pulsed light in a direction substantially normal to a skin surface adjoining the skin target;
    a rim for sealing the peripheral contact area between the skin surface adjoining the skin target and the wall of the handpiece; and
    means for applying a vacuum to the evacuation chamber including a first conduit and a second conduit in communication with the U-shaped evacuation chamber, the second conduit including a distal opening that can be occluded during vacuum application, the level of the applied vacuum suitable for drawing the skin target to the evacuation chamber and for increasing the concentration of blood and/or blood vessels within a predetermined depth below the skin surface of the skin target, optical energy associated with the directed intense pulsed light being absorbed within the predetermined depth.

2. The apparatus according to claim 1, wherein the vacuum applying means comprises a vacuum pump and at least one control valve.

3. The apparatus according to claim 1, further comprising control means for controlling operation of the vacuum pump, the at least one control valve, and the intense pulsed light source.

4. The apparatus according to claim 3, wherein the control means is suitable for firing the intense pulsed light source after a predetermined delay following operation of the vacuum pump.

5. The apparatus according to claim 3, wherein the control means is suitable for firing the intense pulsed light source after a predetermined delay following opening of the at least one control valve.

6. The apparatus according to claim 5, wherein the control means is suitable for increasing the pressure in the evacuation chamber to atmospheric pressure following deactivation of the intense pulsed light source, to allow the effortless repositioning of the evacuation chamber to a second skin target.

7. The apparatus according to claim 3, further comprising a pulsed radio frequency (RF) source for directing suitable electromagnetic waves to the skin target.

8. The apparatus according to claim 7, wherein the frequency of the electromagnetic waves ranges from 0.2 to 10 MHz.

9. The apparatus according to claim 7, wherein the RF source is a bipolar RF generator which generates alternating voltage applied to the skin surface via wires and electrodes.

10. The apparatus according to claim 7, wherein the control means is suitable for transmitting a first command pulse to the at least one control valve and a second command pulse to both the intense pulsed light source and RF source.

11. The apparatus according to claim 3, further comprising an erythema sensor, said sensor suitable for measuring the degree of skin redness induced by the vacuum applying means.

12. The apparatus according to claim 11, wherein the control means is suitable for controlling, prior to firing the light source, the energy density of the light emitted from the light source, in response to the output of the erythema sensor.

13. The apparatus according to claim 1, wherein the intense pulsed light source is selected from a group comprising a Dye laser, Nd:YAG laser, Diode laser, Alexandrite laser, Ruby laser, Nd:YAG frequency doubled laser, Nd:Glass laser and a non-coherent intense pulse light source.

14. The apparatus according to claim 1, wherein the light emitted from the light source has any wavelength band between 400 nm and 1800 nm.

15. An apparatus for enhancing the absorption of light in targeted skin structures, comprising:
- an intense pulsed light source;
- a handpiece for directing light from the intense pulsed light source to the targeted skin structures, the intense pulsed light source connected to, or integral with, the handpiece, the handpiece further comprising:
  - an evacuation chamber defined by a wall of the handpiece, the evacuation chamber positionable on a region of skin including the targeted skin structures;
  - a transmitting element mounted in the distal end of the evacuation chamber, the transmitting element being substantially transparent to the light directed to the targeted skin structures, and suitable for transmitting the light in a direction substantially normal to a skin surface of the region of skin including the targeted skin structures; and
  - a rim on an end of the wall for sealing a peripheral contact area between the skin surface and the wall of the handpiece;
- a vacuum system for applying vacuum to draw the region of skin including the targeted skin structures into the evacuation chamber; and
- a first conduit and a second conduit defined in the evacuation chamber, the first conduit communicating vacuum to the evacuation chamber, the second conduit including a distal opening that can be occluded during vacuum application, optical energy associated with the light being absorbed within a predetermined depth below the skin surface of the skin target.

16. The apparatus of claim 15 wherein the vacuum system is configured to apply a level of vacuum suitable for increasing the concentration of blood and/or blood vessels within the predetermined depth 17. The apparatus of claim 15 wherein the vacuum system comprises a vacuum pump and at least one control valve associated with the first conduit.

18. The apparatus of claim 17 further comprising control means for controlling operation of the vacuum pump, the at least one control valve, and the intense pulsed light source.

19. The apparatus of claim 18 wherein the control means is suitable for firing the intense pulsed light source after a predetermined delay following operation of the vacuum pump.

20. The apparatus of claim 18 wherein the control means is suitable for firing the intense pulsed light source after a predetermined delay following opening of the at least one control valve.

21. The apparatus of claim 18 wherein the control means is suitable for increasing the pressure in the evacuation chamber to atmospheric pressure following deactivation of the intense pulsed light source, to allow the effortless repositioning of the evacuation chamber to a second skin target region.

22. The apparatus of claim 15 wherein the intense pulsed light source is selected from the group comprising a dye laser, a Nd:YAG laser, a diode laser, an alexandrite laser, a ruby laser, a Nd:YAG frequency doubled laser, a Nd:Glass laser and a non-coherent intense pulse light source.

23. The apparatus of claim 15 wherein the light emitted from the intense pulsed light source has one or more wavelengths from about 400 nm to about 1800 nm.

24. The apparatus of claim 15 wherein the intense pulsed light source is a diode laser.

25. The apparatus of claim 15 wherein the intense pulsed light source is a non-coherent intense pulse light source.

26. The apparatus of claim 15 wherein the second conduit includes a valve for occluding the distal opening.

27. The apparatus of claim 26 further comprising a controller adapted to operate the vacuum system, the valve for occluding the distal opening, and the intense pulsed light source.

* * * * *